US009968292B2

United States Patent
Gardner et al.

(10) Patent No.: US 9,968,292 B2
(45) Date of Patent: May 15, 2018

(54) THERAPEUTIC ANGIOGENESIS FOR TREATING ERECTILE CONDITIONS

(71) Applicant: CARDIOVASCULAR BIOTHERAPEUTICS, INC., Las Vegas, NV (US)

(72) Inventors: Vance Gardner, Irvine, CA (US); John Jacobs, Berkeley, CA (US); Laurence R Meyerson, Henderson, NV (US); Mickael Flaa, Las Vegas, NV (US)

(73) Assignee: CARDIOVASCULAR BIOTHERAPEUTICS, INC., Dallas, TX (US)

( * ) Notice: Subject to any disclaimer, the term of this patent is extended or adjusted under 35 U.S.C. 154(b) by 0 days. days.

(21) Appl. No.: 15/675,595

(22) Filed: Aug. 11, 2017

(65) Prior Publication Data

US 2017/0340266 A1  Nov. 30, 2017

Related U.S. Application Data

(63) Continuation of application No. PCT/US2016/017965, filed on Feb. 15, 2016.

(60) Provisional application No. 62/116,757, filed on Feb. 16, 2015, provisional application No. 62/159,879, filed on May 11, 2015.

(51) Int. Cl.

| | |
|---|---|
| *A61K 38/19* | (2006.01) |
| *A61K 31/195* | (2006.01) |
| *A61K 31/135* | (2006.01) |
| *A61B 5/00* | (2006.01) |
| *A61B 5/026* | (2006.01) |
| *A61B 6/00* | (2006.01) |
| *A61B 8/06* | (2006.01) |
| *A61B 8/08* | (2006.01) |
| *A61K 9/00* | (2006.01) |
| *A61K 38/18* | (2006.01) |
| *A61L 24/00* | (2006.01) |
| *A61K 31/137* | (2006.01) |
| *A61K 45/00* | (2006.01) |

(52) U.S. Cl.

CPC .......... *A61B 5/4393* (2013.01); *A61B 5/0263* (2013.01); *A61B 5/4337* (2013.01); *A61B 5/4839* (2013.01); *A61B 6/507* (2013.01); *A61B 6/5217* (2013.01); *A61B 8/06* (2013.01); *A61B 8/5223* (2013.01); *A61K 9/0014* (2013.01); *A61K 9/0019* (2013.01); *A61K 9/0034* (2013.01); *A61K 31/137* (2013.01); *A61K 38/1825* (2013.01); *A61K 45/00* (2013.01); *A61L 24/00* (2013.01)

(58) Field of Classification Search

CPC ..... A61K 38/19; A61K 31/195; A61K 31/135
USPC .......................................... 514/9.1, 561, 649
See application file for complete search history.

(56) References Cited

U.S. PATENT DOCUMENTS

| | | | | |
|---|---|---|---|---|
| 6,165,975 A | * | 12/2000 | Adams | A61K 31/04 |
| | | | | 424/718 |
| 6,414,027 B1 | * | 7/2002 | Neal | A61K 9/0034 |
| | | | | 514/573 |
| 6,706,682 B2 | * | 3/2004 | Shabsigh | F27D 27/00 |
| | | | | 514/8.1 |
| 6,747,063 B2 | * | 6/2004 | Adams | A61K 31/198 |
| | | | | 514/18.3 |
| 6,852,323 B2 | * | 2/2005 | Lue | A61K 38/1825 |
| | | | | 424/198.1 |
| 8,575,111 B2 | * | 11/2013 | Santos | A61K 31/165 |
| | | | | 514/1.1 |
| 9,498,516 B2 | * | 11/2016 | Suh | A61K 38/1891 |
| 2002/0032153 A1 | | 3/2002 | Whitehouse | |
| 2007/0283969 A1 | | 12/2007 | Yamasaki et al. | |

FOREIGN PATENT DOCUMENTS

| | | |
|---|---|---|
| RU | 2247533 C1 | 3/2005 |
| WO | 1991005320 A1 | 4/1991 |
| WO | 199116021 A1 | 10/1991 |

OTHER PUBLICATIONS

Marshall J. Stein et al., New Advances in Erectile Technology, Therapeutic Advances in Urology, 2014, vol. 6(1), pp. 15-24, abstract, p. 20, left col.
International Searching Authority, Federal Institute of Industrial Property, Form PCT/ISA/210 and 237 for IA Application No. PCT/US2016/017965, International Search Report and Written Opinion, dated Aug. 11, 2016.

\* cited by examiner

*Primary Examiner* — Raymond J Henley, III
(74) *Attorney, Agent, or Firm* — Brainspark Associates, LLC

(57) ABSTRACT

Disclosed are devices, methods and surgical procedures for detecting, imaging, analyzing, diagnosing and/or treating vascular disorders and related conditions of the human and mammalian body in males and/or females. In particular embodiments, treatments include methods for imaging, analyzing and improving erectile dysfunction and related conditions and potentially increasing angiogenesis in response to specifically diagnosed conditions.

20 Claims, 9 Drawing Sheets

THERAPEUTIC ANGIOGENESIS FOR TREATING ERECTILE CONDITIONS

CROSS REFERENCE TO RELATED APPLICATIONS

This application claims priority to PCT Patent Application Serial No. PCT/US2016/17965, entitled "THERAPEUTIC ANGIOGENESIS FOR TREATING ERECTILE CONDITIONS," filed Feb. 15, 2016, which in turn claims priority to U.S. Provisional Patent Application Ser. No. 62/159,879, entitled "Therapeutic Angiogenesis for Treating Erectile Conditions," filed May 11, 2015 and U.S. Provisional Patent Application Ser. No. 62/116,757, entitled "The Future of Vascular Medicine," filed Feb. 16, 2015. The disclosures of each of these references is herein incorporated by reference in their entireties.

FIELD OF THE INVENTION

The various embodiments herein pertain to the field of detecting, imaging, analyzing, diagnosing and/or treating vascular disorders and related conditions of the human and mammalian vascular system of males and/or females. In particular embodiments, treatments include methods for imaging, analyzing and improving erectile dysfunction and related conditions and potentially increasing angiogenesis in response to specifically diagnosed conditions.

BACKGROUND OF THE INVENTION

Description of the Related Art

Impotence in males is the consistent inability to achieve or sustain an erection of sufficient rigidity for sexual intercourse. Impotence is recognized to be an age-dependent disorder, and it has recently been estimated that at least 5% of 40-year-old men and between 15% and 25% of 65-year-old men experience erectile dysfunction on a long-term basis. In 1985 in the United States, impotence accounted for more than several hundred thousand outpatient visits to physicians, and in 1998 it was estimated that approximately 10 million American men were impotent. Depending on the nature and cause of the problem, treatments historically included psychosexual therapy, hormonal therapy, administration of vasodilators such as nitroglycerin and $\alpha$-adrenergic blocking agents ("$\alpha$-blockers-"), oral administration of other pharmaceutical agents, vascular surgery, implanted penile prostheses, vacuum constriction devices and external aids such as penile splints to support the penis or penile constricting rings to alter the flow of blood through the penis. More recently, orally administered selective Phosphodiesterase-5 (PDE-5) inhibitors, such as sildenafil (Viagra), tadalafil (Cialis) and vardenafil (Levitra) have been approved for the treatment of erectile dysfunction, with additional drugs pending approval (i.e., udenafil and avanafil). These drugs selectively inhibit the action of PDE-5, which is cGMP-specific and responsible for the degradation of cGMP in the corpus cavernosum.

In healthy adult males, the process of penile erection and the subsequent return of the penis to the flaccid state involves a "delicate dance" within the male anatomy, which typically involves (1) dilation of the arteries that regulate blood flow to the lacunae of the corpora cavernosum to increase blood inflow, (2) relaxation of trabecular smooth muscle, which facilitates engorgement of the penis with blood, and (3) compression of the venules by the expanding trabecular walls to decrease venous outflow. Assuming no significant leakage of blood, when a greater amount of blood flows into the penis than out, engorgement of the penile tissues can occur—typically creating an erection. After an erection, when less blood flows in than out, engorgement of the penis can be reversed, with the flaccid state typically achieved.

A number of causes of impotence have been identified, including vasculogenic, neurogenic, endocrinologic and psychogenic. Vasculogenic impotence, which is caused by alterations in the flow of blood to and from the penis, is thought to be the most frequent organic cause of impotence. Common risk factors for vasculogenic impotence include hypertension, diabetes, cigarette smoking, pelvic trauma, and the like. Neurogenic impotence is associated with spinal-cord injury, multiple sclerosis, peripheral neuropathy caused by diabetes or alcoholism and severance of the autonomic nerve supply to the penis consequent to prostate surgery. Erectile dysfunction is also associated with disturbances in endocrine function resulting in low circulating testosterone levels and elevated prolactin levels.

Consequently, there are a considerable number of events and/or factors that may cause or enhance the effects of erectile dysfunction, and a corresponding array of medications and therapies to manage the symptoms of erectile dysfunction. However, there are few medications and/or therapies that seek to specifically target the etiology of erectile dysfunction, and none that prevent further impairment from the underlying causes of erectile dysfunction. For example, pharmacological treatment methods such as selective PDE-5 inhibitors have become increasingly popular for treatment of erectile dysfunction, but these drugs typically only "supplement" the naturally-occurring concentration and/or effects of proteins, enzymes and/or hormones on a temporary basis—they do nothing to address the underlying localized and/or systemic cause of the patient's erectile dysfunction. Moreover, there remains a significant proportion of the adult male population, which is estimated to range from 30% to 50% of ED sufferers, who experience little or no benefit from such drugs. In addition, there are a large number of individuals suffering from erectile dysfunction who take medications (for other serious medical conditions) incompatible with PDE-5 inhibitors, such as nitrate drugs or anticoagulant medications. There are many individuals who suffer from various medical conditions incompatible with PDE-5 inhibitors, such as heart disease or heart failure, strokes, uncontrolled high or low blood pressure, eye problems such as retinitis pigmentosa, severe liver disease and/or have kidney disease requiring dialysis. In addition, vasodilators only induce temporary erections following administration and do not address or treat the basic vascular/cavernosal pathology which may be causing erectile dysfunction, and there are many patients who would prefer a more permanent and/or "long-term solution" to their erectile dysfunction issues, rather than being required to ingest a medication on a frequent basis.

In addition, there are a number of sexual dysfunction issues resulting from abnormal vascular circulation that can affect females in a similar manner. Specific physiologic impairments of vasculogenic female sexual dysfunction can include vaginal engorgement and clitoral erectile insufficiency syndromes, which can include symptoms such as delayed vaginal engorgement, diminished vaginal lubrication, pain or discomfort with intercourse, diminished vaginal sensation, diminished vaginal orgasm, diminished clitoral sensation or diminished clitoral orgasm. In many cases, a root cause of such dysfunction issues could be an abnormality in the vascular physiologic processes in the affected individual(s), which might also be amendable to the various systems, devices and methods of treatment described herein.

SUMMARY OF THE INVENTION

Various aspects of the present invention include the realization of a need for improved identification and diagnosis, assessment and/or treatment of erectile dysfunction and related conditions in men and/or women suffered as a result of vasculogenic conditions, including conditions resulting from and/or related to vascular ischemia. Embodiments can include classifications of vascular abnormalities and/or deficits, pathological conditions and/or associated hemodynamic imbalances that can be based on specific parameters associated with hypoperfusion, hypoxia, ischemia and/or various forms of erectile dysfunction. Further embodiments relate to treatments for alleviating the state of hypoperfusion, hypoxia, ischemia and/or erectile dysfunction in patients to desirably lead to therapeutic improvements.

In various embodiments, an individual's assessment and/or probability of suffering from erectile dysfunction may be performed in conjunction with an assessment of the overall health of an individual's vascular system, while in other embodiments the erectile dysfunction assessment can be conducted as a precursor or predictor of the individual's overall systemic vascular health. Because erectile dysfunction often precedes major cardiac events and/or other severe medical conditions resulting from degenerative vasculature, such assessments can be much more accurate in identifying early stages of vascular degeneration than the various assessment techniques and methodologies currently practiced.

If desired, the various disclosed methods of imaging and/or assessing vasculogenic erectile dysfunction in a patient can be performed prophylactically as part of an age-related and/or general condition screening, or can be performed as part of and/or as a result of an assessment and/or diagnosis of a more general systemic patient condition such as atherosclerosis, coronary artery disease, diabetes, heart failure, peripheral artery disease and/or other conditions. Alternatively, because the effects of vasculogenic erectile dysfunction can often be more easily diagnosed (and often diagnosed much earlier) than comparable effects in other anatomical areas (i.e., coronary artery disease and/or small vessel disease), identification and/or diagnosis of vasculogenic erectile dysfunction can be used as a reliable indicator of a need for diagnosis and/or patient treatment of a variety of systemic conditions, including undiagnosed hypertension, ischemic heart conditions, vessel disease and/or diabetes.

In various embodiments, an erectile dysfunction assessment such as described herein may be particularly useful for patients beginning a course of medication treatment. Where such as assessment is performed prior to the medication treatment, it may be useful in identifying the type and/or extent of potential effects the medication may have on the erectile health of the individual, as well as assist with the determination of the minimum/maximum dosing of the medication to achieve desired effects (i.e., personalized medicine). If the medication is prescribed to treat erectile dysfunction, such an assessment may assist with determining the effectiveness of such treatment, as well as to provide guidance regarding required dosing of the medication to achieve a desired outcome. In various embodiments, imaging and assessment of an individual can be conducted prior to dosing of the medication and/or after dosing of the medication, which can allow evaluation and comparison of the medication's effect on the erectile tissues.

Various embodiments described herein can be employed to diagnose, assess, quantify and/or treat pathologies that can eventually lead to various sexual dysfunction issues in both men and women, including erectile dysfunction of male patients. In an initial step, anatomical image data can be obtained of an individual patient's anatomy. This image data can be derived from a wide variety of sources, including MRA (magnetic resonance angiography), MRI (magnetic resonance imaging), x-ray imaging, cone beam CT, digital tomosynthesis, and ultrasound, CT scans or PET or SPECT scans, as well as many others known in the art. Once image data is acquired, one or more regions of interest (ROI) of the image data can be identified and analyzed in a variety of ways, and the analyzed results can be compared to each other, to one or more defined values and/or standards and utilized to diagnose, assess and/or quantify a pathology. If desired, the analysis and diagnosis can be used as guidance for treating the patient. In various other embodiments, the results can be compared to values derived or obtained from a reference database of healthy and/or diseased patients. In other alternative embodiments, a relative assessment of such values within an individual patient can be conducted, which may be used to identify abnormal and/or anomalous readings, which may be indicators of relative deficiencies.

Various embodiments described herein can be employed to diagnose, assess, quantify and/or treat pathologies that can eventually lead to a deficient supply of blood, nutrients and/or oxygen to penile tissues and/or that create an undesired hemodynamic balance/imbalance within penile and/or related tissues. The blood supply to the penile anatomy can potentially be blocked at various stages of the route. The feeding arteries or other vascular structures themselves can narrow due to atherosclerosis with resultant supply restrictions and/or ischemia of the penile tissues. With less blood flowing into and through the penis, less blood may be available for employment in the erectile cascade, and oxygen, nutrients and other constituents of the erectile cascade (i.e., nitrous oxide and/or other chemicals/enzymes/signaling molecules) may not be available in sufficient quantities and/or available at the correct time or location(s) for an erection to be obtained and/or maintained for a sufficient duration. In addition to and/or instead of narrowing of the major blood vessels, an overall decrease in the blood flow within the penile tissues may be a primary reason for the degradation of various penile tissues and/or the onset of various conditions leading to erectile dysfunction. In a similar manner, trauma can disrupt blood and/or nutrition flow.

In at least one embodiment, a diagnosis of a hypoxic or ischemic condition or some other hemodynamic imbalance that leads to erectile dysfunction as a disorder can be made by a two-part test of firstly excluding patients with a set of exclusion criteria, and further selecting patients having documented hypoperfusion, hypoxia, ischemia and/or some hemodynamic imbalance of the affected areas. Specific exclusion criteria could include nerve damage, infection, tumors, psychological disorders and/or physical trauma involving the corpus cavernosum and/or other penile tissues.

In one exemplary embodiment, diagnosed vasculogenic erectile dysfunction can be treated by increasing perfusion in identified area(s), such as by injection of a composition that includes an angiogenic factor. In preferred embodiments, injection can be directly into a region of constricted and/or occluded blood flow, which may be within and/or proximate to one or more identified areas of hypoperfusion. The identified area or areas can be accessed percutaneously with a surgical access and delivery device such as a surgical access needle (i.e., hypodermic needle) extending through the patient's skin (i.e., subcutaneously and/or intramuscularly) and overlying soft tissues in a minimally-invasive manner, or via an existing vascular or other anatomic channel (i.e., vascular angioplasty and/or rectal/urethral access). The composition can then be introduced into the targeted anatomy of the patient through the delivery device.

In various embodiments, vasculogenic erectile dysfunction might be treated by increasing perfusion in various affected tissues areas (i.e., within the vasculature and/or penile tissues) such as by injection of a composition that includes an angiogenic factor. In preferred embodiments, injection is around the penile tissues and/or directly into the penile anatomy. In other embodiments, injection of angiogenic compounds may be positioned into and/or adjacent to other anatomical structures, including the vessels supplying blood to the various penile tissues. In some embodiments, a localized delivery system capable of forming a gel-like structure may be used to deliver the angiogenic factor. Preferably, the delivery system includes components of extracellular matrix that provide conditions suitable for angiogenesis. In some embodiments, said extracellular matrix components may be hyaluronic acid fragments. In other embodiments, said extracellular matrix components may be derivatives of collagen, or perlecan. Preferably, the gel-like structure includes a polymer capable of slow release such as a poloxamer block copolymer (Pluronic®, BASF), basement membrane preparation (Matrigel®, BD Biosciences) or collagen-based matrix such as described by U.S. Pat. No. 6,346,515, which is incorporated herein by reference.

In various embodiments, vasculogenic erectile dysfunction can be treated by administration of a medical device that generates a continuous release of a composition which includes an angiogenic factor into tissue and/or circulation so as to promote neoangiogenesis, and specifically, collateralization in the area(s) proximal to hypoperfusion. In some embodiments, the composition could further include stem cells and/or other biological treatments, which might be used in conjunction with angiogenic factors prior to, during and/or subsequent to the employment of tissue grafts to repair or replace native tissues. If desired, such compositions could be used to prepare a patient's anatomical site for an intended tissue graft or surgical procedure, could be used to prepare the tissue graft for implantation, and/or could be used to treat the patient and/or tissue graft site after implantation.

In various embodiments, a medical device may include a slow release pump such as an implantable indwelling or osmotic pump or a localized delivery system such as a polymer capable of slow release, as described herein. In other embodiments, an external medical device or dressing could be utilized to provide a topical composition to the patient's skin surface(s).

In at least one embodiment, the composition delivered by the medical device can contain not only a therapeutically sufficient concentration of a growth factor that stimulates angiogenesis, but also a chemotactic agent. Some growth factors, such as fibroblast growth factor 1 (FGF-1), are themselves chemotactic. The chemotactic agent recruits cells capable of causing or promoting angiogenesis. In some embodiments, a chemotactic agent such as stromal cell-derived factor 1 (SDF-1) is included in the composition with the growth factor. In various embodiments, the composition delivered by the medical device may contain an anti-inflammatory agent at a concentration sufficient for inhibiting possible inflammatory reactions associated with neoangiogenesis, while at the same time not inhibiting collateral blood vessel formation.

Depending upon the specific tissue structure(s) concerned, the diagnosis and/or treatment methods and systems described herein can include the selection and analysis of a plurality of relevant tissue structures. For example, where the diagnosis and/or treatment of a patient's erectile dysfunction is of interest, the methods and systems described herein can include the imaging and analysis of a wide variety of vascular and tissue structures, including vessels and related anatomical tissues that may be either or both "upstream" and/or "downstream" of the penile tissues of interest, as well as relevant anatomical structures and/or vascular passages within the penile tissues themselves. Depending upon the physician's preference and/or the relevant clinical situation, diagnosis of a vasculogenic deficiency and/or abnormality in some portion of the blood supply and/or drainage of the penile tissues may indicate a need for further treatment, as described herein.

In various embodiments, assessment of perfusion of the various regions of interest can be performed, followed by therapy that desirably increases the rate of perfusion in some or all of the vasculature of interest, followed by a subsequent assessment of perfusion so as to identify the ideal conditions for stimulation of perfusion on an individualized basis. In other related embodiments, assessment of the hemodynamic and/or blood flow conditions of the various regions of interest can be performed, followed by therapy that desirably alters the hemodynamic and/or blood flow conditions to achieve an improved and/or desired hemodynamic balance within the penile tissues, followed by a subsequent assessment of the hemodynamic and/or blood flow conditions so as to identify the ideal conditions for treatment of the patient on an individualized basis

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

DETAILED DESCRIPTION OF THE INVENTION

Figure 1:
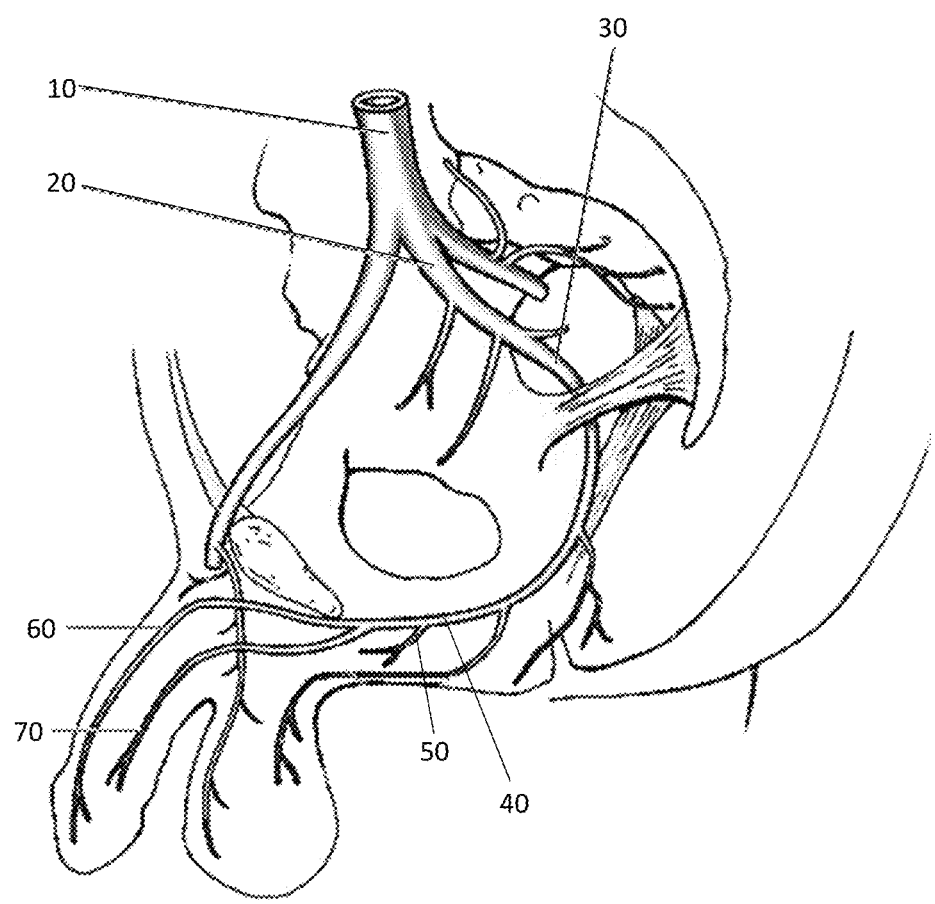
FIG. 1 depicts an exemplary arterial anatomy of a male pelvis.

The following description is presented to enable any person skilled in the art to make and use the invention.

Various modifications to the embodiments described will be readily apparent to those skilled in the art, and the generic principles defined herein can be applied to other embodiments and applications without departing from the spirit and scope of the present invention as defined by the appended claims. Thus, the present invention is not intended to be limited to the embodiments shown, but is to be accorded the widest scope consistent with the principles and features disclose herein. To the extent necessary to achieve a complete understanding of the invention disclosed, the specification and drawings of all issued patents, patent publications, and patent applications cited in this application are incorporated herein by reference. Although some embodiments are described below, these are merely representative and one of skill in the art will be able to extrapolate numerous other applications and derivations that are still within the scope of the invention disclosed.

Erection of the penis is a parasympathetic nervous system process that ultimately results in the release of neurotransmitters, nitric oxide (NO), and vasodilation of the helicine arteries in the corpus cavernosa of the penis. More particularly, NO is first derived from nonadrenergic, non-cholinergic neurotransmission through a NO synthase catalyzed reaction involving endogenous L-arginine. However, a second and principle source of NO, allowing for sustained penile erection, is derived from the endothelium. NO diffuses into smooth muscle cells to activate soluble guanylate cyclase, which catalyzes the conversion of GTP to cyclic guanosine monophosphate (cGMP), raising the intracellular concentration of cGMP. As the levels of cGMP increase, the relative levels of calcium shift and cause the cavernosal smooth muscle cells to relax. This relaxation causes dilation and enlargement of the corpora cavernosa, helicine arteries and luminar spaces. This vasodilation and enlargement exerts force on the subtunical albuginea, thereby depressing outflow of blood through the venous system. This orchestrated process results in penile rigidity and erection.

Erection of the penis is a hemodynamic phenomenon involving tissue of the corpora cavernosa and the corpus spongiosum. This tissue is a complex admixture of smooth muscle, endothelial cells, fibroblasts, and nerves that interact under stimulatory conditions in order to enhance and maintain an accessory blood supply imparting rigidity. Given the need for control of blood flow during this response, it is highly likely that vascular insufficiency and/or other hemodynamic factors have a potential to suppress and/or interfere with erectile capability. In fact, vascular insufficiency may be a common pathomechanism of erectile dysfunction. It is estimated that from 50% to 75% of the instances of erectile dysfunction can be attributed at least in part to a reduced blood flow to the penis, typically due to an underlying vascular disease.

In many cases, atherosclerosis of the pelvic arteries alone may account for about 40% of erectile dysfunction sufferers over 40 years of age with erectile dysfunction. Causes of erectile dysfunction can include arterial disease anywhere along the arterial tree from the abdominal aorta to the helicine arteries. The relevant arteries can include, from proximal to distal, the lower abdominal aorta, common iliac, internal iliac (hypogastric), internal pudendal, and penile arteries, i.e., dorsal, deep, and helicine arteries. Other possible vascular-related causes of erectile dysfunction include, but are not limited to, diabetes, hypertension, high cholesterol, renal disease, trauma, surgery and smoking Erectile dysfunction is a disease that can have multiple pathophysiologies, one of which may be insufficient blood flow to and/or through the penile arteries caused by an occlusion and/or narrowed vessel lumen. Essentially, penile erection occurs when the two corpora cavernosa fill with blood and maintain internal penile pressure adequate for penetration. Each corpus cavernosum is fed by a deep artery of the penis located in the center of each cavernosum. The deep artery is a branch of the internal pudendal artery that is a branch, and in some cases a direct continuation, of the internal iliac artery, also called the hypogastric artery, which is a terminal branch of the common iliac arteries. The internal pudendal artery feeds most of the external genitalia and perineal structures, wherein the perineum refers to the diamond-shaped area between the thighs from the pubic bone to the tip of the coccyx.

Each deep artery has many smaller coil-shaped arteries, called helicine arteries extending downstream therefrom that open directly into the corpora cavernosa. Erection of the penis is a parasympathetic nervous system process that ultimately results in the release of neurotransmitters and nitric oxide (NO), which results in vasodilation of the helicine arteries in the corpora cavernosa. In addition to dilatation, the helicine arteries also straighten out from their normally coiled configuration to further increase blood flow into the cavernosa. Blood then fills these erectile compartments, and in the process compresses the penile veins that drain these tissues. Subsequent activation of the sympathetic nervous system returns the penis to a flaccid state.

As previously noted, vascular disease occurring anywhere along the arterial path from the abdominal aorta through the internal pudendal artery can adversely affect blood flow to the penile arteries, which in turn may further decrease NO production due to the effect of the decreased blood flow on the endothelium. In many cases, stenting or the performance of another revascularization procedure within the pelvic arterial region might be effective in treating erectile dysfunction caused by vascular disease in some patients, if such treatment of the region was possible and the patient otherwise exhibited normal blood flow within the penis. One of the objectives of increasing blood flow through revascularization of a pelvic artery would be to improve the peak velocity of the inflow of blood into the pelvic arteries and tissues. A rapid inflow will desirably cause the corpus cavernosum to expand rapidly against tunica, hopefully occluding the venous drainage system. This fluid dynamic condition would desirably result in a net increase of blood residing in the penis—and thus an erection.

However, in many patients it may not be possible to restore sufficient blood flow to the penile anatomy using the existing vasculature, even after stenting or the performance of some other revascularization-type procedure. In other patients, revascularization may not be technically feasible (i.e., the constricted vessels may be too small, tortuous and/or inaccessible for a variety of reasons). Still other patients may have comorbidities or other conditions that significantly increase the dangers associated with revascularization (i.e., increased risk or "no option" patients).

In many cases of erectile dysfunction, orally administered selective Phosphodiesterase-5 (PDE-5) inhibitors, such as sildenafil (Viagra), tadalafil (Cialis), and vardenafil (Levitra) have been successful in mitigation some effects of erectile dysfunction, but these drugs do not treat, prevent or cure erectile dysfunction. These drugs work by selectively inhibiting the action of PDE-5, reducing the rate at which cGMP is hydrolized by PDE-5 and thus desirably increasing the concentration and duration of cGMP in the smooth muscle cells and extending the duration of smooth muscle cell relaxation and penile erection. However, while orally administered PDE-5 inhibitors are often effective to allow many suffers of erectile dysfunction to produce an adequate erection for sexual intercourse, the effectiveness of these medications is typically dependent upon the severity of erectile dysfunction and/or any underlying disease. It is commonly accepted that 30-60% of erectile dysfunction sufferers have sub-optimal responses to PDE-5 inhibitors, and in many cases this may be due to the effects of atherosclerotic disease or other vascular conditions which may restrict or diminish blood flow beyond an occlusion and/or stenosis (i.e., in a pelvic or penile artery) to a degree that the patient has insufficient penile blood flow to achieve an erection. Other suboptimal effects of PDE-5 inhibitors may be due to calcification and/or tissue damage to the venous plexus, the tunica albuginea and/or the associated smooth muscle, which can inhibit expansion and/or constriction of the relevant arterial and/or venous structures, reduce nitric oxide elution from vascular endothelium and/or prevent reduction of blood outflow during tumescence. In fact, in many cases the endothelium may become less functional or even nonfunctional due to the decrease in blood flow such that the patient's normal ability to synthesize nitric oxide during arousal becomes impaired. Without the full complement of functional endothelium in the pelvic vasculature (and various supplying vessels), the system may be unable to create sufficient nitric oxide in order to drive the erectile processes. With impaired nitric oxide production (which may be a result of atherosclerosis as well as other conditions), PDE-5 inhibitors may be ineffective or achieve a suboptimal response.

While numerous methods of revascularizing constricted and/or occluded blood vessels could be attempted, such as surgical techniques involving balloon angioplasty, stenting, rotoblading, atherectomy, ultrasonic disintegration, and clot retrieval, these methods are often not technically feasible in much of the pelvic anatomy, primarily because of the narrowness and tortuosity of the numerous vascular channels in this region. Moreover, such procedures are most appropriate for the treatment of discrete locations within the vasculature (which desirably can be transited with revascularizing equipment), rather than for treating more generally degraded and/or obstructed vessels which may be degraded along much of their length. In addition, because erectile dysfunction is not typically a "life threatening" condition, the employment (and surgical risk) of prolonged surgical procedures and/or open surgical techniques to treat such conditions is highly discouraged.

The present technology includes methods, apparatus, and compositions that relate to treating erectile dysfunction in a subject using an angiogenic factor such as FGF-1. Methods of treating erectile dysfunction in a subject can include administering a composition comprising FGF-1 at or proximate to constricted or occluded vasculature and/or at or proximate to ischemic tissue, which could include the corpora cavernosa and/or corpus spongiosum. The angiogenic factor desirably promotes angiogenesis to form new blood vessels and/or extend preexisting blood vessels, which can occur proximate to the vasculature and/or into the ischemic tissue(s).

In one exemplary embodiment, image data can be obtained of an anatomical region-of-interest of a patient, and the image data can be analyzed to identify one or more regions of restricted blood inflow to the patient's penis. Such restriction could be due to an injury or to a buildup of cholesterol or other substances within one or more locations within the anatomy of the patient's vasculature, which can result in insufficient and/or inconsistent blood flow to the penile tissues to initiate and/or maintain an erection. Alternatively, results from a penile function vasoactive or dynamic infusion test may be evaluated. Such vasoactive or dynamic infusion tests can require vasodialating medications to be injected or intravenously pumped into a flaccid penis and/or penile vascular supply vessel to induce a rigid erection. If the quality of the erection is nonexistent, poor or delayed, the penile vasculature may be deemed inadequate or abnormal. The potential for a vessel and/or penile tissue leak can also be analyzed. The severity of the vessel leak, occlusion, and/or restriction can be further determined.

In various embodiments, a method of treating and/or ameliorating the restricted blood flow may include the injection and/or introduction of an angiogenic composition such as FGF-1 into some portion of the patient's anatomy, optionally in combination with other medicaments, which may induce the creation of new vasculature and/or expansion of existing vasculature (which may optionally create new and/or denser blood flow paths and/or a "vascular bypass" and/or parallel conduit to one or more regions of restricted blood flow) to create an overall increase and/or consistency of blood flow to the penis. In various other embodiments, a method of treating and/or ameliorating the identified region(s) of restricted blood flow might include the surgical reduction of blood flow out of the penile tissues, which may include the injection and/or introduction of a vasoconstrictive, occluding and/or blocking agent or composition, such as n-butyl-2-cyanoacrylate (commercially known as VenaSeal adhesive, available from Covidien, LLC of Morrisville, N.C., USA) into one or more vessels of the venous drainage system of the penis, which could create an overall increase of blood retained within the penile tissues.

In various embodiments, the imaging and analysis of vascular perfusion into and/or out of a patient's penis and associated anatomy can be utilized in a variety of ways to identify various causes of erectile dysfunction, as well as assist the physician with identifying and effectuating one or more courses of treatment. In various embodiments, the image data might be analyzed to pinpoint specific tissue regions containing abnormal vasculature that may be contributing to an erectile dysfunction issue, which can allow the physician an opportunity to develop and execute a treatment plan for the patient.

In some embodiments, a treatment plan can include imaging, analysis and identification of abnormal vascular or other tissues within a specific region of the penis and related anatomy, which may be utilized by a physician to plan and execute a course of treatment which isolates and/or minimizes the effects of the abnormal tissue, while optionally increasing and/or maximizing the effects of the remaining healthy and/or less-damaged tissues (i.e., of similar type), which may ultimately restore a desired level of function to the remaining more-normal tissues. For example, imaging and analysis might identify a specific region of the tunica albuginea and related venous plexus (which drains blood from the corpus cavernosum) which is not compressing and/or constricting to a desired degree to reduce penile blood outflow during arousal. This specific region might be more diseased and/or damaged than other regions of the tunica albuginea, and might encompass one or more discrete locations within the penile tissues—for example, a circumferential ring and/or partial ring of calcified and/or diseased tunica albuginea tissue approximately ⅓ up from the base of the penis and about 1" wide along the longitudinal axis of the penis. If desired, a physician might choose to inject and/or introduce a vaso-occluding agent into some or all of this region of damaged tissue, which might alter the hemodynamics of the remaining tissues, bringing them into a more balanced condition and potentially allowing the patient to attain an erection.

In various embodiments, a physician's treatment plan might include a course of treatment that creates an overall improvement to the function of the penile vasculature, but the patient may still not be capable of achieving an erection unassisted. In such a case, the overall improvement may allow the patient to utilize a supplemental medication (i.e., a selective PDE-5 inhibitor) to achieve an erection (or possibly to utilize a lower dose of medication), where prior to the course of treatment, the supplemental medication was ineffective, partially effective and/or unusable. In various other embodiments, the physician's treatment may optionally reduce and/or otherwise alter the penile vascular flow, where the patient may not be capable of achieving an erection unassisted, but such reduction and/or alteration might modify and/or improve the pharmacological effects of a supplemental medication (or might simply amplify the effects of the medication in some manner) to a desired degree such that the patient's subsequent use of a supplemental medication can allow the patient to achieve an erection. In various other embodiments, if a patient was not capable of achieving an erection while taking a prescribed level of a medication (i.e., a medication for treating a non-erectile dysfunction condition such as hypertension) or was in danger of experiencing erectile dysfunction if such a medication level was increased, the physician's treatment might alter the penile vascular flow to a sufficient degree to modify and/or improve the hemodynamic conditions of the penis such that the patient can achieve an erection while taking the prescribed level/increased level of the medication.

In various additional embodiments, imaging and analysis of vascular perfusion of a female patient's vaginal and clitoral vasculature (and related anatomical regions) can be utilized in a variety of ways to identify various causes of female vasculogenic sexual dysfunction, which may similarly assist a physician with identifying and effectuating one or more courses of treatment to ameliorate the condition.

In various additional embodiments, methods of assessing and treating male and female vasculogenic sexual dysfunction can include the steps of imaging and/or assessing an anatomical region-of-interest and related anatomical areas, modeling and assessing the relevant tissue regions, developing a treatment plan and optionally treating the patient to desirably obtain an improved patient condition.

In various embodiments, the assessment of an individual's vascular physiologic processes in an area-of-interest may include non-invasive imaging of the blood flow, vascular structures and/or related tissues within the area-of-interest. Various embodiments may include a variety of imaging modalities and/or data collection techniques, which could include the use of one, two, three or more imaging sessions, as well as the use of extended imaging sessions to desirably collect data regarding changes in vascular flow. For example, non-invasive image data could be obtained for a patient in a non-aroused and/or aroused state, which might include serial imaging of transient vascular effects occurring during the transition from a non-aroused state to an aroused state, if desired—or from an aroused state back to a non-aroused state. Similarly, non-invasive image data could be collected to desirably determine the effects of various medications on a patient's ability to have an erection, which could include imaging of a patient before and/or after they take a medication, which could be accomplished in one, two, three or more imaging sessions, or possibly during a single, extended imaging session, if desired.

The present technology relates to methods of treating erectile dysfunction. Methods include administering a composition comprising an angiogenic factor such as FGF-1 at or proximate to damaged and/or degraded vasculature and/or ischemic tissue (such as, for example, the walls and/or tissue structures of the corpora cavernosa or corpus spongiosum). FGF-1 desirably promotes angiogenesis to provide new blood vessels and/or the extension of preexisting blood vessels to the penile region, which may include ischemic tissue(s). In this manner, tissue defects or vascular disease aspects affecting erectile dysfunction can be treated to provide a long-term therapy or even a permanent effect. In various embodiments, an improved vascularization of the corpora cavernosa or corpus spongiosum can alleviate symptoms of erectile dysfunction and can enhance aspects of other erectile dysfunction treatments, such as administration of vasodilators. In other embodiments, an increased amount and/or density of vasculature and/or microvasculature "upstream" from the penile tissues (potentially created and/or expanded by the various angiogenic treatments described herein) may increase the amount and/or concentration of nitric oxide and/or other chemicals (including those dispensed or eluted by the endothelium cells) for use by the various "downstream" vessels and penile tissues during the erectile cascade, which may allow the patient to achieve and/or maintain an erection. In other embodiments, the creation of new vasculature and/or microvasculature to and/or from the penile tissues might significantly improve the body's ability to "respond" to arousal cues and/or signaling chemicals, in that the newer vasculature/microvasculature will not be as degenerated and/or degraded as the existing vasculature/microvasculature, and thus will be capable of dilation and/or constricting in a desired manner, with attendant improvement in the blood flow and hemodynamics of the penile tissues.

In various embodiments, the present methods can be utilized to diagnose and treat erectile dysfunction caused at least in part by lack of tissue vascularity and/or vessel patentcy. For example, a composition comprising FGF-1 can be injected into a patient at one or more locations proximate to an ischemic tissue region (i.e., tissue regions feeding blood to and/or within the penis) to induce angiogenesis at one or more sites in order to improve blood flow. In various alternative embodiments, the composition can comprise one or more angiogenic factors (including various combinations thereof), which may function in concert to promote the growth of new blood vessels and/or the extension of preexisting blood vessels. Examples of angiogenic factors can include: angiogenin, angiopoietin-1, del-1 protein, fibroblast growth factors such as acidic FGF (also known as aFGF or FGF-1) and basic FGF (also known as bFGF or FGF-2), follistatin, granulocyte colony-stimulating factor (G-CSF), hepatocyte growth factor (HGF), interleukin-8 (IL-8), leptin, midkine, placental growth factor, platelet-derived endothelial growth factor (PD-ECGF), platelet-derived growth factor (PDGF), pleiotrophin (PTN), progranulin, proliferin, transforming growth factor alpha (TGF-α), transforming growth factor beta (TGF-β), tumor necrosis factor alpha (TNF-α), vascular endothelial growth factor (VEGF), and vascular permeability factor (VPF). In various embodiments, isolated, recombinant, and/or synthetic angiogenic factors may be used. Angiogenic factors can be administered to a site of ischemic tissue prior to the administration of other materials, concomitant with administration of other materials, or following administration of other materials to the subject.

In various embodiments, the composition comprising angiogenic factors can be administered at or proximate to penile supply and/or drainage vasculature, as well as directly to ischemic tissues within and/or proximate to the corpora cavernosa or corpus spongiosum, to treat erectile dysfunction in a subject. In this regard, the composition comprising angiogenic factors can be injected into tissues proximate to the ischemic region as well as directly into the ischemic tissue by means of a syringe, such as injection of serial aliquots along the ischemic regions of the penis to stimulate an angiogenic response in situ. Alternatively, the composition can be administered via a surgical procedure, for example using a catheter. The surgical procedure may include an endoscopic surgical procedure. It should be understood, however, that the step of administering the composition of angiogenic factors may employ any biomedically acceptable process or procedure by which the angiogenic factor(s) can be implanted, injected, or otherwise administered in, on, or in proximity to the desired region of interest in a subject so as to have a beneficial effect, such as increasing vascularization by promoting angiogenesis. Increase in blood flow in the area may be one measure of a successful treatment, where the increased blood can lessen the symptoms of erectile dysfunction. Successive administration of angiogenic factors may be used in some cases to more thoroughly vascularize or revascularize the penile region, the blood supply and/or drainage thereof and/or specific ischemic tissue.

As previously noted, the treatment of erectile dysfunction in a patient might create an overall improvement to the function of the penile vasculature, but the patient may still not be capable of achieving an erection unassisted. In such a case, the overall improvement may be combined with other treatments for erectile dysfunction, including alprostadil (Caverject), sildenafil (Viagra), tadalafil (Cialis), and vardenafil (Levitra), which may allow the patient to utilize the supplemental medication to achieve an erection. For example, vascularization or revascularization of the penile blood supply and/or of ischemic tissue of the corpora cavernosa or corpus spongiosum may improve the ability of the subject to develop or maintain an erection. In some cases, the improvement might be further augmented by oral administration of a vasodilator, or it may be possible to reduce the requisite dosing of the vasodilator, which might afford a corresponding reduction in possible side effects.

FIG. 1 depicts the arterial anatomy of the male pelvis. In the male, the aorta (not shown) supplies the common iliac artery 10, which in turn supplies the internal iliac artery 20, which in turn supplies the internal pudendal artery 30, which in turn supplies the common penile artery 40. The common penile artery 40 supplies the bulbourethral artery 50, the dorsal penile artery 60 and the deep penile artery 70. The deep penile artery supplies blood to the corpus cavernosum, while the dorsal penile artery supplies the fibrous sheath of the corpus cavernosum (and sending branches through the sheath to anastomose with the deep artery of the penis).

Figure 2:
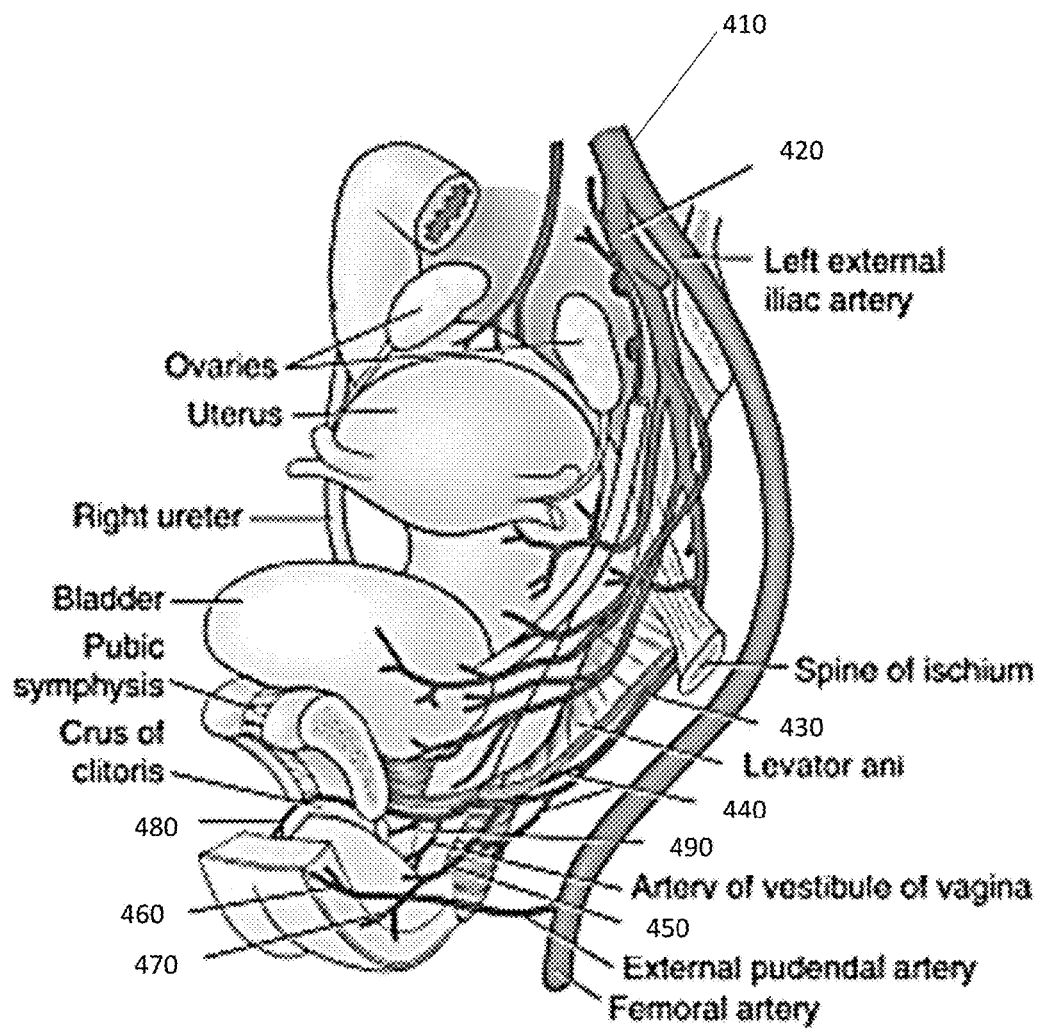
FIG. 2 depicts an exemplary arterial anatomy of a female pelvis.
Figure 3:
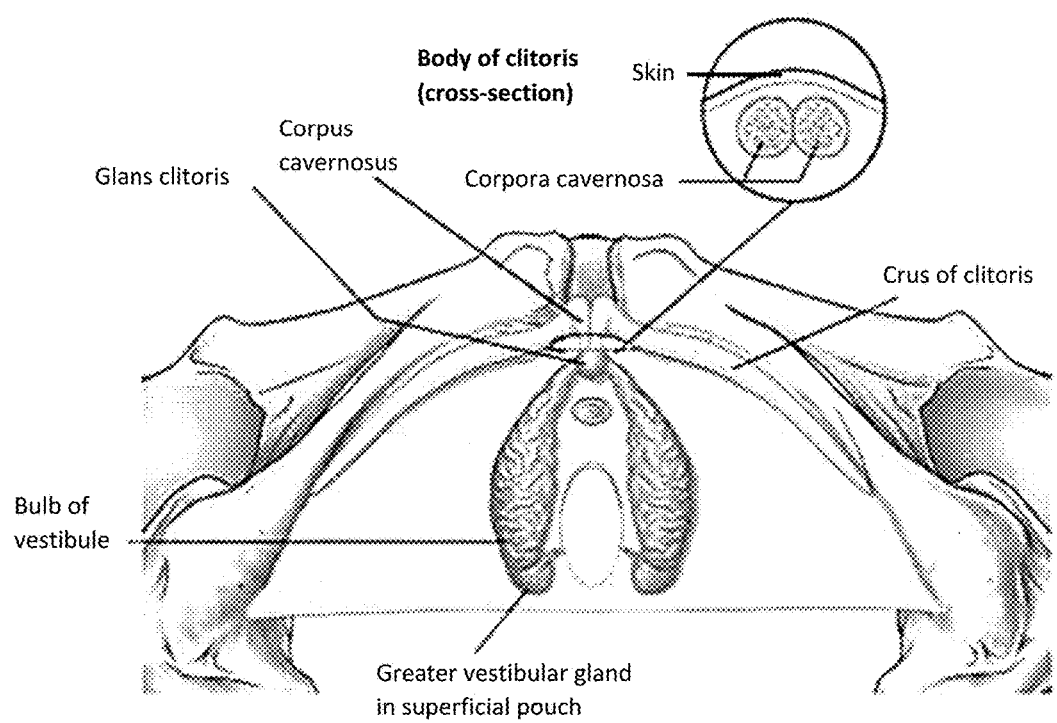
FIG. 3 depicts an exemplary view of a female clitoris and related anatomy.

FIG. 2 depicts the arterial anatomy of the female pelvis. In the female, the aorta (not shown) supplies the common iliac artery 410, which in turn supplies the internal iliac artery 420, which in turn supplies the internal pudendal artery 430. The internal pudendal artery 430 supplies the inferior rectal artery 440, the perineal artery 450, the anterior and posterior labial arteries 460 and 470, the dorsal artery of the clitoris 480 and the deep artery 490 of the clitoris.

Anatomical Imaging of Structural Features and/or Blood Perfusion

Depending upon the specific tissue structure(s) concerned, the diagnosis and/or treatment methods and systems described herein may include the selection and analysis of a plurality of relevant tissue structures. Depending upon the physician's preference and/or the relevant clinical situation, diagnosis of hypoperfusion of some portion of the patient's vascular system might indicate a need for further treatment, as described herein.

The various concepts described herein optionally include the use of image data obtained of a patient's anatomy, which can include non-invasive and/or limited-invasive (i.e., contrast enhanced and/or minimally-invasive) sources of image data of the patient. The various embodiments and concepts disclosed herein also contemplate the use of technologically improved software and/or imaging hardware and systems that can provide high-quality images and/or other data, including those capable of producing high-quality data and/or images with or without the use of contrast injections and/or other exogenous agents, including those developed in the future. In various embodiments, the efficient detection, analysis and diagnosis of vasculogenic erectile dysfunction and/or related conditions and/or other tissue pathologies will typically be dependent upon the quality and resolution of image data acquired of the patient's anatomy. Where the diagnosis is focused on blood flow to a specific region of a patient's pelvis (i.e., the penis or clitoris), the relevant patient image data will desirably include anatomical image and/or perfusion data of the vasculature supply/drainage and/or adjacent anatomical structures, as well as the pelvic structures and any surrounding anatomy, as desired.

It should be understood that, while much of the disclosure herein focuses on the imaging, analysis and/or discussion of male penile and/or pelvic anatomy, the various teachings herein can be utilized with equal utility for the imaging, modeling, analysis, diagnosis and/or treatment of various aspects of female anatomy, including those involving female pelvic anatomy and/or erectile tissues such as the clitoris, while accounting for anatomical variations between the sexes.

A unique challenge posed by various embodiments described herein can relate to unique anatomical features of the particular anatomy of interest. Unlike typical anatomical imaging studies, various regions of interest particularly relevant to the present invention can include image data of vasculature and/or other anatomical structures that may be located adjacent to, which transit and/or which may be at least partially inside of a patient's bones (i.e., pelvic bodies or other bony structures) or other tissues of varying density and/or composition. Unlike the imaging of soft tissues and the outer surfaces of skeletal structures, the differentiation of vasculature adjacent to and/or within skeletal structures can be particularly challenging. Similar issues can be encountered with imaging of fluid and blood flows into, through and/or within bones or other tissues of varying density and/or composition. Moreover, particular locations within and/or adjacent to a given bony structure may be difficult to image, owing at least in part to the density and orientation of relevant and/or adjacent structures.

In an initial step, anatomical image data is obtained of an individual patient's anatomy. This image data can be derived from a wide variety of sources, including MRA (magnetic resonance angiography), MRI (magnetic resonance imaging), x-ray imaging, cone beam CT, digital tomosynthesis, duplex ultrasound, angiography, fluoroscopy, CT scans or PET or SPECT scans. Desirably, image data is obtained that includes the patient's biological structure(s) of interest, which in one exemplary embodiment includes anatomical structures and/or blood flow data of the vasculature supplying to and draining from the penile anatomy—which in various embodiments may specifically be the vascular supply and drainage of one or both of the corpus cavernosa of a patient's penis. For example, pixel or voxel data from one or more radiographic or tomographic images of the patient's anatomy can be obtained using magnetic resonance angiography. Other imaging modalities known in the art such as MRI, ultrasound, laser imaging, PET, SPECT, radiography including digital radiography, digital tomosynthesis or cone beam CT can be used. Contrast enhanced imaging can be employed, if desired.

Desirably, one or more of the pixels or voxels of the image data are converted into one or a set of values. For example, a single pixel/voxel or a group of pixel/voxels can be converted to coordinate values, such as a point in a 2-D or 3-D coordinate system. The set of values could also include values corresponding to the pixel/voxel intensity or relative grayscale color. Moreover, the set of values could include information about neighboring pixels or voxels, such as information that corresponds to a relative intensity or grayscale color and or information corresponding to a relative position.

The image data can be segmented, partitioned or otherwise altered into multiple segments or superpixels. The goal of segmentation is to simplify and change the representation of an image into something that is more meaningful and easy to identify. Image segmentation can be used to locate features and boundaries, such as data corresponding to a particular biological feature of interest. For example, the image data can be used to identify edges of structural features of the pelvic anatomy, such as surface outlines of the sacrum or iliac crest and/or transitions between two adjacent tissue regions. In various imaging systems, a distinctive transition in color intensity or grayscale at a structure's surface can be used to identify pixels, voxels, corresponding data points, a continuous line, and/or surface data representing the surface of the biological structure. These steps can be performed automatically (for example, by a computer program operator function) or manually (for example, by a clinician or technician), or by various combinations of the two.

If desired, segmented data can be combined, such as in a single image including selected segmented and/or identified reference points (e.g., derived from pixels or voxels) and/or other data that can be combined to create a line representing a surface outline of a biological structure. In various embodiments, segmented and/or selected data from multiple 2D image slices can be combined to create a 3D representation of the biological structure. Depending upon the in-plane resolution and slice thickness (which can together define a voxel size, if desired), the field of view, the matrix size and the slice gap, the images can be combined to form a 3D data set, from which the 3D representation of the biological structure can be obtained. In various embodiments, a computer program could be used to load and view 2D images or 3D images and/or could view multiple 2D images as one or more views of 3D image stacks. A series of image slices along one axis and a series of image slices along a second, non-parallel axis could be viewed as separate stacks of 2D images. Stacks of images could result from separate image scans (which can include the use of a single imaging modality along multiple reference planes as well as the sequential imaging of anatomy of interest using different imaging modalities along the same or different planes for each modality) or could be differing views or viewpoints of the same scan. In addition, any two or more images could be combined to provide a 3D image or image approximation.

In various embodiments, the 3D structure of an anatomical feature can be derived directly using a 3D segmentation technique, for example an active surface or active shape model algorithm or other model based or surface fitting algorithm. Alternatively, a 3D representation of the biological structure could be generated or manipulated (i.e., corrected or smoothed) by employing a 3D polygon surface, a subdivision surface or a parametric surface such as a non-uniform rational B-spline surface. Various methods are available for creating a parametric surface, which can include converting the 3D representation directly into a parametric surface by connecting data points to create a surface of polygons and applying rules for polygon curvatures, surface curvatures, and other features.

In one alternative embodiment, a template model could be applied to approximate and identify a biological feature or could be applied directly to an image data array. For example, an iliac crest body template and/or penile structure body template could be applied to an image data file and/or subsequently segmented image data. In applying a template model, the operator, user or the software itself could select one or more initial best fit template models. Template models of relevant anatomical structural features can be obtained from a library of models or other publicly available sources.

Obtained anatomical image data can include points, surfaces, landmarks and/or other features, which can collectively be referred to as "reference points." In certain embodiments, the reference points can be selected and/or identified by an automated program or manually by an operator and used to identify an anatomical feature and/or region of interest. For example, reference points from an anatomical image of the pelvis can be used to identify particular anatomical features of the pelvis, such as the various pelvic bones, connective tissues and vasculature such as the aorta, which in turn can be used to identify one or more specific regions of interest of the image data for further analysis. If desired, reference points can be grouped to form reference structures and/or surfaces, including triangles, polygons, or more complex surfaces such as parametric or subdivision surfaces.

Once the appropriate pelvic anatomy is identified, one or more regions of interest in the image data will desirably be identified. For example, if a pelvic bone, relevant penile tissues and the major supply and drainage vasculature can be identified from the segmented data, the relative location(s) of the minor and microvascular vessels/microcirculation may be identified and assigned or "bounded" as one or more regions of interest (ROI) of the image data. This ROI can be analyzed in a variety of ways, and the analysis results can be compared to a defined value and/or standard (and/or can be displayed and/or assessed using a value "map" of ROI(s) in 2D or 3D space) and utilized to diagnose, assess and/or quantify pathology. If desired, the analysis and diagnosis can be used for modeling of the hemodynamics of the penile system and/or as guidance for treating the patient.

Vascular, Perfusion and Diffusion Imaging

In various embodiments of the invention, diffusion studies (Diffusion Weighted images or DWI) could be performed for analyzing various diffusion characteristics of the penile vasculature and correlating it to vascular hypoperfusion, hemodynamic imbalance, erectile dysfunction and/or arterial/venous stenosis. In other embodiments, perfusion studies can be performed using methods such as Dynamic Contrast Enhanced MR Imaging for analysis of perfusion of various vessels and/or the pelvic/penile anatomy.

Diffusion and Other Studies

Diffusion Weighted Images (DWI) may be helpful in delineating benign and malignant conditions that might affect erectile dysfunction, and may also be useful to some degree in analyzing the blood flow and/or diffusion characteristics of the penile anatomy and correlating it with erectile dysfunction, vessel stenosis and/or perfusion abnormalities. Analyzing diffusion properties among various patient populations (as well as normal controls) may lead to data that can contribute to an accurate erectile dysfunction diagnosis.

DCE-MRI and Other Techniques

Dynamic Contrast Enhanced MR Imaging for analysis of perfusion of the pelvic anatomy can include using a 1.5 Tesla scanner to evaluate a potential for hemodynamic imbalance resulting in and/or leading to erectile dysfunction and/or other diagnoses. However, higher powered imaging equipment, such as 3 Tesla or higher scanners, may significantly improve the accuracy and resolution of image data, which can be particularly useful in imaging and assessing the minor vessels and/or microcirculation proximate to the penile anatomy. In one exemplary embodiment, imaging parameters for a 3 Tesla scanner were developed to facilitate the acquisition of useful microcirculation image data. Other systems could be used, if desired, including those that employ the use of high-field magnets due to their higher SNR (signal to noise) and CNR (contrast to noise) ratios in comparison to lower strength magnets. Such systems could potentially allow a lower dose of contrast material to be delivered to the patient yet allow generation of an equivalent image quality to those of lower-field magnets with a higher dose of contrast. Such a system may also permit the use of serial (multiple) bolus contrast injection for multiple scanning sequences of the patient, potentially using different scanning techniques and/or modalities. The use of higher strength systems, including those with 7-10 Tesla magnets, may improve the resolution and accuracy of scanning, including the potential to directly image the vessels, lesser vessels and/or microvasculature. If different imaging techniques are to be employed, it may be desirous to complete any non-contrast imaging initially, and then subsequently perform contrast-assisted imaging, to reduce the potential for imaging errors and/or artifacts caused by the contrast and/or its remnants during the non-contrast imaging techniques.

For imaging protocols in one exemplary embodiment involving microcirculation within and/or adjacent to a bony structure, the following could be used in conjunction with a Philips Achieva 3T system: 330 mm×300 mm FOV and a 6-element SENSE torso RF coil. The imaging session can be started with the perfusion scan following the standard calibration scans. A 3D FFE sequence with TR/TE=3.5 ms/1.5 ms, SENSE factor: 2.5(AP), 2(RL), flip angle=30°, with dynamic scan time of 2.9 s was used and 7 slices in sagittal orientation with 6 mm thickness and 1.9 mm×1.9 mm pixel size were acquired. A total of 114 volumes were collected, 2 of them before contrast injection. After the dynamic scans, T1 weighted anatomical images in sagittal plane were collected using a TSE sequence with 0.5×0.5×3 mm$^3$ voxel size. 14 slices cover the same volume as dynamic scans. TR/TE=900 ms/10 ms, flip angle=90°. This was followed by a T2 weighted scan that had identical geometry to T1 scans and TR/TE=2940 ms/120 ms, flip angle=90°. Finally, contrast-enhanced angiography scans were collected. Contrast bolus arrival was observed real-time using a single, 50 mm thick coronal slice using FFE sequence in dynamic mode, collecting images every 0.5 s. Once the contrast arrived in the descending aorta, actual 3D angiography scan was started by the operator immediately. TR/TE=5.1 ms/1.78 ms, voxel size=0.8*0.8*1.5 mm$^3$, with SENSE factor=4 was used to acquire 50 coronal slices. Segmental vessels on MRA were graded as occluded, stenotic or open. Soft tissue structures were graded as per Pfirrmann (Pfirrmann, C. et al, *Spine* 26:1873-1878, 2001). ROI-averaged time course (from whole vertebra and/or end-plate structures) was converted into a fractional enhancement time course and analyzed using a compartmental model (Larsson, et. al. *MRM* 35:716-726, 1996; Workie, et. al. *MRI*, 1201-1210, 2004). The model fitting results in 6 parameters: Ktrans' (apparent volume transfer constant), kep (rate constant), Vp' (apparent fractional plasma volume), E (extraction fraction), tlag (arrival time of tracer in the ROI) and baseline.

In one alternative exemplary embodiment, a high spatial resolution version of DCE-MRI could include a 3D gradient echo-based sequence with TR/TE=3.4/1.2 (ms), flip-angle=30°, reconstructed voxel-size=0.8×0.8×3 mm$^3$, temporal-resolution (or dynamic scan time)=36.4 sec w/22 dynamic frames (volumes). The entire bolus of contrast could be utilized for the DCE-MRI, which was preferable for this embodiment, or the contrast can be given in two boluses, one for DCE-MRI and one for MRA. Other non-contrast scans (i.e., T1 and T2w) could employ the same or similar acquisition parameters as described above, with non-contrast imaging desirably preceding contrast-assisted imaging where possible.

Data can be collected from control and experimental subjects to ascertain an "ischemic index" of the pelvic vasculature, which could desirably be applied to future assessments of vasculogenic erectile dysfunction and/or other related conditions. The data can be correlated with the degree of tissue degeneration, hemodynamic dysfunction and/or the degree of vessel stenosis to define a new clinical entity and the proper imaging tools for diagnosis of hemodynamic imbalances of the pelvic region, particularly erectile dysfunction. Since perfusion analysis can potentially measure the amount of blood supply coursing through the penis and the pelvic anatomy and microvasculature thereof, this value could be important in developing treatment schemes based on improving the blood supply to the penis.

In various embodiments, perfusion measurement and assessment via DCE-MRI or other imaging modalities could be performed at almost any vascular level, including at major vessel level and/or down to the capillary level, especially in terms of 'high spatial resolution' type DCE-MRI. Such scans could potentially differentiate where contrast material might potentially "leak out" and accumulate in extravascular, extracellular-matrix (ECM) space, and could also measure where and/or if the contrast material eventually "cleared out" of the ECM, given a sufficient scan duration. This could significantly improve the ability to image and resolve the actual blood flow in the pelvic vessels as compared to imaging of the exchange between the 'vascular' space (i.e., capillary) of interest and the ECM space (which may be of lesser interest, depending upon the surgeon's preference). For example, if the imaged contrast-material were of the intravascular type (i.e., it does not easily leak out from 'normal' capillaries), the level of detectable signal 'enhancement' that could be measured during DCE-MRI scanning might be very low because of the relatively small percentage that might be considered as 'vascular space' in a typical imaging voxel-size for most biological tissue.

Similar differentiation of such extravascular and/or extracellular presence of contrast (i.e., Omniscan: Gd-DTPA-BMA) could be possible with contrast material used in other imaging modalities, including imaging modalities such as CE-MRI. If desired, the assessment of blood supply or flow into such vascular networks could also be evaluated 'upstream' (i.e., in larger arteries and/or blood supply vessels of any size) and/or "downstream" (i.e., in veins and/or other drainage vessels of any size) as part of the imaging and assessment process herein.

In various embodiments, the use of combinations of CE-MRA and DCE-MRI in the same MRI or in a sequential scanning session could be performed. While CE-MRA can be combined w/CE-MRI, CE-MRA may not provide a desired level of 'quantitative' information to the surgeon as compared to an equivalent DCE-MRI imaging session. In such situations, the use of higher strength magnet systems could desirably allow the injection of reduced doses of contrast for such serial imaging, thereby allowing for the collection of greater amounts and/or resolutions of data (which can be combined post-imaging, if desired) than that of a single imaging modality alone.

In various alternative embodiments, the use of intravascular contrast material might be preferred, as this material may not lend itself to diffusion from the vasculature, but such use could also be limited in its imaging of diffusive patterns from the vascular network through the pelvic and/or penile tissues. In contrast, the use of easily diffusing contrast, in combination with the ability to differentiate leaking contrast versus intravascular contrast, could potentially facilitate direct imaging of flow patterns and vasculature structure, while ignoring or discounting such contrast potentially in the (ECM) space.

Pelvic MR Spectroscopy and Other Studies

A loss of perfusion in the pelvic and/or penile vasculature can result in less oxygen, nutrients and/or NO available for vascular and/or penile tissues. Loss of oxygen (hypoxia) can result in various tissues shifting to anaerobic metabolism to produce energy, and chronic ischemia may also be involved in the deterioration of cavernosal smooth muscle, endothelial cells and/or in the development of corporeal fibrosis, which may in turn lead to erectile dysfunction. In many tissues, shifting to anaerobic metabolism can be associated with a shutdown in matrix production and resulting poor matrix repair and maintenance. High field strength spectroscopy (which is desirably of at least 3 Tesla strength, although lesser or greater strengths may be used with varying levels of utility) may be extremely important in the delineation of metabolic abnormalities associated with ischemia within the pelvic and/or penile anatomy. It has been demonstrated that lactate levels are elevated in various tissues dependent upon anaerobic metabolism. Therefore, lactate or other "markers" of anaerobic metabolism could potentially be used as a biochemical marker signifying an anatomical region (i.e., various penile tissues) that is "stressed" and at risk. In addition, low pH (associated with high lactate) has been demonstrated to be a biochemical mediator of various tissue pain. Other useful markers that may correlate with ischemia/hypoxia and painful, degenerative tissues include, but are not limited to, determination of 31P levels as an indicator of energy level, water content as an indicator of proteoglycan content and tissue structure size. An enlarged tissue structure can indicate less efficient distribution of oxygen and an increase in anaerobic metabolism.

For example, in intervertebral disc tissues, hallmarks of disc degeneration can include loss of proteoglycans, water, and Type II collagen in the disc matrix, and similar detectable indicators may be produced by degenerating vascular and/or penile tissues. Other changes in the matrix are less well defined, including loss of the higher molecular weight proteoglycans, collagen cross-linking and organization of the proteoglycan, etc. An important process in disc degeneration appears to be the change of the differentiated chondrocyte phenotype in the nucleus pulposus into a more fibrotic phenotype. Together these changes in the disc matrix lead to alterations of the disc and vertebral anatomy that ultimately are associated with a pathologic condition. Even though the turnover rate of PG's may be very long, longitudinal imaging can be an excellent method of quantification of chondrocyte recovery and return to synthetic function. PG is negatively charged and it has been determined that the tissue integrity can be preserved by maintaining a fixed charge density in cartilage. Sodium ions, which are positively charged, are attracted by this fixed charge density. The sodium content of cartilage can be correlated with its fixed charge density, hence the PG content. With proper imaging protocols, the measured sodium signal can be directly correlated with PG content and negatively correlated with T1 and bi-exponential T2 values. Accordingly, in at least one exemplary embodiment, such sodium (or other chemical) imaging can potentially be utilized as a marker for tissue degeneration in other non-spine regions, such as the pelvic and/or penile anatomy.

In one exemplary embodiment involving disc tissues of the spine, proteoglycan quantification could be measured in vivo using a MRI imaging technique called T1rho (T1ρ) sequence. Just as ADC value (ADC-mapping) can be a quantitative outcome of diffusion-weighted imaging (DWI), T1ρ relaxation time (T1ρ mapping) can be an outcome of T1ρ weighted imaging wherein the relaxation time is shown to be directly correlated to PG (proteoglycans) content. Relevant data obtained could be used by a clinician to identify the hallmarks of tissue degeneration, including the loss of proteoglycans, water, Type II collagen and/or other changes in the tissue matrix, and recommend further analysis, imaging and/or treatment including the various techniques described herein.

Penile Sonography

Penile sonography may be performed to show diminished arterial and venous blood flow. For example, duplex Doppler sonography may be used to evaluate the patency of the cavernosal arteries and competency of the penile veins and using gray-scale real-time sonography to assess the corporal architecture.

Several parameters may be collected to quantify penile blood flow in the cavernosal arteries and/or deep dorsal veins. These parameters could include one or more of: acceleration, peak flow systolic and end-diastolic velocity, arterial dilatation, cavernosal arterial diameter, visible pulsatility of the cavernous artery, increase of penile volume, and resistance index. Such parameters may be useful when comparing before and after intracorporal injection of vasoactive medications to induce an erection.

Combination Imaging Strategies

In various embodiments, combinations of imaging strategies and/or methodologies can be employed to collect image data. In various embodiments, the various image data types obtained can be used for generation of algorithms to include/exclude patients for the treatment of erectile dysfunction and/or other pathologies, and identify "at risk" tissues, including those suffering from vascular and/or diffusive deficiencies and/or structural deficits. Combining imaging studies may provide important insight into the description of heretofore unknown vascular diseases of the pelvic region, penile region and/or other joints and tissues. In one embodiment, the clinician treating patients with erectile dysfunction may recommend longitudinal DCE-MRI for analysis of penile tissue perfusion along with Ti☐ and ADC. These studies could show a correlation of accelerated detrimental changes within the penile tissues that, coupled with an association with hypoperfusion and/or ischemia of the penile tissues, may satisfy one or more inclusion criteria for treatment of the relevant vascular channels with angiogenesis. This static image combination could provide important clinical information that leads to medically necessary treatment protocols. In addition, combinations of image techniques might be utilized—i.e., multiple different imaging modalities within a short time period and/or multiple imaging modalities over time using complimentary, serial modalities for analysis. A clinical treatment plan could also be developed based upon the results of the multiple/serial imaging acquisitions.

Penile Tissue Imaging Considerations

Figure 4:
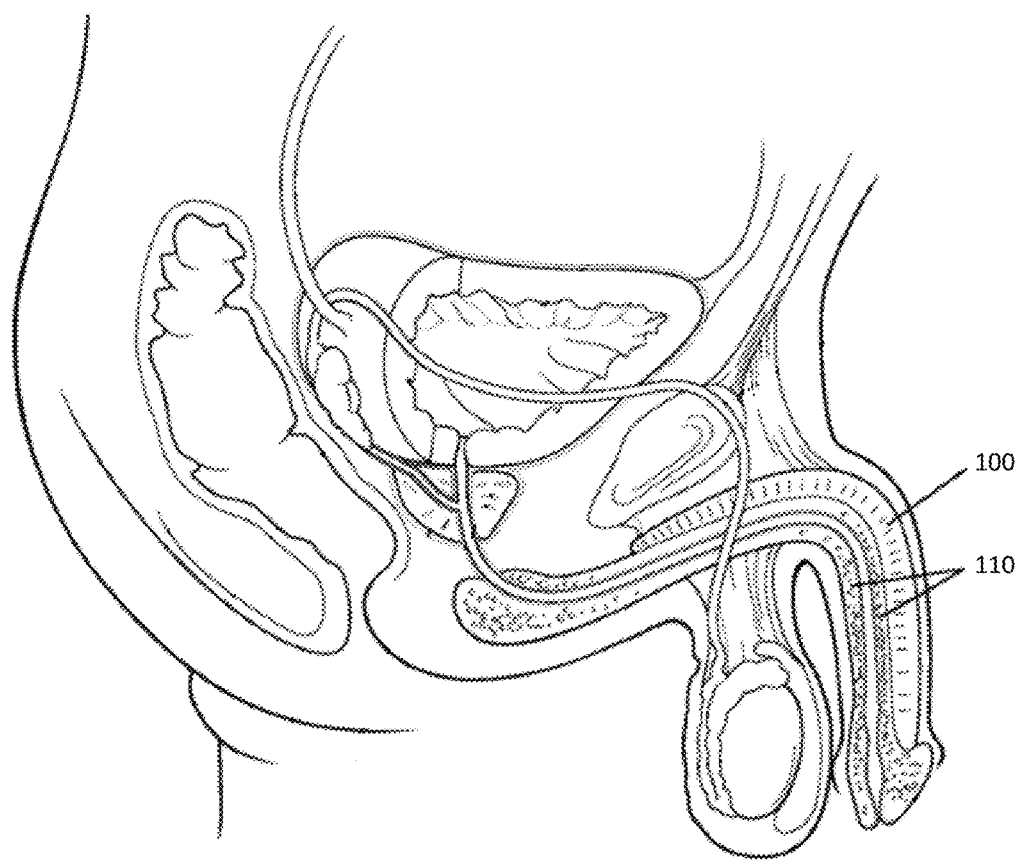
FIG. 4 depicts a cross-sectional view of a male pelvis and related anatomy.
Figure 5:
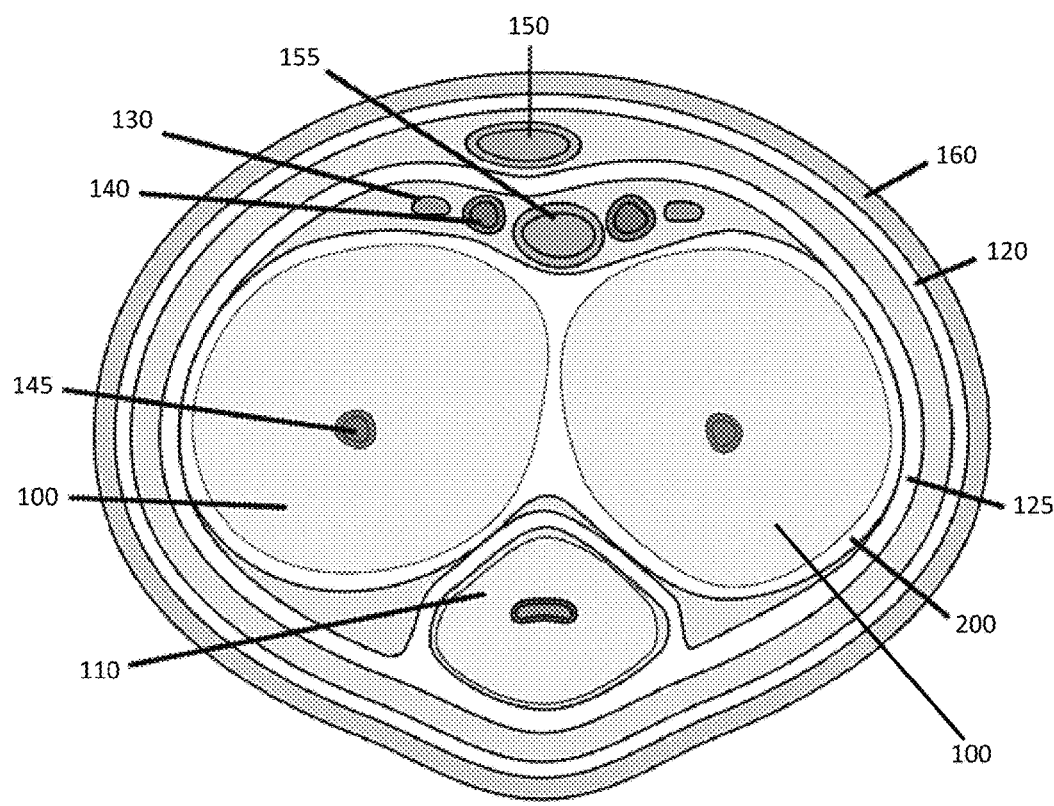
FIG. 5 depicts a cross-sectional view of a male penis showing the three erectile columns.

As best seen in FIGS. 4 and 5, the penile shaft is composed of 3 erectile columns, the two corpora cavernosa 100 and the corpus spongiosum 110, as well as the columns' enveloping fascial layers (i.e., the Dartos or superficial fascia 120 and the Buck's or deep fascia 125), nerves 130, lymphatics, arteries 140, 145, and veins 150, 155, all covered by skin 160. Two suspensory ligaments, composed of primarily elastic fibers, support the penis at its base. The paired corpora cavernosa 100 contain erectile tissue and are each surrounded by the tunica albuginea 200, a dense fibrous sheath of connective tissue with relatively few elastic fibers. The corpora cavernosa 100 communicate freely through an incomplete midline septum. Proximally, at the base of the penis, the septum is more complete; ultimately, the corpora diverge, forming the crura, which attach to the ischiopubic rami.

The tunica albuginea 200 consists of 2 layers, the outer longitudinal and the inner circular. The tunica albuginea becomes thicker ventrally where it forms a groove to accommodate the corpus spongiosum. The tunica albuginea of the corpus spongiosum is considerably thinner (<0.5 mm) than that of the corpora cavernosa (approximately 2 mm). Along the inner aspect of the tunica albuginea, flattened columns or sinusoidal trabeculae composed of fibrous tissue and smooth muscle surround the endothelial-lined sinusoids (cavernous spaces). In addition, a row of structural trabeculae arises near the junction of the 3 corporal bodies and inserts in the walls of the corpora about the midplane of the circumference.

The erectile tissue within the corpora contains arteries, nerves, muscle fibers, and venous sinuses lined with flat endothelial cells, and it fills the space of the corpora cavernosa. The cut surface of the corpora cavernosa looks like a sponge. There is a thin layer of areolar tissue that separates this tissue from the tunica albuginea.

Tunica Albuginea

The tunica is composed of elastic fibers that form an irregular, latticed network on which the collagen fibers rest. The tunica albuginea is composed of an inner circular layer and an outer longitudinal layer. Emissary veins travel between the inner and outer layers of the tunica and often exit the outer layer in an oblique manner. During arousal and the initial stages of the erectile cascade, the outer layer of the tunica desirably compresses the emissary veins when the penis becomes engorged with blood.

Corpora Cavernosa

The corpora cavernosa are 2 spongy cylinders. Within the tunica albuginea are the interconnected sinusoids separated by smooth muscle trabeculae and surrounded by elastic fibers, collagen, and loose areolar tissue. The terminal cavernous nerves and helicine arteries are intimately associated with smooth muscle. The sinusoids are larger in the center and smaller in the periphery.

Corpus Spongiosum

The structure of the corpus spongiosum is similar to that of the corpora cavernosa, except that the sinusoids are larger and a much thinner outer layer of the tunica albuginea is present. The glans has no tunical covering.

Erectile Tissue Vessels

The helicine arteries, branches of the deep penile artery, supply the trabecular tissue and sinusoids. They are contracted and tortuous in the flaccid state and dilated and straight in the erect state. The venous drainage from the erectile tissue originates in the venules starting at the peripheral sinusoids beneath the tunica albuginea. They travel in the trabeculae between the tunica and the peripheral sinusoids, forming the subtunical venular plexus before exiting as the emissary veins.

Penile Skin

The penile skin is continuous with that of the lower abdominal wall. Distally, the penile skin is confluent with the smooth, hairless skin covering the glans. At the corona, it is folded on itself to form the prepuce (foreskin), which overlies the glans. The subcutaneous connective tissue of the penis and scrotum has abundant smooth muscle and is called the dartos fascia, which continues into the perineum and fuses with the superficial perineal (Colle) fascia. In the penis, the dartos fascia is loosely attached to the skin and deep penile (Buck) fascia and contains the superficial arteries, veins, and nerves of the penis.

Penile Blood Supply

The blood supply to the penis is provided by a large number and variety of vessels that supply and drain the various penile components. Blood supply to the skin of the penis is from the left and right superficial external pudendal arteries, which arise from the femoral artery. The superficial external pudendal arteries branch into dorsolateral and ventrolateral branches, which collateralize across the midline. In addition, branches in the skin form an extensive subdermal vascular plexus.

Figure 6:
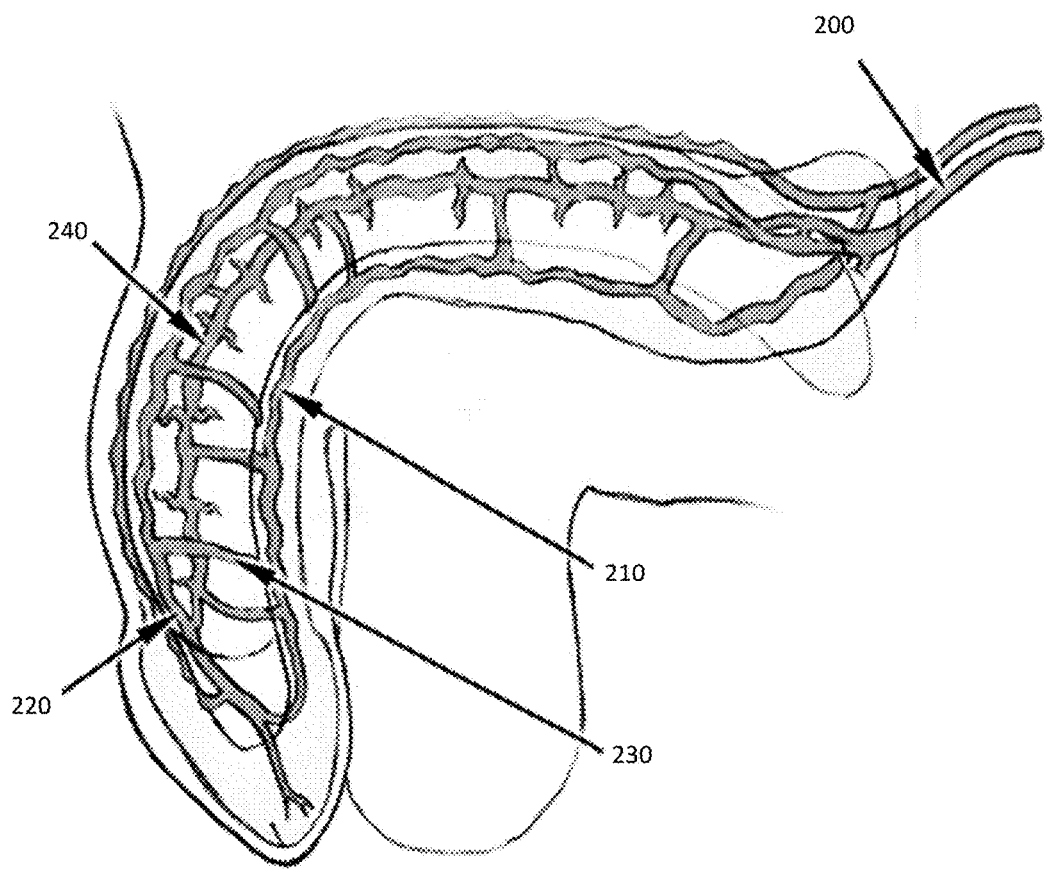
FIG. 6 depicts the major arterial blood supply conduits in the penis.

As best seen in FIG. 6, the blood supply to deep structures of the penis is derived from a continuation of the internal pudendal artery 200, after it gives off the perineal branch. Three branches of the internal pudendal artery flow to the penis, as follows:

(1) the artery of the bulb (bulbourethral artery) 210 passes through the deep penile (Buck) fascia to enter and supply the bulb of the penis and penile (spongy) urethra;

(2) the dorsal artery 220 travels along the dorsum of the penis between the dorsal nerve and deep dorsal vein and gives off circumflex branches 230 that accompany the circumflex veins; the terminal branches are in the glans penis; and (3) the deep penile (cavernosal) artery 240 is usually a single artery that arises on each side and enters the corpus cavernosum at the crus and runs the length of the penile shaft, giving off the helicine arteries, which are an integral component of the erectile process.

Penile Blood Drainage

Figure 7:
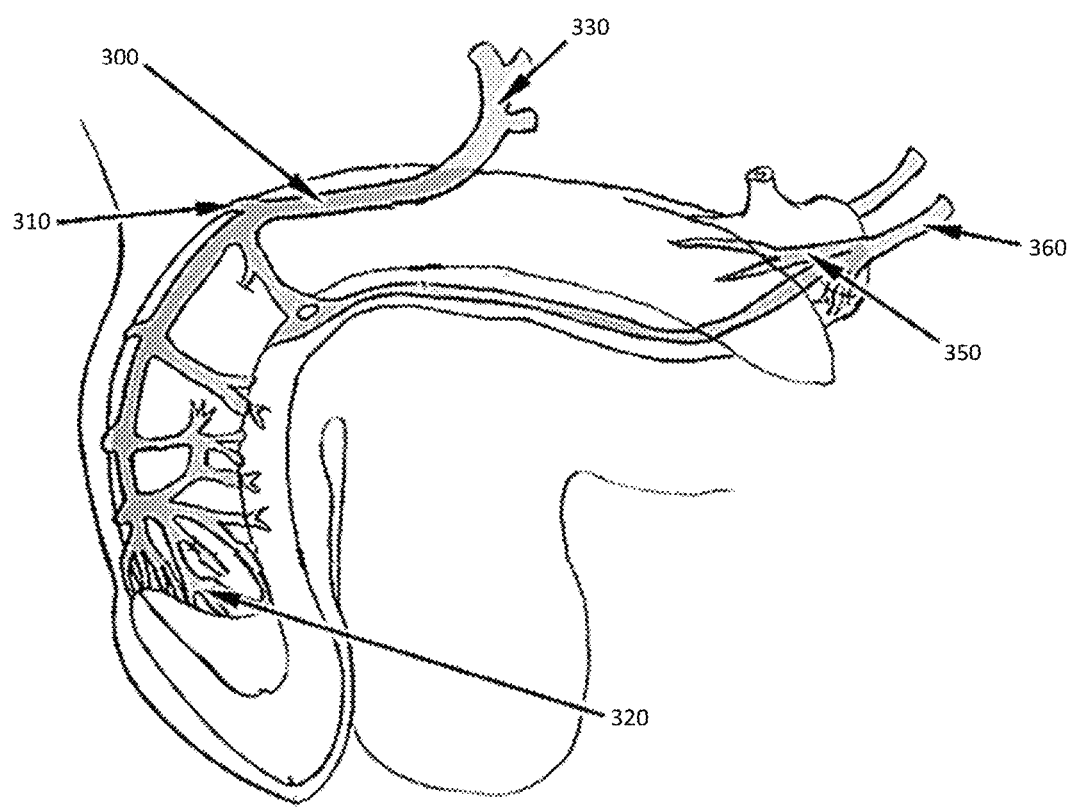
FIG. 7 depicts the major venous blood drainage conduits in the penis.

As best seen in FIG. 7, the penis is drained by three venous systems, the superficial, intermediate, and deep. Superficial veins are contained in the dartos fascia on the dorsolateral surface of the penis and coalesce at the base to form a single superficial dorsal vein, which usually drains into the great saphenous veins via the superficial external pudendal veins.

The intermediate system contains the deep dorsal vein 300 (which can occasionally be more than one vein) and the circumflex vein 310, lying within and beneath the deep penile (Buck's) fascia. Emissary veins begin within the erectile tissue of the corpora cavernosa and course through the tunica albuginea and drain into the circumflex or deep dorsal veins. The circumflex veins arise from the spongiosum, ventrum of the penis, and often, the emissary veins drain into them.

The circumflex veins course laterally around the cavernosa, passing beneath the dorsal arteries and nerves and drain into the deep dorsal vein 300. The deep dorsal vein 300 lies in the midline groove between the 2 corpora cavernosa and is formed from five to eight veins emerging from the glans penis, forming the retrocoronal venous plexus 320. It receives blood from the emissary and circumflex veins and passes underneath the symphysis pubis at the level of the suspensory ligament, leaving the shaft of the penis at the crus and draining into the periprostatic plexus 330.

Deep venous drainage is via the crural vein and cavernosal veins 350. The crural veins arise in the midline, in the space between the crura. The cavernosal veins 350 are consolidations of the emissary veins, which join to form a large venous channel that drains into the internal pudendal vein 360. Three or four small cavernosal veins course laterally between the corpus spongiosum and the crus of the penis for two to three centimeters before draining into the internal pudendal veins 360.

Blood flow to the corpora cavernosa is via the paired deep arteries of the penis (cavernosal arteries), which run near the center of each corpora cavernosa. The single corpus spongiosum lies in the ventral groove between the 2 corpora cavernosa. The urethra passes through the corpus spongiosum. The corpus spongiosum possesses a much thinner and more elastic tunica albuginea to allow for distention of the corpus spongiosum for passage of the ejaculate through the urethra. The thinner tunica albuginea of the corpus spongiosum also allows the corpus to become less rigid during erection. Hence, the distal extension of the spongiosum, the glans penis, covers the tips of the corpora cavernosa to provide a cushioning effect. The urethral meatus is positioned just slightly on the ventral surface of the glans and is slit-like. The edge of the glans overhangs the shaft of the penis, forming a rim called the corona.

The 3 erectile bodies are surrounded by deep penile (Buck's) fascia 125, the dartos fascia 120, and the penile skin 160. The deep penile (Buck's) fascia is a strong, deep, fascial layer that is immediately superficial to the tunica albuginea. It is continuous with the deep fascia of the muscles covering the crura and bulb of the penis, the ischiocavernosus and bulbospongiosus.

On the dorsal aspect of the corpora cavernosa, the deep dorsal vein and paired dorsal arteries and branches of the dorsal nerves are contained within the deep penile (Buck's) fascia. This fascia splits to surround the corpus spongiosum, and it extends into the perineum as the deep fascia of the ischiocavernosus and bulbospongiosus muscles. The deep penile (Buck's) fascia encloses these muscles and each crus of the corpora cavernosa and the bulb of the corpus spongiosum, adhering these structures to the pubis, ischium, and the urogenital diaphragm.

Anatomical Variations

One significant complicating factor in imaging and analyzing the blood supply of the male penis (and similarly with respect to female anatomy) is the existence of a significant amount of anatomical variation that can be found in the pelvic region of the male population. While in most cases the largest vasculature of the pelvic region will be generally consistent between individuals, the same is not true for the various arterial and venous vessel branching patterns, collateral and accessory vessels, and remaining vascular anatomy of the pelvic region. For example, the obturator artery (sometimes referred to as the inferior gluteal artery) will often be a collateral branch of the internal iliac artery, but in at least ⅓ of individuals the obturator artery will have its origin from the epigastric artery (from the external iliac artery). Moreover, even where the obturator artery is in its most common position as a collateral branch of the internal iliac artery, the obturator artery can originate from the anterior common (anterior) gluteal-pudendal truck (50% of the time), from the posterior (common gluteal) trunk (10% of the time), from the internal pudendal artery (10% of the time), from the inferior gluteal artery (10% of the time), from the superior gluteal artery (10% of the time), or directly from the internal iliac artery (7% of the time). In addition, the effects of atherosclerotic changes (and/or other disease states), prior injuries and/or surgeries, natural healing responses and/or scarification can create significant vascular supply and/or drainage variation between individuals.

In order to properly assess the hemodynamics of pelvic blood flow for a given individual, in various embodiments a set of comprehensive vascular images and/or perfusion data for the entire pelvic region of a patient can be obtained, with the image data analyzed and/or assessed to obtain data regarding the arterial (or other) blood inflow and venous (or other) blood outflow of the penile tissues. This image data might be obtained from the patient during a plurality of penile states, which may include a non-aroused state and/or an aroused state, if desired. Once the blood inflow and outflow data has been determined, the relative flow values can be compared and an objective hemodynamic assessment of the patient's condition may be performed.

In various exemplary embodiments, the assessment results may indicate one or more abnormalities in penile blood flow that may be indicative of erectile dysfunction or other conditions, which could include being an early indicator of atherosclerosis, heart disease, peripheral artery disease and/or other conditions potentially affecting other regions of the patient's anatomy. In many cases, an underlying cause of erectile dysfunction is the deterioration and/or degeneration of the vascular conduits to, from and/or within the penile tissues, as well as degeneration and/or damage to related tissues of the penis itself. Often, a patient will experience various combinations of one or more of the following: impaired blood circulation, reduced nutrient flow, reduced oxygenation of tissues, poor cellular waste transport, vessel calcification, poor blood flow in and/or adjacent to the penile tissues, degeneration of the vessels and associated tissue structures such that they inhibit dilation and/or constriction of vessel/tissue structures during normal erectile behavior and/or loss of erectile enzymes and/or signaling molecules. Moreover, while erectile dysfunction does not seem of great concern at a first glance, the condition strongly correlates to underlying systemic conditions affecting numerous vessels and other tissue structures within the body, including those supplying nutrients to the heart, lungs, brain, major organs and extremities. For example, for men aged 45 and up without diagnosed heart disease, those with moderate or severe erectile dysfunction are up to 50% more likely to be hospitalized for heart problems. This same group is 8 times more likely to suffer heart failure, is 60% more likely to have heart disease and is almost twice as likely to die of any cause. In various embodiments, therefore, imaging and analysis of the pelvic region and/or penile tissues and/or vasculature may predict and/or signal a variety of undiagnosed disease conditions, including those that affect other areas of the body such as the heart, major organs and extremities.

Desirably, once a dysfunctional erectile condition has been established (or a likelihood thereof exists), the image data can be further interrogated and/or analyzed to identify potential "sources" of the condition, which may include constrictions and/or occlusions in one of more supply vessels and/or microvasculature, excessive and/or restricted flow patterns out of drainage vessels, damaged and/or malfunctioning anatomical features and/or systems that contribute to the hemodynamic imbalance and/or various combinations thereof.

Depending upon the cause and/or severity of the hemodynamic imbalance, it may be possible to address the condition in a variety of ways. For example, where the imbalance is at a lesser level, it may be desirable to correct, reduce and/or otherwise acceptably manage the imbalance by life style changes such as diet, exercise and/or reduction of alcohol or tobacco. For moderate imbalances, it may be advisable to address the imbalance pharmacologically (which may include adding medication, altering an existing medication "mix" and/or reducing, changing or eliminating a medication currently taken by the patient). For severe imbalances, correcting, reducing and/or otherwise acceptably managing the imbalance may require more aggressive interventions, including surgical corrections.

For example, in one exemplary embodiment a set of comprehensive vascular images and/or perfusion data for a significant portion of a patient's pelvic region can be obtained, with the image data analyzed and/or assessed to obtain data regarding the arterial blood inflow to the penis (i.e., via the major penile arteries). In some embodiments, a comparison between the arterial penile inflow during a flaccid state and an aroused state for the patient can be conducted, with a potential diagnosis of vasculogenic hemodynamic imbalance where the aroused flow is less than between 25 to 60 times the flaccid flow. In various other embodiments, the inflow number can be charted to determine whether the inflow is normal or abnormal, such as identified below:

| AVERAGE MEASURED PENILE INFLOW RATE AT AROUSAL | | | |
| --- | --- | --- | --- |
| NORMAL | MARGINAL | LOW | ABNORMAL |
| >20 ML/MIN | 20-12 ML/MIN | 12-7 ML/MIN | <7 ML/MIN |

As another measure of penile inflow, a measurement of the velocity of the penile blood flow might be obtained, such as follows:

| AVERAGE MEASURED PENILE INFLOW VELOCITY AT AROUSAL | | |
| --- | --- | --- |
| NORMAL | MARGINAL | LOW/ABNORMAL |
| >40 CM/SEC | 40-30 CM/SEC | <30 CM/SEC |

In a similar manner, the venous blood outflow could be determined using the vascular image and/or perfusion data.

In many cases, the outflow data can significantly assist with diagnosing the possible causes of a patient's erectile dysfunction issues. For example, the total venous blood outflow could be compared to the total arterial blood inflow, and any hemodynamic imbalance identified by comparing the relative inflow/outflow balance. In other embodiments, if the venous blood outflow increases in proportion to increases in arterial blood inflow, but the rate of change of the venous outflow does not alter at some point (i.e., the slope of the rate of change of the outflow does not reduce over time), this may indicate an abnormality in the compression of the subtunical venous plexus and/or emissary veins against the non-stretchable tunica albuginea.

Figure 9:
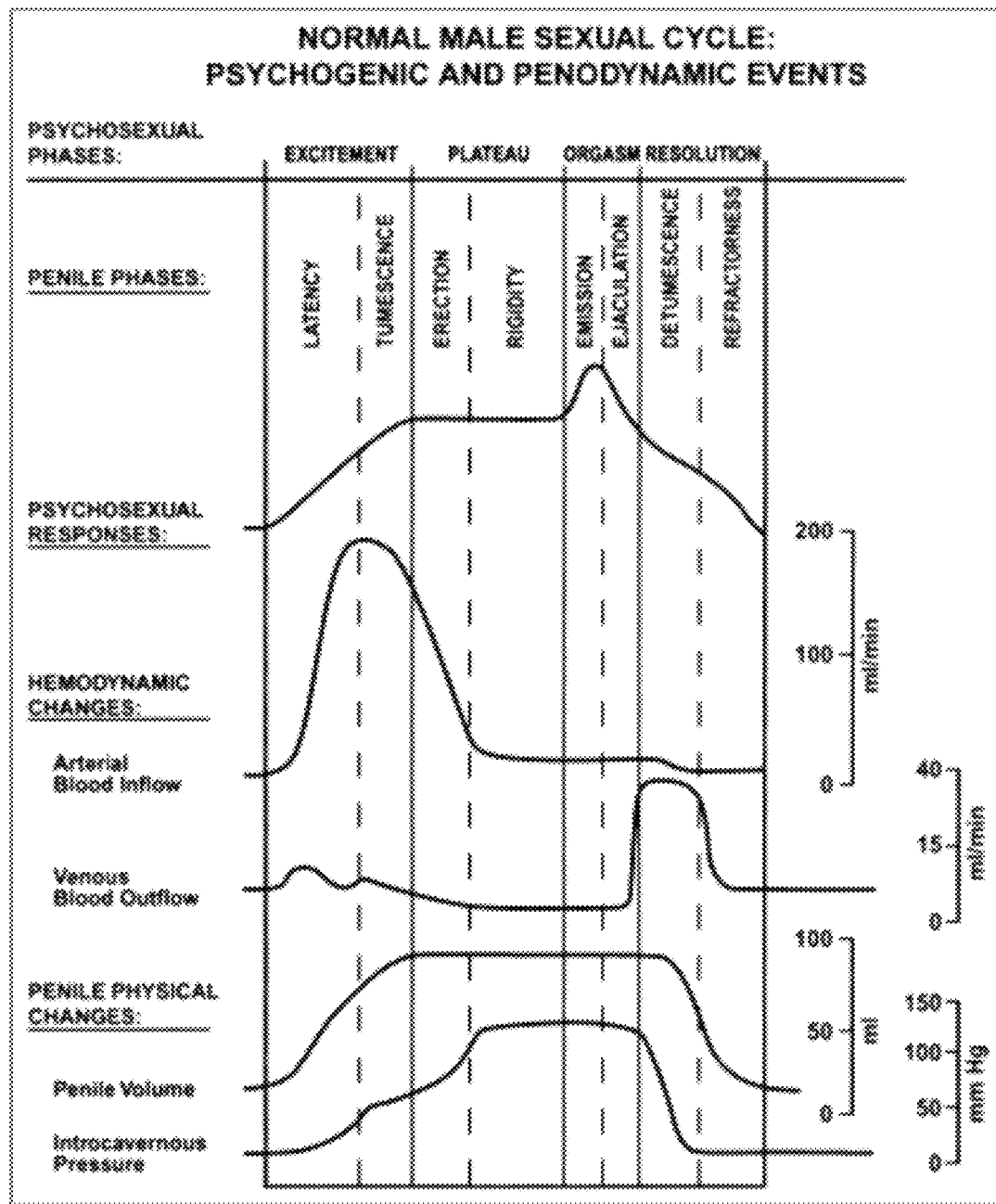
FIG. 9 depicts various exemplary parameters in a typical male sexual cycle.

FIG. 9 depicts various exemplary parameters in a normal male sexual cycle, including psychogenic and penodynamic events. The psychosexual response cycle has four major phases: excitement, plateau, orgasm, and resolution. They are represented by the solid vertical lines and by the top diagram. Each of the psychosexual phases comprises two interrelated physical events, which are represented by the vertical dashed lines. The penile hemodynamic changes associated with the sexual cycle (arterial and venous flow rates) are depicted in the middle portion, and the penile physical changes (volume and intracorporeal pressure) are depicted in the lower portion of the graph. Arterial blood inflow rate increases dramatically during latency, tumescence, and early stages of erection. This increase in arterial inflow is accompanied by an earlier increase in venous return, and results in gradual expansion of the cavernous tissue, increase in intracorporeal pressure, obliteration of emissary veins, and ultimately the restriction of venous return. The rise in intracavernous pressure, in turn, leads to a progressive decline in the arterial inflow to a temporary cessation during full penile rigidity. Venous drainage also completely ceases with full penile rigidity.

As the corporeal smooth-muscle cells begin to contract in late ejaculation, venous return increases sharply and remains high during the detumescence phase until the entrapped blood is fully drained and the intracorporeal pressure declines to its baseline level, which is maintained during the flaccid state. Penile volume expands maximally during late erection, and intracavernous pressure rises maximally during full rigidity. During detumescence, vasoconstriction of the arterioles and the reversal of events within the contractile corporeal units divert the blood away from the cavernous sinuses and allow an increase in the venous drainage of their contents. Initially, the rate of blood outflow increases by about tenfold, following which the rate decreases progressively until it reaches the pretumescence level. Local penile α-adrenergic receptor activation is the most important neuromediator mediating detumescence, and interference with this function, such as with α-1-receptor blockade, can lead to the development of priapism.

Data Modeling and Analysis

In various embodiments, the image and/or perfusion data obtained from a patient can be queried to identify a variety of anatomical parameters, including the volume, pressure and type of blood flow into and out of the penile tissues and associated vessels. Depending upon the type(s) of imaging modality and the quality of data obtained therefrom, it may be possible to perform an initial query and/or data modeling to identify a gross flow of blood into and out of the penile tissues, and depending upon the results of this gross analysis, further analysis may be necessitated and/or recommended.

For example, it may be possible to obtain image data along a flat and/or volumetric plane of tissue (either by direct imaging and/or after modeling of the image data), with the plane intersecting the prostate and/or lying perpendicular to the base of the penis, with the data capable of being queried to identify the flow of blood into the plane as well as out of the plane. If desired, a "gross" analysis could be performed that compares the flow into the plane (and/or within a portion of the volumetric plane in a first direction) to the flow out of the plane (and/or within a portion of the volumetric plane in a second, opposing direction), and assigns values to the derived values. This information could then be queried to determine if sufficient blood flow was occurring in the penile tissues, and appropriate actions taken.

For example, if the modeled data identified insufficient arterial flow into the penile region, then analysis of the patient's vasculature could be conducted in an attempt to identify a constriction or blockage of the arterial blood inflow, with possible surgical or other intervention being taken to correct the constriction or blockage. Alternatively, one or more injections of angiogenic compounds could be initiated to desirably increase the density and/or patency of the vessel network supplying blood to the penis, in an attempt to increase the overall blood inflow. If the modeled data identified insufficient dilation of the arterial vessels to provide sufficient increased blood flow to induce an erection, then one or more injections of angiogenic compounds could possibly be initiated to desirably increase the density and/or patency of the vessel network supplying blood to the penis, in an attempt to increase the ability of the vessel network to dilate in a more normal manner during the erectile cascade. If the modeled data identified sufficient blood inflow but excessive venous blood outflow, then one or more injections of vaso-occlusive materials might be initiated to desirably decrease the volume of blood outflow within the penis and/or venous drainage vessels, in an attempt to balance the hemodynamics of the penile system and allow the patient to attain an erection (while desirably ensuring sufficient venous outflow remains to avoid a priapism).

If desired, a similar approach to imaging and analysis could be undertaken for the patient in a second penile state, such as during arousal and/or after injection/ingestion of a medication that promotes the development and/or maintenance of an erection. This information could then be queried to determine if sufficient blood flow was occurring in the penile tissues during the second state, and appropriate actions taken. Alternatively, the data obtained from this second stage could then be compared to that of the first state, queried to determine if anticipated and/or desired changes to the blood flow were occurring in the penile tissues, and appropriate actions taken. For example, a vasoactive injection and/or a dynamic infusion cavernosometry may be performed. A vasoactive injection is where a physician injects a vasodilating substance, i.e., prostaglandin E1 (alprostadil), into the corpora cavernosa to pharmacologically induce an erection. If the penile vasculature is normal or at least adequate, an erection should develop within several minutes (i.e., 0 to 5 minutes). The physician can judge the quality of the erection. The dynamic infusion cavernosometry is used to determine whether a venous leak is present. During this test, various fluids can be intravenously pumped into the penis at a predetermined rate to induce an erection. By measuring the rate at which fluid must be pumped to induce an erection, and/or the drop in pressure rate, the severity of the venous leak can be quantified.

If the resulting "gross analysis" data exceeded a desired threshold, then it might notify the system and/or an operator to conduct further analysis, such as when the image and/or perfusion data could be further queried in a more precise fashion, which could include analysis of individual vessel flows and/or tissue conditions within various regions of interest. Alternatively, additional imaging may be required and/or requested, if necessary. In a similar manner, additional analysis of the various vascular branches leading to and/or from the penile tissues could be examined, if desired.

In various embodiments, the image and/or perfusion data can be queried and modeled in a variety of ways. For example, the blood inflow to and outflow from the penile tissues and the amount and pressure of blood within the corpus spongiosum could be modeled as a closed, open and/or partially open flow system. In some instances, the blood flow and amount of blood within the penis/corpus spongiosum might be analogized to and/or modeled as a water or flood control system including one or more weirs. Where the blood inflow exceeds the blood outflow, the amount and pressure of blood within the compartments of the corpus spongiosum should increase, while if blood inflow equals or is less than the blood outflow, the amount and pressure of blood within the corpus spongiosum should not be expected to increase. The dilation of the arterial supply vessels could be analogized to valves that open to allow increased blood inflow into the system, while compression of the venous plexus of the corpora spongiosum could be analogized to outflow valves being constricted and/or closed. The amount and/or pressure of blood within the penis and/or various compartments therein could be analogized to the volume and volume of water within the weir. If desired, the blood flow within the vessels could also be modeled, with degenerated and/or sclerotic vessels being modeled similar to corroded, constricted and/or occluded water and/or sewage pipes. Using such analogous modeling, therefore, could allow the hemodynamic conditions of the penile tissues and related anatomical systems to be modeled and/or analyzed using readily available commercial engineering software and equipment, if desired.

Of course, where a modeling system particularized to human anatomy is available and/or developed, the modeling of the penile hemodynamics may be readily conducted using image data such as described herein. In many cases, the normal anatomical variations within a patient population and/or within a specific patient could be modeled, which may begin with a "standard" blood flow model allowing for various alterations in blood flow patterns and/or other parameters—which may be particularized for a specific patient based on the anatomical image and/or perfusion data obtained herein. For example, in a typical region of penile tissues, the vasculature and/or microvasculature within and adjacent to the region will often not be constant across the entire region, but rather can vary depending upon the relative location of the various vascular sources supplying blood and nutrients to the region. Tissues closer to vascular supply sources are more likely to receive sufficient oxygen and nutrition than tissues further from such sources. Moreover, various factors can affect the distribution and/or integrity of the microvasculature, including age-related diminishment of vessels and/or various diseases.

Once a proper hemodynamic model has been created that incorporated sufficient data to approximate the patient's hemodynamic conditions, which may include modeling of changes in the patient's hemodynamic state reflective of data obtained during different penile conditions (i.e., flaccidity, arousal, tumescence, resolution), the model will desirably allow a user and/or the system to alter various structural and/or flow parameters to determine how such changes will affect the overall system. Desirably, such changes can be utilized to model system responses to various intended surgical and/or pharmacological interventions, which can allow the system and/or user to determine an optimal course of treatment for the patient.

For example, where vessel degradation has damaged the ability of the tunica albuginea to compress the venous plexus (which desirably constricts subtunical venous outflow during tumescence), it would be desirably to know whether surgical vaso-occlusion of some portion of the venous plexus might result in an improved erectile response. It would also be desirable to know the amount and/or location(s) of any venous plexus that could be occluded/constricted and yet still allow for proper deflation of the penis after satiation (i.e., to prevent a priapism of the penis). Desirably, the resultant modeling could provide a physician with a recommended approach for improving and/or correcting a patient's erectile dysfunction, which could then be accomplished surgically, pharmacologically and/or via various lifestyle changes.

Erectile Response

The classic four-stage model of male sexual response leading to an erection is defined by excitement, plateau, orgasm and resolution. Sexual excitement occurs as the result of external sensual (visual, auditory, tactile, or olfactory) and internal psychic stimuli to the limbic system, leading to activation of the sacral parasympathetic pathway and inhibition of the thoraco-lumbar sympathetic pathway. This produces relaxation of the penile corporeal smooth muscles and helicine arterioles, allowing increased arterial blood inflow and, thus, increased penile volume due to its filling with blood. The fall of resistance within the corporeal vascular bed and the subsequent increase in arterial inflow are the major vascular events leading to erection of the penis.

Central to these events is the corporeal contractile system, which is composed of bundles of smooth muscles, vascular endothelium, and elastic fibers. Relaxation of the smooth muscles with a concomitant stretching of the endothelium leads to enlargement of the sinusoidal or lacunar spaces and an increase in their capacity for blood storage. Distention of the sinusoidal spaces within the corpora cavernosa with arterial blood tenses the surrounding tunica albuginea and compresses the subtunical and emissary veins, thereby reducing venous drainage. The progressive increase in intracorporeal pressure leads to penile expansion, tumescence, and rigidity. The pressure in the lacunar spaces during erection is the result of equilibrium between the perfusion pressure in the cavernosal artery and the helicine arterioles and the resistance to blood outflow through the compressed subtunical venules.

Activation of the sacrospinal reflex subsequent to direct genital stimulation during the plateau phase leads to contraction of the ischiocavernosus muscles and stimulation of the corpus spongiosum and the accessory Cowper's and Littre's glands. Contraction of the pelvic floor muscles augments the intercavernous pressure, resulting in decreased venous blood outflow. The coordination of these activities produces a state of full erection and rigidity. Further, stimulation of the corpus spongiosum and accessory glands leads to the dilation of the urethral bulb and the secretion of a lubricating fluid. As sexual pleasure approaches its climax, activation of the thoracolumbar spinal reflex occurs, leading to the contraction of the vas deferens, ampulla, seminal vesicle, and the prostate. This results in the deposition of the seminal fluid in the posterior urethra. Rhythmic contractions of the bulbocavernosus and the pelvic floor muscles, usually at 0.8 second intervals, lead to expulsion of the seminal fluid (ejaculation), which is accompanied by concomitant closure of the bladder neck to prevent the retrograde fall of semen into the bladder cavity.

After the release of sexual tension and at the onset of the resolution phase, a thoracolumbar sympathetic pathway acts to contract the corporeal smooth muscles and the arterial tree, thereby limiting blood inflow and augmenting venous outflow, producing penile flaccidity. A refractory period, during which a subsequent full erection or repeated orgasm is nearly impossible, ensues.

A dramatic increase in penile arterial blood flow to about 25 to 60 times that of the flaccid state occurs during the rapid period of tumescence. It is believed that a peak cavernosal artery systolic flow greater than 25 ml/sec is required for erection to occur. At full rigidity, an increase in penile length of 7.5 cm usually requires the entrapment of 80 to 115 mL of blood. As the penile volume increases to near maximum (from less than 10 mL in the flaccid state to about 60 mL in the erect state), the arterial influx declines and plateaus at a level that is sufficient to keep the penis in the rigid (erect) state. Imaging studies have shown that a fluid flow rate between 5 and 40 mL/min is required to maintain a normal penis in the erect state. Further, at these minimum flows rates of full erection, the cavernosal artery occlusion pressure equilibrates with the intracavernous pressure. With maximum rigidity induced with pelvic muscle contraction, supra-systolic pressures are generated, and cavernosal artery flow ceases transiently.

The initial increase in blood inflow during sexual excitement is associated with a transient increase in venous return. As penile tumescence ensues and compression of the subtunical venous plexus and emissary veins against the non-stretchable tunica albuginea occurs, venous return falls and the end diastolic cavernosal artery flow reverses (up to 7 mL/sec). At the conclusion of ejaculation, a rapid increase in venous outflow occurs as a result of the contraction of the corporeal smooth muscles and diminution in the compression pressure to the subtunical and emissary veins. The rate of venous flow returns to that of the flaccid state at the conclusion of the detumescence phase.

The intracorporeal pressure during the flaccid state is between 10 and 15 mm Hg. Intrapenile pressure changes are modest during the initial phase of the sexual cycle and remain so until near-maximum changes in circumference and volume are attained. As the penis becomes erect, the penile body pressure increases rapidly to about 90 mm Hg. Perineal muscle contraction results in further increase in penile body pressure to greater than 120 mm Hg (suprasystolic pressure), which results in full rigidity and elevation of the penis to greater than 90° from the plane of the lower extremities. Following orgasm, penile body pressure declines rapidly and penile volume returns to the flaccid size. Studies suggest that the intrapenile pressure normally drops at a rate of less than 1 mm Hg/sec during the detumescence, as reflected by the rate of drop in intrapenile pressure when fluid infusion is discontinued.

Overlapping/Interconnected Vascular Systems

In addition to anatomical variation, another significant challenge facing the accurate imaging and analysis of the penile vasculature is the overlapping nature and/or numerous redundancies and/or variations in the vascular blood supply to and/or from the penile tissues. While the main blood supply to the corpora cavernosa are typically the paired deep arteries of the penis (cavernosal arteries), there are many cross-connections between the cavernosal spaces, and the corpora cavernosa can also receive blood from the dorsal artery, the bulbo-urethral artery, and various accessory pudendal arteries (which may originate from the obturator artery, the inferior pudendal artery, the iliac trunk and/or the inferior gluteal artery). Venous drainage of the penis is similarly complex—the lacunar spaces or vascular sinusoids of the corpora cavernosa drain through subtunical veins beneath the tunica albuginea into the emissary veins by way of the deep dorsal vein of the penis. The deep dorsal vein culminates in the periprostatic venous plexus superior and lateral to the prostate. The superficial dorsal penile vein lies above Buck's fascia and provides drainage predominantly for the penile skin culminating in the saphenous vein. The proximal penile shaft and proximal corpus cavernosum drains through veins exiting the crura of the corpora cavernosa (termed the crural veins) that join to form the internal pudendal vein. As with most venous systems, the venous drainage of the penis is variable and complex and has multiple intercommunications.

While the previously described vascular variations can significantly increase the complexity of imaging and/or analyzing the vascular blood flow of the penis, they also demonstrate the resiliency and adaptability of the penile hemodynamic system to alterations in the penile blood flow. In various embodiments, it may be desirous to introduce angiogenic compounds in an attempt to increase blood inflow, while in other embodiments it may be desirous to alter venous blood outflow (and/or various combinations of both). Desirably, the ultimate penile hemodynamics will be relatively insensitive to the specific "source" and/or "drainage" of the blood flow (and the various interconnects between the source vessel network and/or the various interconnects between the drainage vessel network), but will rather simply respond to the volume and dynamic balance of blood flow—and in such cases it may be possible to redirect blood flow from/to other vessels, with commensurate improvements in ability of the patient to achieve erection or some other outcome measure.

For example, the deep and dorsal arteries of the penis are two overlapping vascular systems capable of supplying blood to the corpora cavemosa of the penis. One system is primarily targeted to filling the corpora cavemosa, while the other primarily supplies other penile anatomy. An initial dynamic MR Perfusion technique can be utilized to produce a more pronounced temporal resolution with less spatial resolution and demonstrated rapid flow into the penile tissues with a rapid wash-out rate, desirably providing sufficient data to accurately model one or both of these blood supply systems and/or associated tissue structures. In one exemplary embodiment, modification of pulse sequences for a higher spatial resolution (smaller voxel size with a submillimeter in-plane resolution) at a cost of lower temporal resolution (a longer sampling time for each dynamic frame) can allow for localized enhancements around cavernosal tissues that might not be evident from the data provided by a higher temporal resolution DCE-MRI (at a cost of lower spatial resolution). In addition, this technique can display time-course data (dynamic data) that is more associated with a discontinuous (or porous) capillary network. It is believed that this type of capillary is utilized by the hematopoietic functions of the penile tissues to a greater extent (allowing large cells to migrate from the intravascular and extravascular compartments). However, where a modified DC-MRI (dynamic contrast magnetic resonance imaging) perfusion study is utilized, a significantly greater spatial resolution (and less temporal) protocol can be achieved, and this approach demonstrates significantly greater detail in penile tissues and/or vessels of interest. Utilizing such a modified imaging protocol, therefore, it may be possible to successfully image an enhanced blood supply/drainage system, capillary network(s) and/or various penile tissues that can provide useful image data to be analyzed in various of the embodiments described herein. Such imaging parameters can allow detection of a time-course data consistent with a function of blood and oxygen supply and/or nutrient/waste exchange.

In various embodiments, scans can be created demonstrating significant dynamic penile vasculature and/or dynamic penile tissue perfusion that can be quantified with resolution up to 1 mm "in plane" and showing time course data that is consistent with vessels and/or capillaries that are continuous (no pores).

It is believed that various imaging and analysis approaches to the imaged data can be utilized in varying ways to identify vascular deficiencies and/or diffusion insufficiencies within and/or adjacent to penile tissues of interest. In various embodiments, image data can be acquired that reflects perfusion of blood in and/or proximate to the various penile tissues. Where proper imaging modalities are used, and combinations of such data obtained from differing imaging modalities combined in a desired manner, image data can be acquired that reflects the flow and/or flowpaths of blood and/or other nutrients to, from and/or within the penile vasculature In various alternative embodiments, image data can be acquired that reflects the structural composition of the penile structures, including reconstruction of the various circulatory and/or microcirculatory paths within the penis itself. Another approach could include imaging and/or analysis of waste metabolites or "markers" exiting the penile structures, which may include collection and analysis of blood or other fluids exiting the penile structure or non-invasive imaging assessment of the presence of such waste "markers" in the vascular system and/or relevant tissues of the penile structures.

In various embodiments described herein, anatomical image data from a patient can be obtained and the image data for the pelvic regions and/or the penile anatomy can be analyzed for the presence and/or likelihood of vascular and/or penile tissue ischemia. For example, the image data of a vascular network supplying the penis can be selected and analyzed using various techniques described herein, and the resulting analysis queried for the presence of hypoperfusion.

In one particular preferred embodiment relating to imaging and analysis of soft tissue structures, parameters used for MR imaging of such soft tissues may include: TR 3200 ms, TE 119 ms milliseconds, and thickness of 4.0 mm with gap 0.4 mm. In one alternative embodiment, parameters used for MR imaging of soft tissues (i.e., connective tissues and/or spinal discs) could include: a final T2w protocol of TR/TE=5000/120 (ms) and imaging voxel-size equal to 0.8×0.8×3.0 (mm$^3$) or 3.0-mm gap with no gap.

Numerous methods are known in the art that could potentially be used to identify areas of hypoperfusion, as well as image the pelvic region and/or penile vascular supply/drainage networks. These methods can include MR-based techniques such as diffusion-weighted imaging, T2 and T1-weighted anatomical magnetic resonance imaging (MRI), diffusion tensor imaging (DTI), magnetic resonance spectroscopy (MRS), T1ρ weighted MRI, dynamic contrast-enhances MRI (DCE-MRI), T2 relaxometry MRI, CT-scan (computed tomography scan), and provocative discography. Diffusion-weighted imaging can provide quantitative analysis of disc degeneration and early changes over time as previously described. T1ρ MRI can be used to measure proteoglycan or other tissue material content. Any of these techniques may be used alone or in combination to diagnose erectile dysfunction and related tissue issues, as described.

In one particular embodiment, an area of hypoperfusion could be identified using technetium-99m Sestamibi in conjunction with single photon emission computed tomography (SPECT) imaging. This radiolabelled lipophilic cation can be injected intravenously at concentrations ranging from 200-1790 MBq, more preferably 500-1000 MBq, and even more preferable at approximately 750 MBq. Imaging is performed with a gamma camera and absorption/perfusion is quantified using various software packages known to one skilled in the art. In some embodiments, to attain appropriate images of the pelvic area, the camera can be rotated 360 or less degrees and/or in one, two and/or three dimensions relative to the imaged anatomy. In other embodiments, various means of detecting hypoperfusion can be employed, for example, PET-CT (positron emission tomography-computed tomography), DCE-MRI, and, for example, fluorescent peptide-based methodologies.

Imaging of Pelvic/Penile Arteries and/or Veins and/or Microvasculature

Various embodiments of the invention can include imaging and/or analysis of anatomical structures that can be directed to detection of ischemia-associated conditions and subsequent treatment through angiogenic stimulation and/or venous occlusion (or various combinations thereof). While previous studies have suggested an association between atherosclerosis and erectile dysfunction, a quick and repeatable method of imaging the relevant anatomy, analyzing and identifying a direct causal relationship and treating the vascular imbalances via angiogenesis has not been advanced. The invention discloses various novel diagnostic algorithms that can be utilized in the diagnosis and selection of patients for subsequent treatment utilizing pro-angiogenic approaches. To date, methods of imaging and treating pelvic vasculature relevant to erectile dysfunction have been largely unsuccessful, primarily due to the small size and tortuosity of the pelvic vasculature, the difficulties of imaging the degenerative pelvic vasculature (i.e., degenerated and/or calcified tissues can often interfere with various imaging modalities) and the significant risks that open surgery of the pelvic region entail. In many instances, erectile dysfunction is considered merely a "lifestyle issue" rather than a critical health condition requiring a medically necessary surgical procedure to repair or preserve the healthy functioning of the body.

In many instances, a blockage or occlusion of an "upstream" blood vessel can significantly reduce the oxygen and/or nutrition flow to the tissues of the penis or other "downstream" anatomy supplied by the vasculature. Similarly, a blockage or occlusion of a "downstream" vessel can significantly degrade the ability of the "upstream" vascular system to scavenge and/or remove fluids such as blood plasma, cells, various waste products and CO2 from the penis and/or other vasculature, as well as inhibiting the positive flow of nutrition into relevant tissues-of-interest. Various embodiments of the invention can include imaging of anatomical structures remote from the penile tissues of interest, with the results of such imaging utilized to detect vascular hypoperfusion, ischemia-associated tissue degradation and/or the need for subsequent treatment including some form of angiogenic stimulation. Various embodiments of the invention disclose novel diagnostic algorithms that can be utilized in the diagnosis and selection of patients for subsequent treatment utilizing pro-angiogenic approaches. Diagnostic imaging algorithms have not been widely use in the treatment of many ischemic-related diseases, since no vascular basis for many degenerative conditions have been accepted in various fields and/or specialties of medicine and surgery.

In one aspect of the invention, magnetic resonance angiography (MRA), a special type of MR which creates three-dimensional reconstructions of vessels containing flowing blood, is utilized to identify vascular abnormalities. By imaging various arteries, veins and/or other vessels, a rating system can be developed to measure the amount of patency of and/or flowrates within the vessels. The following system is an example of such a system:

| Arterial Occlusion (Deep Arteries of Penis) 2 vessels (left and right) |
|---|
| 0 = both vessels are patent 1 = one vessel is stenotic 2 = both vessels are stenotic 3 = one vessel is occluded 4 = one vessel is occluded and one stenotic 5 = both vessels are occluded |

Similar to this vessel grading system, perfusion within the penile anatomy could be defined with a numerical scale depending upon the hypoperfusion location in the penile tissues and/or supporting vasculature, including the quantity of perfusion and/or the level of microvascular integrity and/or tissue degeneration (based upon ADC and/or T1ρ, for example).

| Penile Tissue and Supporting Vasculatare Possible Classification System |
|---|
| 0 = penile tissues have adequate perfusion 1 = one corpus cavernosum supply exhibits hypoperfusion 1a = one corpus cavernosum supply exhibits no perfusion 2 = both corpus cavernosa supplies exhibit hypoperfusion 2a = both corpus cavernosa supplies exhibit no perfusion 3 = penile surface tissues exhibit hypoperfusion 4 = both corpus cavernosa supplies and penile surface tissues exhibit hypoperfusion 4a = both corpus cavernosa supplies and penile surface tissues exhibit no perfusion |

A penile perfusion grading and classification system could be as simple as the above chart with complexity being added depending upon the inclusion criteria that develops by researching various combinations of imaging techniques as described herein (including, for example, combination imaging strategies, etc.). With further quantitative pelvic vasculature and/or tissue research, numerical criteria could determine classifications, along with other quantitative imaging assessments already discussed, creating a clinically relevant classification and/or treatment system.

Data Modification, Analysis and Assessment

Once sufficient image data has been obtained, and has been sufficiently segmented and identified as relevant (if desired), it can be analyzed in a variety of ways. The data may also be processed, enhanced, filtered and/or otherwise modified in a variety of ways to desirably enhanced the detection and identification of various values of interest, which in various embodiments may include structural and/or functional qualities of pelvic and/or penile vasculature, microvasculature and/or capillaries. While various embodiments described herein include the analysis and assessment of pelvic and/or penile tissue pathologies, it should be understood that the techniques and treatments described herein can be applied with equal utility to other joints of a human or animal body, as well as to other tissues and organs.

Various embodiments described herein include the use of a variety of image data types, and a variety of analysis approaches to the imaged data, which can be utilized in varying ways to identify vascular deficiencies and/or diffusion insufficiencies supplying to and/or within the pelvic/penile anatomy. Relevant image data and analysis particularly useful in various embodiments disclosed herein can include one or more of the following (each of which may be utilized alone or in any combinations thereof): (1) analysis of the structure of bones and/or soft tissues of the pelvis, including relevant vasculature, micro-vasculature and related tissue structures and/or compositions, (2) analysis of the flow and/or flowpaths of blood and/or other nutrients and wastes, and (3) analysis of nutrients, waste metabolites and/or "markers" entering and/or exiting the penis and/or other pelvic structures, which could include collection and analysis of blood or other fluids exiting the pelvis or non-invasive imaging assessment of the presence of such nutrient/markers in the vascular system and/or relevant tissues of the penis and/or pelvic anatomy.

As previously noted, one unusual feature of the penile anatomy is that the various tissues can be capable of receiving fluid and/or nutritional components from a variety of vascular conduits (i.e., vessels) within the body (and also the disposal of fluid and/or nutritional components as well). The multi-vascular flow that delivers blood and/or nutrients to the various penile tissues can potentially complicate the analysis, assessment and treatment of vascular hypoperfusion and/or deficient diffusive nutrient flow to various penile tissues. In various embodiments, such multi-vascular flow will desirably be modeled and/or otherwise accommodated in the imaging and analysis of the supply and drainage system to an individual's penile anatomy.

In various exemplary embodiments, the relevant features of both the arterial supply and venous drainage of the penile anatomy are desirably imaged, identified and analyzed. Moreover, because the penis can potentially receive blood from a variety of vascular sources and/or conduits (with similar considerations for blood drainage), a deficiency in one source may not necessarily result in significant erectile difficulties. For example, experimental data has shown that the corpus cavernosa of one side of the penis often freely communicates with the other corpus cavernosa through various conduits. However, where the blood flow to both corpus cavernosa are compromised to some degree, or where a significant degradation of one source cannot be accommodated by sources feeding the other side of the penis, the diagnosis may mandate some form of angiogenic (or other) treatment.

In various embodiments, the imaging and analysis of one or more individual major vascular conduits to and/or away from the penile tissues may be indicative of a potential or actual condition causative of erectile deficiency, and in such cases the hemodynamic model of the patient's penile anatomy might optionally normalize, assume an equivalent condition for and/or otherwise ignore the contributions of one or more minor vascular conduits to/from the relevant anatomy in the hemodynamic model of the patient's anatomy. Moreover, where a degraded or deficient vessel conduit can be assumed (i.e., where prior vessel degradation and/or prior surgical treatment has identified and/or caused one or more blood conduits to be compromised in some manner), such information can be incorporated into the hemodynamic model. In various embodiments, the effects of diffusion and/or other nutrition/waste flow relative to the vascular conduits in and/or adjacent to the penile tissues may be imaged, quantified and analyzed in the various analytical and treatment regimens described herein, as may the structural and/or internal vessel conditions such as sclerosis, constrictions and/or occlusions.

In various embodiments, three-dimensional (3D) imaging data of a patient's anatomical structures within and/or immediately adjacent to the pelvic and/or penile anatomy can be obtained and analyzed. In at least one desirable embodiment, the 3D data will include information regarding the vascular supply and drainage of the entire pelvic region, while in other embodiments the 3D data may include only information regarding the vascular supply and drainage of only the penile tissues (i.e., the "Region of Interest" or "ROI"). In addition, the 3D data will desirably be of a sufficient resolution to differentiate and identify the relevant vasculature within this Region of Interest, which may include various features of the microvasculature therein, including capillary beds, various venous plexus structures and/or other microstructure(s) therein. In various embodiments, the data may alternatively and/or in addition comprise analysis of the perfusion of blood and/or other nutrients and wastes and/or analysis of nutrients. In a similar manner, waste metabolites and/or "markers" entering and/or exiting the penile structures and/or pelvic region can be imaged and analyzed. In addition, since a ROI could be placed anywhere on the imaged data, anatomy outside of the pelvic region could also be investigated with this technique, which may be useful in diagnosing non-pelvic vascular and/or tissue deficiencies and/or other conditions with vascular anatomy imaging (MRA) and simultaneous Dynamic Perfusion.

Absent an injury, the typical degenerative process of vasculature and/or various penile tissues leading to erectile dysfunction can be a slow, continuous process, which is expected to be at varying functional stages for patient at different stages of life. However, quantitative measurements and/or other risk factors (i.e., having diabetes or heart disease) such as those described herein may delineate subtle changes that can be clinically relevant. As precursor to morphologic changes, such functional measurements and/or risk factors may be especially valuable during the early phases of the degeneration process where no major morphological change is expected or anticipated to be present in the penile tissues, or at least not at an easily detectable level. Ideally, any potential quantitative, functional measurement reflecting the dynamic degenerative stages can be evaluated in correlation to an established quantification method, which could include quantification based on other functional aspects of the pelvic vasculature. Where such subtle changes can be identified and/or detected, they can also be treated with several of the methods described herein (as well as others that may be developed in the future), which may slow, prevent and/or reverse the onset of later stages of tissue degeneration in the penis and/or other regions of the patient's anatomy.

In various embodiments, assessment of a patient's vasculature and penile tissues can include the identification of an Apparent Diffusion Coefficient (ADC) measurement, which can be a tissue-related functional quantitative rating for diffusion and/or T1□ relaxation time which is believed to reflect proteoglycan or other constituent content in the various tissues of the vasculature and penis. Both ADC and T1□□ quantitative measurements desirably enable imaging and detection of small changes over time to allow identification and/or quantification of one or more "at risk" tissues. In various embodiments, the "at risk" tissues could be tissues that are associated with subtle changes in the ADC and/or T1☐ value, as well as a possible increased level of pain and/or decreased function, which may or may not be associated with changes in the image morphology or grade of the penile vasculature. In addition, in various embodiments, vasculature that may be affected by another treatment regimen for the patient might be considered "at risk" with certain combinations of ADC/T1☐ (or changes in ADC/T1☐ or other quantitative measurements), penile tissue vascularity and/or other quantitative measurements of tissue integrity. These measurements could prompt a corresponding treatment to improve the condition of the penile vasculature either prior to the prescription of medication (which may include medications having known and/or unknown effects on erectile response) or other surgical treatments, during pharmaceutical and/or surgical intervention and/or subsequent to pharmaceutical and/or surgical treatment and/or follow-up.

A significant advantage in the employment of the imaging and assessment systems described herein is the ability to measure and assess small changes in the pelvic vasculature and/or penile tissues over time in a highly accurate manner. This facilitates the identification and/or quantification of subtle metabolic and structural changes in one or more "at risk" tissues, including the cavernosal tissues of the penis. Until the approaches described herein were developed, such subtle changes could be difficult and/or impossible to detect, which made it commensurately difficult to determine if a given surgical intervention and/or treatment was going to be particularly effective in treating and/or ameliorating a degenerative condition causing erectile dysfunction. By employing the various systems and methods described herein, however, it becomes a relatively straightforward process to assess and quantify the various advantages and/or disadvantages that a given clinical intervention will be providing in the treatment of an erectile issue. If desired, measuring the nutritional and metabolic parameters of penile tissues before and after treatment can offer an evidence-based approach to analyzing the outcome, which can be of significant value to the assessment of existing treatment regimens as well as those to be developed in the future.

In some embodiments, specific grades of tissue degeneration and/or hemodynamic imbalance can be chosen for treatment, or a relative measure of blood supply/drainage between adjacent corpus cavernosa of a single patient may be compared to identify one region having unusual and/or atypical values, which may indicate need for treatment and/or further assessment. Various embodiments described herein include the employment of 2-dimensional and/or 3-dimensional analysis of the vascular circulation and microcirculation affecting penile tissues. This may include localized analysis and/or "weighting" of the circulation/microcirculation measurements in different areas of the penis and/or corpus cavernosa, such as where the circulation and/or microcirculation of the venous plexus adjacent to the tunica albuginea of the penis comprises a significant factor in the hemodynamic balance leading to erection. In various embodiments, some vascular and/or tissue structures of the penis may be of a lesser quantity and/or lesser effect to the erectile condition of the patient, while other vascular and/or tissue structures may contribute the bulk of blood supply/drainage and/or nutrition/waste disposal for the penis. In addition, multi-parametric analysis provides a method to assess multiple aspects of a pathologic process that may exist simultaneously. This technique can provide important information on the degree of penile hemodynamic imbalance experienced by the patient, as well as serve as a potential early indicator of other degenerative vascular conditions (i.e., advanced atherosclerotic degeneration which may lead to heart disease and/or death).

If desired, one embodiment of modeling and analysis of the vasculature and/or microvasculature could include the step of structural modeling of the vessel anatomy and/or perfusive blood flow in the pelvic region, in the penile tissues, and/or within a broader region of the patient's vascular system, which can include simulation modeling of the hemodynamic blood flow into and/or out of the penis during a variety of conditions (i.e., flaccid, aroused, tumescent and/or resolution states). The modeling could further incorporate data simulating the anticipated treatment(s) and/or outcomes based on a variety of treatment regimes, including the use of angiogenic treatments and/or vaso-occlusive treatments such as described herein. For example, the perfusion data from an imaged region might show a region of vasculature and/or microvasculature within the pelvic region that is sparsely populated with vessels and/or involves lower-than-normal flowrates to the penile tissues. It may be desirous to modify the model of the region to incorporate vasculature and/or capillaries that are more densely distributed, and/or vessels growing more proximate and/or closer to an area of ischemic tissue and/or a vessel occlusion, to determine whether an angiogenic treatment might be desired and/or appropriate to the region. In various embodiments, the modeling of capillaries, especially those in a highly structured tissue, could be approximated using an array of cylinders with nearly uniform spacing. Desirably, the model could be utilized to identify areas where angiogenic treatment could be particularly advantageous, as well as identify where drug delivery might be improved by reducing the distance to the nearest vessel and/or by ensuring that blood flow is sufficiently strong and/or uniform in the vascular/micro-vascular network so that each vessel is well-perfused. In another example, the perfusion data from an imaged region might show a region of vasculature and/or microvasculature within the penile tissues, such as the various venous plexus structures within the tunica albuginea of the corporal cavernosa of the patient's penis. Such data, if taken during a period of patient arousal (or taken during different patient states—i.e., flaccid, aroused, tumescence and/or resolution), might be queried to identify vessels within that region which do not respond to arousal stimuli and/or which are not compressed to a desired degree during tumescence (and/or attempted tumescence) of the penis. Desirably, the model could be utilized to identify areas where vaso-occlusive and/or constrictive treatments could be particularly advantageous (i.e., to restrict and/or cease blood flow within specific portions of such malfunctioning vessels), as well as identify where angiogenic treatments might be appropriate in such regions as well (if desired).

Metabolic Wastes

As previously noted, various embodiments described herein can include the use of imaging and assessment of vascular and/or tissue perfusion combined with measurement and/or assessment of lactate levels within a pelvic and/or penile structure with a minimally invasive diagnostic study, which can potentially provide independent confirmation of the disease diagnosis. Removal of waste may be measured by imaging lactate, hydrogen ion and/or other waste markers over time. If the imaging shows improvement of the amount of these metabolic waste products, then some conclusions can be drawn as to the integrity of the waste removal system. Conversely, an increased level of such wastes could lead to a diagnosis of deficit and/or failing waste removal systems. In addition, real time imaging would be possible with imaging sensitive markers tagged to these, or other waste metabolites.

The diagnosis and relevant treatment of the cause(s) (abnormal vascular supply with resultant poor nutrient delivery and/or waste removal) as described herein could significantly improve clinical management of erectile disorders. The ability to measure lactate can provide a metabolic marker that can be utilized to evaluate longitudinally, or eventually, help in the diagnosis of the cause of the erectile dysfunction. In one exemplary embodiment, MR Proton spectroscopy can be utilized to monitor the lactate content in tissues non-invasively. Alternatively, a MR spectroscopy protocol PRESS (point resolved spectroscopy) with CHESS (chemical shift selective) pulse to suppress water signal could be implemented to quantify lactate content in tissues. This type of spectroscopy in-vivo is possible with specialized hardware (coils) and appropriate software development. Experimentally, imaging on a subject in a 3T scanner has been accomplished, demonstrating a higher lactate level at a soft tissue structure (i.e., in the disc of the spine at a more degenerative L5-1 disc), which could be applied to other tissue structures, including penile tissue structures. As described herein, it is anticipated that improved data analysis will develop in the future with PRESS and SHIFT protocols, providing even cleaner and/or more useful lactate data in the various embodiments described herein.

Screening

In various embodiments, patients with erectile dysfunction and/or related conditions can undergo screening to determine whether their condition is likely to be associated with hypoperfusion or some other abnormality of the penile vasculature and related anatomy. Evaluation of patients with suspected vasculogenic impotence should eliminate some non-vasculogenic pathophysiologies, which may include psychogenic, neurogenic, endocrinologic, and/or hormonal pathophysiologies. For example, such screening is a common medical practice with other pathologies, and with regards to erectile dysfunction could include various additional techniques such as administering the International Index of Erectile Function (IIEF), physical and psychological examination, blood and urine tests, erectile volumetric studies and overnight erection tests, radiographic studies, MRI and tissue/bone scans and ultrasound examination, with or without associated CT scans, to diagnose vascular hypoperfusion and/or other hemodynamic imbalance contributing to erectile difficulties. Depending upon the relevant inclusion and/or exclusion criteria for a given condition, patients with extremely low blood pressure, severely compromised cardiac output and/or psychological issues affecting erectile response could be excluded from eligibility for treatment (if desired) using the methods and compositions described in the present invention. In a variety of cases, patients treated with the various inventions disclosed herein might be refractory to conventional treatments and/or pharmaceutical compositions (i.e., PDE-5 inhibitors). In a more specific embodiment, patients can be diagnosed based on an analysis of the pelvic and/or penile vasculature using magnetic resonance imaging. In preferred embodiments, the condition of the penile vascular network can desirably be estimated from regular T1 and T2-weighted MR sagittal fast spin-echo (FSE) and T2-weighted FSE axial images. Preferably, the tissues may be classified to various grades, which in one exemplary embodiment could comprise three grades: grade 0, tissues with high signal intensity or only slightly blurred intranuclear cleft, which represent normal tissues; grade 1, tissues with decreased signal intensity, which represents mild degeneration; and grade 2, tissues with markedly decreased signal intensity, which represent severe degeneration. In preferred embodiments, the signal intensities of penile tissues could be compared with those of tissue structures in other portions of the patient's body and/or with comparable readings from other patients and/or a population of equivalent patients and/or healthy individuals. If desired, ADC and T1ρ could be added to the T1 and T2w scans to analyse diffusion and/or proteoglycan content in an effort to quantitate the degree of tissue degeneration.

In one embodiment, ADC could be utilized to quantitate tissue degeneration with or without combining the data with qualitative approaches, similar to the Pfirrmann grading associated with degenerative spinal disc structures. A multi-parametric approach may be more appropriate wherein morphologic assessment of degeneration is utilized in conjunction with more quantitative measurement such as ADC. With large sample sizes, subcategories could be developed that correlated with specific degenerative patterns that may or may not require clinical intervention. In various embodiments, ADC could be utilized to measure diffusion in any plane. In addition, the relative contribution can be ascertained. In various embodiments, ADC maps could be utilized that can show greater diffusion in a specific anatomical plane, such as the Superior-Inferior plane (Anisomery maps). If desired, an ADC map could also be a representation of data that could correlate well with the various grading systems described herein.

In various embodiments, genetic screening and/or whole genome sequencing could be used to elucidate whether a patient has a greater potential to develop vasculogenic erectile dysfunction, as well as to determine which patient may or may not be receptive to various types of gene therapies or other treatments, including angiogenic treatments. Comparing gene sequences in patients with vasculogenic erectile issues with patients without these disorders can create one or more standards to facilitate a blood and/or urine test that could alert clinicians to the patient's susceptibility for erectile dysfunction and/or related conditions. This information, coupled with the imaging data already discussed, could refine the decision algorithms for treatment of erectile dysfunction due to hemodynamic imbalance.

In various embodiments, it may be desirous to identify a non-treatable condition or other pelvic/penile pathology that reduces and/or negates the effectiveness of a given course of anticipated treatment. Various types of image data could be employed to perform such analysis, including image date such as plain x-rays (as well as the various other imaging modalities described herein) that could show injuries and/or severe deformity that could be a contraindication for angiogenic treatment. Image data may be used to detect a calcified and/or thickened venous plexus that could inhibit venous compression and reduce and/or negate the effectiveness of angiogenic treatments in various circumstances. In addition, image data showing severe loss of blood flow and/or severely degenerated penile tissues may not allow the underlying vasculogenic condition to be treated. In addition, severe vessel degeneration and/or occlusion may not permit angiogenesis to occur to effectively increase pelvic and/or penile blood flow. In a similar manner, image data may be used to detect a calcified and/or blocked vessel that could cause a vascular deficiency that eventually inhibits blood flow into the penile tissues. Where this obstruction (i.e., partial and/or complete) is located remotely from the pelvic region and/or penile tissues, angiogenic treatments within the pelvic region/penile tissues may be relatively ineffective to significantly improve the patient's condition. Where multiple potential treatment areas may exist in a given vascular network supply to an area of interest, it may be advantageous to treat all of the multiple areas simultaneously and/or treat each area in a serial or "step-wise" fashion to desirably restore perfusion to the penile tissues.

Vessel Analysis

Once an ischemic condition and/or other hemodynamic imbalance leading to erectile issues has been identified using one or more of the imaging and analysis techniques described herein, various embodiments can include further analysis of anatomical image data of the major circulatory systems that feed into and/or drain out of the penile tissues and/or pelvic region, to identify any occlusions or partial occlusions (or other pathologies) that may be contributing to the hemodynamic imbalance and/or other causative condition. Where any occlusions or partial occlusions are identified in the imaged regions, a desired course of treatment may include angiogenic and/or surgical treatment of the occlusions or partial occlusions or other abnormalities, alone and/or in combination with other treatments such as angioplasty, stenting, venous occlusion and/or bypass. In some embodiments, if no occlusions or partial occlusions are identified in the supporting vasculature, angiogenic or other treatments may be focused into the cavernosal spaces and/or surrounding penile anatomy.

In various embodiments, combining penile perfusion studies with imaging and analysis of artery and/or venous stenosis and/or the degree of degenerative tissue disease (and possibly diffusion and/or spectroscopy data) may describe a "new" etiology for subsets of patients with erectile dysfunction and related conditions.

In one exemplary embodiment, subjects could be scanned using combinations of Magnetic Resonance Imaging (MRI) and Magnetic Resonance Angiography to (MRA) to assess the condition and/or treatability of their pathology. Exemplary 3D Contrast enhanced MRA scans could be acquired with 50 coronal slices using TR:5.1 ms, TE:1.78 ms, voxel size=0.8×0.8×1.5 mm$^3$, SENSE:4. Data acquired in this method could be assessed and/or combined in various ways. For example, the blood supply and/or drainage vessels could be modeled, with the supply and/or drainage vessels on MRA potentially graded as occluded, stenotic or open (or other more graduated assessments could be applied). If desired, relevant tissue locations within the penile structures could be graded (in a manner similar to Pfirrmann, or other tissue/vascular grading systems). The conditions of the circumferential structures of the corpus cavernosa could be analyzed and graded. Image data reflecting the structure and/or perfusion of the various capillary vessels and/or microvasculature in the penile tissues could be assessed. In addition, the peripheral branches and/or various arterial blood sources can be analyzed and graded as occluded, stenotic or open (or other more graduated assessments could be applied), and potentially assessed as to whether they could be sufficient to compensate for an ischemic primary blood supply vessel. In addition, MRI and MRA data sets could be overlaid and/or combined to create composite data maps, including the use of color mapping to identify relevant features of interest.

Diagnosis and Treatment

Once an area of hemodynamic imbalance, deficient nutrition, vascular perfusion and/or other anatomy of interest has been identified and analyzed, it may be desirous to treat the area (or other relevant anatomical structures) in an attempt to slow, halt and/or reverse the condition and/or the progression of diseases that may be present and/or develop in the future.

As used herein, the terms "treating," "treatment," "therapeutic," or "therapy" do not necessarily mean total cure or abolition of the disease or condition. Any alleviation of any undesired signs or symptoms of a disease or condition, to any extent, can be considered treatment and/or therapy. It is entirely possible that "treatment" consists of a temporary improvement of the hemodynamic balance of the penile vasculature that may require repeated treatments over time to continue the regenerative process. Alternatively, the "treatment" may only marginally improve the hemodynamic balance of the penile system, but still may require the use of additional therapies (i.e., PED-5 inhibitors and/or physical assist devices) for the patient to achieve an acceptable erectile response. In addition, asymptomatic erectile dysfunction and/or pelvic vascular deficiencies (including prophylactic treatment) may be the focus of treatment utilizing angiogenesis. Furthermore, treatment may include acts that may worsen the patient's overall feeling of well-being or appearance.

In accordance with at least one embodiment hereof, a patient may benefit from use of a PDE-5 inhibitor, such as VIAGRA, after the revascularization procedure, even if that patient had previously experienced a suboptimal response to administration of the same PDE-5 inhibitor prior to the revascularization procedure. Thus in accordance with an embodiment hereof, a method of treating erectile dysfunction that is caused by vascular disease occurring anywhere along the arterial path from the abdominal aorta through the internal pudendal artery includes the step of performing a revascularization procedure (which may include an angiogenic treatment) at a stenosis in one of the pelvic arteries and thereafter the step of administering a pharmaceutically effective amount of a PDE5 inhibitor for use when sexual intercourse is desired. The increased blood flow achievable by the revascularization procedure may help to restore proper function to compromised endothelium downstream of the treatment site, i.e., endothelium that due to insufficient blood flow may have been producing negligible or inadequate NO for driving the erection process, such that a subsequently administered PDE-5 inhibitor will achieve a favorable or even an optimal response, and/or an improved response not previously realized by a patient on the PDE-5 inhibitor alone. The patient's improved response to the PDE-5 inhibitor after the revascularization/angiogenic procedure may include a quicker response time and/or sensitivity to the drug and/or increased tumescence. With blood flow restored and able to flow into the penis faster, a benefit of improved smooth muscle cell relaxation in the corpus cavernosum may be realized, as well as an improved compression of venous system, thus desirably less leaks that would inhibit tumescence.

Figure 8:
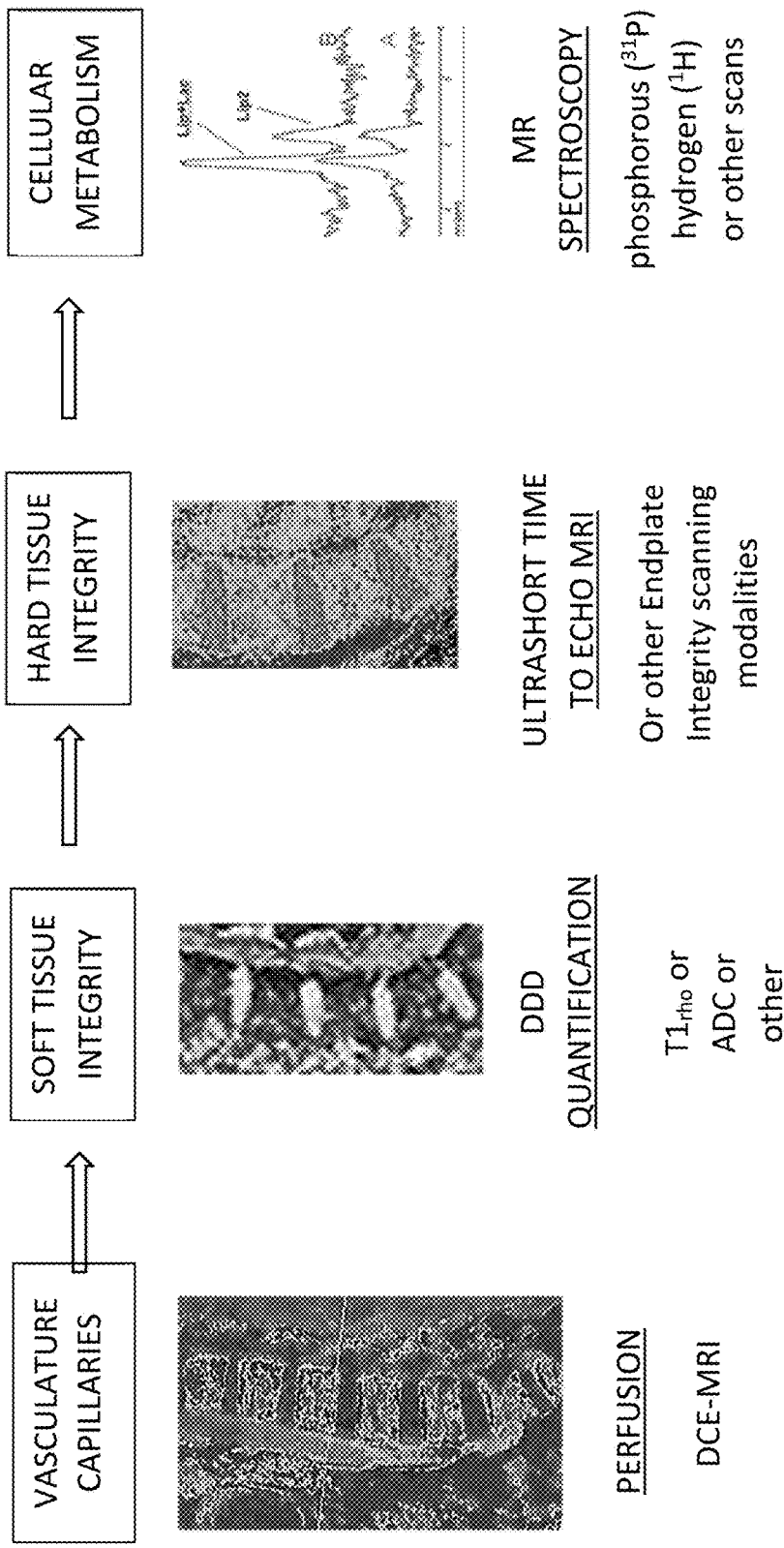
FIG. 8 depicts various imaging modalities that may be useful in obtaining penile and/or pelvic tissue data.

Once an area of hypoperfusion or other deficit is identified as described herein, the patient may be diagnosed with hypoxic and/or ischemic tissue disease, and various embodiments include the induction of neovascularization so as to enhance blood flow and/or localized perfusion to the area of need. In the case of a diagnosis of a hemodynamic imbalance and/or vascular conditions relevant to erectile dysfunction, various embodiments include the induction of neovascularization so as to enhance localized perfusion to the area of need. If desired, quantitative measurements of diffusion weighted imaging and Apparent Diffusion Coefficient or ADC can be utilized to identify "at risk" vasculature or other tissues (which could also include determining the degree of such hypoperfusion and/or utilizing such information to verify the identity and/or location of "at risk" vasculature). Alternatively, or in addition to such ADC measurement and assessment, vascular and/or tissue integrity imaging using either Ultra-short TE (UTE) imaging of the penile tissues and/or pelvic region, assessment of proteoglycan content of pelvic tissues using T1ρ magnetic resonance imaging quantification, measurement of lactate removal by a "metabolite imaging" technique such as Magnetic Resonance Spectroscopy (or 1H-MRS) or phosphorus scanning such as 31P-MRS for pH or bioenergenic metabolism of relevant penile tissues, or similar assessment methodologies could be employed. In other embodiments, various combinations of the above-reference data could be combined with hemodynamic analysis of the penile system and/or tissue condition/vascularity (i.e., including the condition of the veins within/adjacent to the walls of the corpus cavernosum) and any information regarding the change in the symptoms and other clinical factors of the penile tissues or related anatomy to define the medical necessity for angiogenic treatment. The totality of these imaging modalities can be summed up by the process of imaging the entire blood and/or nutrient delivery pathway to and from the penile anatomy. At any point in the blood supply and/or drainage, blood and/or nutrient delivery has the potential to be halted and the hemodynamic balance, integrity and bioenergetics of the penile system affected. Measuring the level of any blockage, constriction and/or local or systemic vessel degradation and its resultant effect on the penile blood flow can potentially be accomplished using any combination of one or more of the imaging modalities of FIG. 8, where vascular and/or penile tissue perfusion can be measured with DCE-MRI, soft tissue integrity and diffusion characteristics analyzed with T1ρ and ADC, hard tissue integrity quantified with ultrashort time to echo MRI (or some other tissue integrity scanning modality) and cellular metabolism measured with some form of molecular imaging such as lactate or sodium.

In various embodiments, angiogenic treatment may be optimized for use in vascular channels and/or tissues that have significant occlusions and/or calcification, while in other embodiments angiogenic treatment may be optimized for use in vascular channels and/or tissues that do not have significant occlusions and/or calcification. For example, it is believed that calcification and/or other vascular conditions may significantly contribute to the loss of venous compressibility (rendering less effective the desired restriction of blood outflow during tumescence) in the tissues surrounding the corpus cavernosum, which may lead to excess blood leaving the penis during an erectile attempt and leading to erectile failure. However, such deficiencies may only affect localized regions within the penile tissues, which may allow an opportunity for a treatment to be utilized that isolates some portion of those deficient regions of venous drainage, desirably allowing less damaged regions of the penis to provide more efficient and/or effective blood outflow control. If desired, angiogenic treatments may be provided that increase the density of the venous plexus in such less damaged regions, while vaso-occlusion techniques (such as those described herein) could optionally be utilized to isolate one or more of the damaged regions. Regardless of the frequency of such calcification, however, various embodiments described herein include desirably restoring perfusion to the penile anatomy (as described herein), which may ultimately provide sufficient blood, oxygen, nutrients and/or waste flow to maintain a minimum or acceptable nutrition level and reverse, reduce and/or slow any degradative cascade of the pelvic anatomy which may result in and/or exacerbate a patient's erectile deficiency. Moreover, the various methods disclosed herein could be utilized for assessing and/or treating diseases such as Peyronie disease, which affects the tunica albuginea, the effects of which may lead to inadequate compression of the emissary veins and a resultant venous leak.

In various embodiments, angiogenic effects induced in a patient by the various treatments described herein have the potential of creating one or more of the following: (1) a localized improvement in the vasculature and/or microvasculature of the penis and related tissues (or other anatomical locations, including non-extremity areas) proximate to the penile tissues, (2) a systemic or localized improvement by artificially inducing the body to create a collateral flow around an occlusion or blockage in the vasculature of the pelvic region (i.e., artificially inducing a "natural bypass" to the restricted and/or blocked vasculature), (3) a regional or localized improvement in volume of blood flow by artificially inducing the body to create a parallel flowpath to existing vasculature in the pelvic region and/or create a new vascular flowpath from a source location to a destination location (i.e., a new blood pathway not previously directly connected), (4) a larger volume and/or density of blood vessels in the vascular network leading to the penile tissues, with a commensurate increase in the number and/or density of endothelial cells contained therein (and enzymes and/or other chemicals produced thereby), and/or (5) various combinations thereof. For example, the angiogenic effects of FGF-1 might induce the vasculature and/or capillaries to grow more proximate and/or closer to an area of damaged and/or undernourished tissue (i.e., recruiting blood vessels into previously unperfused/underperfused regions or regions where perfusion has become deficit), which desirably reduces the distance that nutrients and/or oxygen must travel via diffusion into various tissues. In other embodiments, the angiogenic effects might induce the vasculature and/or capillaries to grow more densely in areas proximate and/or closer to a treated region, which could potentially increase the overall availability and/or concentration of enzymes, blood, nutrients and/or oxygen for use by the various vascular channels and/or the penile tissues (which may include tissues located remotely from the more densely grown region). In still other embodiments, the angiogenic effects might induce the vasculature to supplement, repair, bypass and/or reroute a damaged and/or degraded area of vasculature and/or microvasculature, thereby potentially improving localized and/or systemic vascular flow into and/or out of the penile tissues and/or other anatomical area of the patient's body. In another embodiment, the angiogenic effects might induce the vasculature to open compressed vascular pathways, thereby potentially improving local and/or systemic vascular flow within the extremity and/or other anatomical area of the patient's body. In another embodiment, the angiogenic effects might induce growth of the vasculature and/or microvasculature towards healthier and/or larger sources and/or areas of the vasculature (i.e., attaching to and redirecting flow from well-perfused vessels to poorly perfused vessels and/or regions), so as to route additional blood, nutrients and/or oxygen to the treatment area. In another embodiment, the angiogenic effects might induce growth of additional vascular linkages and/or interconnections between various penile tissues, as well as between the superficial and deep plexus layers of the dermis and/or other subdermal tissues. In another embodiment, the angiogenic effects might induce the vasculature to create new pathways that can be compressed, constricted, free from endothelial dysfunction and/or otherwise altered and/or modified by the natural erectile processes of the patient's body in a desired manner, which may be capable of compensating for diseased or damaged anatomy and potentially improving local and/or systemic vascular flow within the anatomical area of the patient's body. In other embodiments, various combinations of the previously disclosed angiogenic effects might occur.

In various embodiments, the medical necessity for angiogenic treatment can include identifying a patient with erectile difficulties, correlating a changing quantitative measurement of penile tissue degeneration (with either proteoglycan quantification via T1ρ imaging, ADC, or other quantification techniques) along with diminishing vascular inflow, altered venous outflow and/or increased venous outflow, and optionally assessing the presence and/or absence of vascular calcification and/or other degenerative conditions within the vasculature and/or the penile tissues.

In various embodiments, treatments such as those described herein may be desirous even where a patient has not yet experienced a significant loss of erectile function, and/or where a perfusion analysis does not identify a significant hemodynamic imbalance of the penile tissues. In such instances, a diagnosis of "Pelvic Vascular Disruption," non-ischemic priapism, ischemic priapism, diabetes induced ED or similar pathology could be assigned to the relevant tissue structures, even where MRI of the penile tissues themselves do not directly indicate a vascular mechanism, and/or where x-rays of the pelvic anatomy appear normal. In addition, many new syndromes could potentially be defined by these imaging parameters, including various quantitative measures of vascular health, integrity, metabolism and vascular conditions. In various embodiments, the medical necessity for angiogenic treatment could be based upon various applications and various combinations of these objective data.

In various embodiments, 2D and/or 3D imaging studies could be employed to define the specific and/or localized areas of the vascular circulation and/or penile/pelvic anatomy that could be best treated with angiogenesis. If one side (left or right) of a blood supply/drainage analysis and/or corpus cavernosum appeared relatively normal relative to a desired imaging quantifier and/or assessment, and the other side appeared "at risk," one potential treatment approach could be to provide an angiogenic injection within and/or proximate to the "at risk" area (i.e., injection to only the deficient vasculature and/or corpus cavernosum). In alternative embodiments, it may be desirous to treat the "normal" or "healthier" area in an attempt to improve perfusion and/or prevent degradation in that level/area, such as where the venous plexus tissues of the corpus cavernosum periphery on one side of the penis are severely calcified and/or non-functional, while those of the "healthier" side have greater functionality. Desirably, a combination of various treatments will desirably restore and/or regenerate tissues of one or both areas (or at least improve such vascularity and/or tissue condition in one or more areas) and produce resulting improvements in perfusion, hemodynamic balance and/or nutrient/waste delivery/removal.

In various embodiments, one or both of the corpus cavernosa could show diminished perfusion in their supply system. As each penis typically has both a medial and a lateral corpus cavernosum, it is possible that one or the other cavernosal tissues (and/or the vascular supply and/or drainage thereof) could be treated first and imaging measured for improvement before the other tissue location was treated. Depending upon the level of hemodynamic imbalance, in various embodiments it may be possible for the treatment of a single corpus cavernosum to provide sufficient alteration of the hemodynamic imbalance in the penis to allow a patient to achieve an acceptable erection, which may be due to an acceptable level of tumescence within only a single corpus cavernosal cavity and/or may be due to sufficient cross-flow between the medial and lateral corpus cavernosum for an erection to be achieved after treatment.

In various embodiments, more than one location within the pelvic vasculature and/or penile tissue region(s) may be identified as damaged and/or "at risk" and/or in need of treatment. In this situation, imaging data may provide insight as to which location(s) should be accessed for angiogenic treatments first, which in some situations may be an "upstream" region of the vasculature. In such cases, a single angiogenic treatment or other intervention (i.e., angioplasty) may be used for the identified location, or multiple angiogenic injections may be provided to one or more localized areas, including to upstream and/or downstream locations within the vasculature and/or medial, lateral, anterior, posterior and/or centralized injection sites within the penile tissues. In various embodiments, a single surgical pathway may be used to access one or more locations within the targeted pelvic region(s), or multiple vascular and/or surgical access paths may be used for access, intervention and/or injection paths.

In various embodiments, an imaging study of a patient's penile tissues and/or pelvic regions may be performed, and analysis of vascular structures supplying and/or draining the penile anatomy (i.e., proximate to the relevant penile structures) may be emphasized. Such studies can identify "at risk" tissues and/or vasculature, which may be diagnosed for treatment and/or further study at a later date. Where "at risk" tissues or vasculature may be identified, further studies may be performed, if desired.

In one exemplary embodiment of the invention, a patient can be diagnosed with hypoxic and/or ischemic tissue disease and treated by increasing localized perfusion through the use of angiogenesis induction. The process of new blood vessel formation (angiogenesis) can occur naturally, or be induced through various means, include (but not limited to): vasculogenesis, arteriogenesis, and angiogenesis. For the purpose of this invention, all three will be referred to as "angiogenesis". Technically speaking, angiogenesis is associated with de novo capillary and arterial formation from pre-capillary arteries and arterioles and from post-capillary venules, is ischemia- and hypoxia-driven, and is associated with a 2-3 fold increase in blood flow. Angiogenesis can also include growth of or from existing capillaries.

Arteriogenesis is technically considered remodeling of pre-existing vascular channels (collaterals) or de novo artery formation, it can be stimulated by local changes in perfusion (shear stress), as well as cellular influx and proliferation, and associated with a 20-30 fold increase in blood flow. Vasculogenesis is technically considered on the one hand to encompass embryonic vascular development, and on the other hand to include de novo formation or remodeling of pre-existing vascular channels initiated by circulating vascular precursor cells; furthermore; it is considered to be ischemia and injury initiated. The term "angiogenesis" is meant to encompass all three technical terms.

Angiogenesis is known to occur physiologically during zygote implantation, embryogenesis, post-embryonic growth, and during tissue repair and remodeling. Pathologically, uncontrolled angiogenesis is associated with a variety of diseases such as macular degeneration, diabetic retinopathy, inflammation, including arthritis and psoriasis, and cancer. One common aspect of adult angiogenesis is tissue hypoxia. In situations of tissue expansion, cells are typically dependent on the microvasculature for nutrients and oxygen supply, as well as removal of metabolic waste products.

Accordingly, during tissue growth, cells begin to "sense" a lack of oxygen. This triggers a cascade of events that culminates in angiogenesis. During pathological conditions, such as the conditions associated with hypoxic and/or ischemic disc disease, the lack of oxygen is induced through hypoperfusion. Said hypoperfusion may occur due to, for example, atherosclerosis. In some pathological conditions, the normal angiogenic response to hypoxia is absent or substantially diminished.

Although numerous methods of physiological stimulation of angiogenesis under hypoxia are known and could potentially be useful for the practice of the current invention to varying degrees (depending upon the level of response that can be induced), one of the most well characterized pathways involves activation of the Hypoxia Inducible Factor-1 (HIF-1), transcription factor. This protein is only functionally active as a heterodimer consisting of HIF-1a and HIF-1β, which are both basic helix-loop-helix proteins. While the latter is known to be relatively stable, the former has a half-life of less than 5 minutes under physiological conditions due to rapid proteasomal degradation by the oxygen sensitive von Hippel-Lindau (VHL) E3-ubiquitin ligase system. When cells experience hypoxia, HIF-1a half-life is increased since the degradation by VHL E3-ubiquitin ligase is dependent on proline hydroxylation, which requires molecular oxygen. Therefore, this protein modification plays a key role in mammalian oxygen sensing. Activation of this transcription factor leads to gene expression of numerous angiogenesis related genes such as VEGFs, FGF-2 response genes, notch signaling, and up regulation of stromal derived factor (SDF-1), which chemoattracts endothelial precursors during angiogenesis. There are numerous variations by which angiogenesis can occur; however, the basic steps involve remodeling of the extracellular matrix through matrix metalloproteases (MMPs), chemoattraction of either precursor endothelial cells or existing endothelial cells from an adjacent vessel, proliferation of the endothelial cells, tube formation and stabilization. Various embodiments described herein can include the transfection of genes encoding HIF-1 into areas of hypoperfusion and/or tissue degeneration in order to induce normalization of perfusion, or in some cases hyperperfusion in order to ameliorate or significantly treat hypoxic and/or ischemic tissue disease. Embodiments described herein relate to utilization of molecules that either induce the expression of HIF-1, or conversely delay the degradation of HIF-1 or components thereof including but not limited to FGFs.

The term "therapeutically effective amount" of a compound is used herein to indicate an amount of an active compound, or pharmaceutical agent, that elicits the biological or medicinal response indicated. This response may occur in a tissue, system, animal or human and includes alleviation of the symptoms of the disease being treated. The exact formulation, route of administration and dosage for the composition and pharmaceutical compositions disclosed herein can be chosen by the individual physician in view of the patient's condition. (See e.g., Fingl et al. 1975, in "The Pharmacological Basis of Therapeutics", Chapter 1, which is hereby incorporated by reference in its entirety). Therapeutic treatments can be achieved with small molecule organic drugs or biologics, such as proteins. Typically, the dose range of a small molecule therapeutic agent is administered from about 0.5 to 1000 µg/kg, or 1 to 500 uq/kg, or 10 to 500 µg/kg, or 50 to 100 µg/kg of the patient's body weight per dose. The dose of a therapeutic protein growth factor, such as an FGF, can be administered to the patient in a variety of ways, including but not limited to topically, subcutaneously, intramuscularly, intravenously and/or intra-arterially, as a solid, gel, liquid, bolus dose and/or by infusion from about 0.1 to 100 µg/kg of the patient's body weight, or 0.3 to 30 µg/kg, or 1 to 3 µg/kg of the patient's body weight per dose. To achieve localized targeted dosing, FGF-1 can be introduce or injected either directly into or adjacent to the ischemic and/or damaged tissue region, preferably either into or as near as practical to the region of ischemia/damage. Localized dose ranges can be from 10 ng/cm$^3$ to 1 mg/cm$^3$, or 100 ng/cm$^3$ to 100 µg/cm$^3$ or 1 µg/cm$^3$ to 10 µg/cm$^3$ of target tissue per dose. Local doses can be administered at each ischemic and/or damaged tissue region. The dosage may be a single one or a series of two or more given in the course of one or more days, as is needed by the patient. Where no human dosage is established, a suitable human dosage can be inferred from ED50 or ID50 values, or other appropriate values derived from in vitro or in vivo studies, as qualified by toxicity studies and efficacy studies in animals.

In various embodiments, one or more doses of a therapeutic agent, such as FGF-1, could be injected directly into one or more ischemic and/or damaged regions of the penile anatomy and/or related vascular supply/drainage system, and if such direct injection is not possible, then applied adjacent and/or as closely as possible to the ischemic/damaged tissue regions, which could include injection into tissues and/or vascular channels. One exemplary ideal dose could be determined based on the approximate volume of an ischemic and/or damaged tissue region, such as a damaged corpus cavernosum, as estimated using MRI or other imaging modality. If such imaging or assessment were not practical, a clinician could set a standard dose per ischemic/damaged tissue based on an average human tissue volume. In various embodiments, an initial dosing goal for FGF-1 could be to achieve a target concentration of 1 to 10 ug of FGF-1 per cm$^3$ (~1 ml) of ischemic/damage tissues. If the specific tissue volume for a given patient can be determined, this value could be converted into dose levels per tissue region or per cm$^3$ of tissue region for each individual patient. For example, one exemplary tissue volume that could potentially be treatable using various aspects of the present invention could include a 1 cm×1 cm×1-2 mm thick volume of damaged and/or ischemic tissues. Alternatively, if an average tissue and/or ischemic/damage tissue volume were determined, a per cm$^3$ dose of such average or actual volume could be used for a patient. In one embodiment, these proposed values could be a dose per treatment day. In other embodiments, efficacy might be improved if weekly or even twice weekly doses were given. For longer term and/or repeated dose treatment of patients, the duration of such long term/repeated dosing could be determined by subsequent MRIs or other imaging of the patient.

Although the exact dosage can be determined on a drug-by-drug basis, in most cases, some generalizations regarding the dosage can be made. The daily small molecule dosage regimen for an adult human patient may be, for example, an oral dose of between 0.1 mg and 500 mg of each active agent, preferably between 1 mg and 250 mg, e.g. 5 to 200 mg or a topical, intravenous, subcutaneous, and/or intramuscular dose of each ingredient between 0.01 mg and 100 mg, preferably between 0.1 mg and 60 mg, e.g. 1 to 40 mg of each ingredient of the pharmaceutical compositions disclosed herein or a pharmaceutically acceptable salt thereof calculated as the free base, the composition being administered 1 to 4 times per day. Alternatively, the compositions disclosed herein may be administered by continuous intravenous infusion, preferably at a dose of each ingredient up to 400 mg per day. Thus, in various embodiments the total daily dosage by parenteral administration could typically be in a range 0.1 to 400 mg. In some embodiments, the compounds will be administered for a period of continuous therapy, for example for a week or more, or for months or years.

Dosage amount and interval may be adjusted individually to provide plasma levels of the active moiety, which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC (high-performance liquid chromatography) assays or bioassays can be used to determine plasma concentrations.

Dosage intervals can also be determined using MEC value. Compositions could be administered using a regimen which maintains plasma levels above the MEC for 10% to 90% of the time, preferably between 30% and 90% and most preferably between 50% and 90%.

The amount of a given composition administered will, of course, be dependent on the subject being treated, on the subject's weight, the severity of the affliction, the manner of administration and the judgment of the prescribing physician.

In various embodiments, it may be desirous to treat an identified deficiency before significant tissue degeneration, damage and/or erectile dysfunction has occurred, even where some portion of the pelvic vasculature appears to be providing normal blood inflow/outflow, oxygen, nutrition and/or waste removal. This can include imaging and analysis of anatomy proximate to the penile anatomy and/or within the pelvic region, that can be performed to quantify whether a discrete region and/or tissue should be treated alone or if multiple regions should be treated together. If desired, the imaging data and analysis could provide an ability to compare and contrast various regions to each other (i.e., medial and lateral corpus cavernosal blood supplies) as well as to compare data over extended periods of time, which could not only help identify tissues at risk, but also identify which vascular and/or tissue elements may be the most contributing to the hemodynamic imbalance for a given patient. This information could help in the treatment approach. In addition, the specific characteristics of the imaging data may demonstrate which vessels and/or tissue architecture may be susceptible to treatment versus other imaging data that shows vascular regions such as capillaries, venules and/or other structures that may be at a stage where treatment may not be as successful. In addition, coupling imaging data with tissue integrity data may provide insight as to how well the vessels would be predicted to grow into a given area of the pelvic region (i.e., proximate to the penile anatomy) and mature into functional vessels capable of providing/removing blood, oxygen, nutrients wastes, enzymes and/or additional NO. Measuring blood inflow and outflow, coupled with analysis of penile tissue integrity and 2-D or 3-D mapping of the relevant vasculature might outline the area, level, side and anterior or posterior aspect of the tissues and/or vasculature to be treated. Depending upon the area and structure(s) to be imaged, the data can be reconstructed and/or generated to map the region of interest into right, left, anterior, posterior, caudal and/or cephalad sections for careful analysis of the greatest ischemic and/or hypoxic and/or damaged region(s) or relative measures thereof.

Another embodiment may provide angiogenic treatments for various regions of the penile vasculature (and/or supply vessels thereof) that may be already degenerative, with components of this degeneration that may be due to vascular hypoxia or ischemia, and the resultant decrease in the necessary nutrients for cellular maintenance, repair and/or desired erectile response. In many cases, the degenerative vasculature may be supplying lower than normal amounts of nitric oxide, which may be exacerbated by the overall reduced blood flow within the vascular region. For the vascular tissues to "heal" (and potentially produce additional nitric oxide), the necessary pathway for the nutrients required for aerobic energy metabolism could be restored. This might entail delivery of FGF-1 directly into the hypoperfused vascular region(s). This treatment may be preoperatively planned with the proper imaging for mapping of the area to be treated. In addition, the FGF-1 (and/or other angiogenic factors or other necessary constituents) can be injected or implanted or laid adjacent to a vascular occlusion and/or blockage using various delivery schemes depending upon the pharmacologic properties of the various angiogenic factors and the consistency and fluid dynamics of their formulations. The treated vessel's healing environment may or may not be further assessed and/or enhanced with serial imaging studies, and subsequent treatment could be modified if necessary. If desired, further treatment with the angiogenic factor could be performed depending upon the clinical and imaging information already obtained and/or that can be obtained during a postoperative period.

Surgical Access, Implants, Instruments and Procedures

In many situations, surgical interventions will be required. Once a targeted anatomical region and intended treatment regimen have been determined and where subcutaneous (or deeper) introduction of an angiogenic substance may be desirous, a surgical access path and procedure will typically be determined. In many cases, the simple injection of drugs, proteins, cells and/or compounds into the vasculature and/or soft tissues can be accomplished using hypodermic needles, catheters and/or other minimally- or less-invasive surgical devices. However, where such injections desirably target specific tissues, where such devices may be utilized proximate to sensitive and/or fragile tissues structures, where such devices must transition through and/or into denser or harder tissues, or where a more invasive surgical intervention is desired, additional surgical techniques and/or tools may be required.

In many cases, minimally-invasive devices such as hypodermic needles and cannulae can be introduced via a needlestick or small incision in the patient's skin and soft tissues, and guided to a desired location within the anatomy using fluoroscopic or other non-invasive types of visualization. For example, if minimally-invasive access proximate to a vascular narrowing or blockage is desired, a non-invasive view of the vessel of interest (and surrounding anatomy) may be taken using a fluoroscopic visualization system such as a C-arm, commercially available from GE Medical Systems. The vessel could be visualized on the scan (which may include the use of contrast agent), and the needle tip could be inserted through the patient's skin and soft tissues and advanced until it is proximate to the desired tissue structure(s). It is possible that intraoperative CT, MRI or ultrasound (or other imaging modalities which may or may not yet be in clinical use) may be used by the surgeon to ascertain, to a greater degree of clarity, the exact position of the device and/or verify the location of delivery of the active drug and/or carrier. If the carrier is not radiopaque, then a sufficient amount of a radiopaque material, such as barium powder, may be mixed with the carrier, angiogenic material and/or other injectable compound to allow fluoroscopic visualization and localization of the compound.

In various embodiments described herein, it may be desirous to inject compositions and/or materials, including angiogenic compounds, into specific and/or discrete locations within a patient's anatomy. For example, where imaging, analysis and diagnosis indicates a compromised vascular conduit, it may be desirous to inject an angiogenic factor into and/or near the conduit in an attempt to produce angiogenesis within the localized region. Depending upon the clinical needs, the injection may simply be into the compromised tissues, or the injection may desirably be proximate to the compromised vascular supply (i.e., in tissues adjacent to the vessel constriction and/or obstruction).

If desired, a method of treating a vascular deficiency could include the mechanical creation of a channel or path within various tissues of the patient's body using a hypodermic needle or other device. Once the needle has been advanced along a path, the needle may be withdrawn while concurrently injecting periodic "bursts" (i.e., boli) or a continuous "string" or strings of an angiogenic compound into the path evacuated by the needle, or the injection may comprise a string-like or tube-like structure with FGF-1 infused and/or embedded therein. The desired path may be continuous or intermittent, as desired, and desirably the compound left behind within the path will induce the eventual creation of a new vascular path (or portions thereof) along the needle track.

In various embodiments of the invention, a direct injection of an angiogenic factor into and/or adjacent to an ischemic vascular and/or tissue region could be performed to produce and/or induce angiogenesis within a desired region and/or along a desired pathway. In other embodiments, it may be desirous to perform a percutaneous injection (which may include image guided approaches) to access a desired region and/or location within a patient's anatomy. In other embodiments, an open and/or laparoscopic approach may be an optimal approach to a targeted location.

In many cases, it may be desirable to utilize an existing vascular conduit (i.e., a blood vessel) to access a blocked and/or occluded region of the vasculature. Depending upon the location and/or condition of the vessel, the desired angiogenic treatment may be administered within the vessel and/or constriction/blockage, or the angiogenic treatment may be administered outside of the vessel, which may include the employment of a catheter incorporating a deployable needle capable of transiting some or all of the vessel wall (i.e., the needle capable of passing from the inside of the vessel where the catheter resides to the outside of the vessel for medication deployment), which can then desirably inject angiogenic factors in one or more locations in tissues about the periphery of the vessel wall proximate to the occlusion and/or constriction. If desired, such a system could be utilized to transit a first vessel that passes adjacent to a second vessel (the second vessel in need of angiogenic treatment but not in a passable condition for the catheter), wherein the catheter needle exits the first vessel and injects the angiogenic compound proximate to and/or within the second vessel.

In various exemplary embodiments, a hypodermic needle and/or direct catheter can be utilized for injection of therapeutic compounds. This injection can be short term (one injection) or be delivered within an indwelling catheter for longer administration. In addition, a device could be introduced into a targeted location within the pelvic region for longer term introduction of factor(s). If desired, combinations of access routes could be utilized, such as to introduce materials to a plurality of locations and/or to assist with identifying and/or targeting desired anatomical regions—i.e., using a vascular access device within a vessel for identifying the location of an occlusion within a vessel, and a percutaneous approach to inject angiogenic factors outside of, but proximate to, the vessel.

In various embodiments, the stimulation of perfusion within the pelvic region can result in the creation of additional vasculature which can perform a variety of functions. For example, where vessel obstructions and/or occlusions have occurred, the additional blood flowing through the additional vasculature can contribute to the hemodynamic balance of the penile tissues and/or improve tissue oxygenation and/or nutrition so as to enhance healing and production of appropriate proteins (and/or other chemicals and/or enzymes) in said vasculature and/or tissues. The creation of additional vasculature can also contribute to an increased production of nitric oxide synthase, which is an enzyme that catalyzes the production of nitric oxide from L-arginine. Where patients may be suffering from chronic endothelial dysfunction (which may be contributing to their erectile dysfunction), the increased amount of nitric oxide resulting from the additional vasculature may be sufficient to relax the smooth muscles lining the arteries, resulting in overall increased blood flow to the penile region. Moreover, the additional vasculature may be more responsive than the existing diseased vasculature to the various signals inducing and/or controlling the erectile cascade, such as the dilation of blood supply vessels within and/or outside of the penile tissues during arousal as well as constriction of drainage vessels at various times, which may significantly improve the patient's erectile response.

In other embodiments, a composition comprising one or more angiogenic factors can be injected at or proximate to ischemic tissues, such as into and/or proximate to penile tissues comprising the corpus cavernosum or corpus spongiosum. Desirably, the angiogenic factor(s) can promote angiogenesis to form new blood vessels and/or extend preexisting blood vessels into the ischemic tissues, which could potentially create additional blood supply sources and/or additional venous drainage networks therein.

One attraction of protein therapy is that relatively small amounts of a very potent therapeutic agent can be injected into the ischemic area of interest to pharmacologically initiate the process of blood vessel growth and collateral artery formation. In addition, from pharmacokinetic data collected from recent studies in the human heart, it appears that once FGF-1 exits a tissue structure it can be largely cleared from circulation in less than 3 hours. This diminishes the risk of FGF-1 stimulating unwanted angiogenesis in other tissues of the bodies where it could potentially promote inappropriate angiogenesis and other adverse physiologic responses.

In various alternative embodiments, genes can be introduced from exogenous sources so as to promote angiogenesis. It is known in the art that genes may be introduced by a wide range of approaches including adenoviral, adeno-associated, retroviral, alpha-viral, lentiviral, Kunjin virus, or HSV vectors, liposomal, nano-particle mediated as well as electroporation and Sleeping Beauty transposons. Genes with angiogenic stimulatory function that may be transfected include, but are not limited to: VEGFs, FGF-1, FGF-2, FGF-4, and HGF. Additionally, transcription factors that are associated with up regulating expression of angiogenic cascades may also be transfected into cells used for treatment of lower back pain. Said genes could include: HIF-1α, HIF-2, NET (norepinephrine transporter gene), and NF-kB (nuclear factor-kappa B). Antisense oligonucleotides, ribozymes or short interfering RNA (ribonucleic acid) may be transfected into cells for use for treatment of erectile dysfunction in order to block expression of antiangiogenic proteins such as IP-10 (Interferon-gamma-inducible 10 kDa protein).

Selection of genes or techniques for introduction of said genes in vivo may be performed in vitro prior to administration so as to allow for methods of screening and selecting the combination that is most angiogenically potent. Testing may be performed by various methodologies known to one skilled in the art. In terms of assessing angiogenic potential, said methodologies include, but are not limited to:

(A) Angiogenic activity may by assessed by the ability to stimulate endothelial cell proliferation in vitro using human umbilical vein endothelial cells (HUVECs) or other endothelial cell populations. Assessment of proliferation may be performed using tritiated thymidine incorporation or by visually counting said proliferating endothelial cells. A viability dye such as MTT or other commercially available indicators may be used.

(B) Angiogenic activity may also be assessed by the ability to support cord formation in subcutaneously implanted matrices. Said matrices, which may include Matrigel® or fibrin gel, are loaded with cells that do not have intrinsic angiogenic potential, for example fibroblasts, transfecting said cells with said genes, and implanting said cells subcutaneously in an animal. Said animal may be an immunodeficient mouse such as a SCID (severe combined immunodeficiency) or nude mouse in order to negate immunological differences. Subsequent to implantation, formation of endothelial cords generated from endogenous host cells may be assessed visually by microscopy. In order to distinguish cells stimulating angiogenesis versus host cells responding to said cells stimulating angiogenesis, a species-specific marker may be used.

(C) Angiogenic activity may be assessed by the ability to accelerate angiogenesis occurring in the embryonic chicken chorioallantoic membrane assay. Cells transfected with angiogenic genes may be implanted directly, or via a matrix, into the chicken chorioallantoic membrane on embryonic day 9 and cultured for a period of approximately 2 days. Visualization of angiogenesis may be performed using in vivo microscopy.

(D) Angiogenic activity may be assessed by the ability to stimulate neovascularization in the hind limb ischemia animal model. In one embodiment, patients diagnosed with hypoxic, ischemic and/or vasculogenic erectile dysfunction could be treated using gene therapy in a localized manner.

In one embodiment, patients diagnosed with hypoxic and/or ischemic erectile dysfunction could be treated using gene therapy in a localized manner. Specifically, the gene for FGF-1 could be administered in a composition of nucleic acid sequences or one or more triplex DNA compounds, and a nonionic block copolymer. The gene administered could be under control of a strong promoter, for example, the CMV (cytomegalovirus) promoter. The nonionic block copolymer may be CRL-8131 as described in U.S. Pat. No. 6,933,286 (which is incorporated herein by reference in its entirety). Specifically, in such an embodiment 300 milligrams of CRL-8131 may be added to 10 ml of 0.9% NaCl and the mixture solubilized by storage at temperatures of 2-4° C. until a clear solution was formed. An appropriate amount of a FGF-1 expressing plasmid diluted in PBS (phosphate buffered saline) could be added to the mixture and micelles associating the copolymer and the compound could be formed by raising the temperature above 5° C. and allowing the suspension of micelles to equilibrate. The equilibrated suspension would be suitable for administration.

In other embodiments it may be desirable to utilize an angiogenesis-stimulating protein for administration in a therapeutically effective amount. Said protein may be selected from proteins known to stimulate angiogenesis, including but not limited to TPO (thyroid peroxidase), SCF (stem cell factor), IL-1 (interleukin 1), IL-3, IL-6, IL-7, IL-11, flt-3L (fms-like tyrosine kinase 3 ligand), G-CSF (granulocyte-colony stimulating factor), GM-CSF (granulocyte monocyte-colony stimulating factor), Epo (erythropoietin), FGF-1, FGF-2, FGF-4, FGF-5, FGF-20, IGF (insulin-like growth factor), EGF (epidermal growth factor), NGF (nerve growth factor), LIF (leukemia inhibitory factor), PDGF (platelet-derived growth factor), BMPs (bone morphogenetic protein), activin-A, VEGF (vascular endothelial growth factor), VEGF-B, VEGF-C, VEGF-D, P1GF, and HGF (hepatocyte growth factor). In some preferred embodiments, administration of the angiogenesis-stimulating protein is performed by injection directly into and/or proximate to a vessel supplying the erectile tissues, while in other embodiments it may be injected into the erectile tissues themselves. In some embodiments, the angiogenic-stimulating protein is co-administered with stem or progenitor cells.

In some embodiments a carrier solution or containing/metering device may be desired. Appropriate carrier solutions may be selected based on properties such as viscosity, ease of administration, ability to bind solution over a period of time, and general affinity for the agent delivered. Said solutions may be modified or additives incorporated for modification of biological properties. Starting solutions may include certain delivery polymers known to one who is skilled in the art. These could be selected from, for example: polylactic acid (PLA), poly-L-lactic acid (PLLA), poly-D-lactic acid (PDLA), polyglycolide, polyglycolic acid (PGA), polylactide-co-glycolide (PLGA), polydioxanone, polygluconate, polylactic acid-polyethylene oxide copolymers, polyethylene oxide, modified cellulose, collagen, polyhydroxybutyrate, polyhydroxpriopionic acid, polyphosphoester, poly(alpha-hydroxy acid), polycaprolactone, polycarbonates, polyamides, polyanhydrides, polyamino acids, polyorthoesters, polyacetals, polycyanoacrylates, degradable urethanes, aliphatic polyester polyacrylates, polymethacrylate, acryl substituted cellulose acetates, non-degradable polyurethanes, polystyrenes, polyvinyl fluoride, polyvinyl imidazole, chlorosulphonated polyolefin, and polyvinyl alcohol.

Administration may be performed under fluoroscopy or by other means in order to allow for localization in proximity of the cause of hypoperfusion. Acceptable carriers, excipients, or stabilizers are also contemplated within the current invention; said carriers, excipients and stabilizers being relatively nontoxic to recipients at the dosages and concentrations employed, and may include buffers such as phosphate, citrate, and other organic acids; antioxidants including ascorbic acid, n-acetylcysteine, alpha tocopherol, and methionine; preservatives such as hexamethonium chloride; octadecyldimethylbenzyl ammonium chloride; benzalkonium chloride; phenol, benzyl alcohol, or butyl; alkyl parabens such as methyl or propyl paraben; catechol; resorcinol; cyclohexinol; 3-pentanol; and mecresol; low molecular weight polypeptides; proteins, such as gelatin, or non-specific immunoglobulins; amino acids such as glycine, glutamine, asparagine, histidine, arginine, or lysine; monosaccharides, disaccharides, and other carbohydrates including glucose, mannose, or dextrins; chelating agents such as EDTA (ethylenediaminetetraacetic acid); sugars such as sucrose, mannitol, trehalose, or sorbitol; and/or salt-forming counter-ions such as sodium. For heparin-binding proteins, including FGFs, heparin may be incorporated into the formulation, which can bind and stabilize the protein against inactivation and degradation.

In various embodiments, treatment of hypoxic and/or ischemic erectile dysfunction could include the use of a biocompatible or biodegradable implant. Said biodegradable implants can contain a biodegradable delivery system, or carrier, as well as angiogenic factors; said angiogenic factors could be capable of stimulating sufficient neovascularization to overcome local hypoxia. One preferred angiogenic factor is fibroblast growth factor 1 (FGF-1). However, other recombinant naturally derived, in vitro derived, and in vivo derived angiogenic factors may also be used. In some embodiments, the biodegradable implant which contains said angiogenic factors contains a carrier. The carrier is preferably chosen so as to remain within the implanted site for a prolonged period and slowly release the angiogenic factors contained therein to the surrounding environment. This mode of delivery allows said angiogenic factors to remain in therapeutically effective amounts within the site for a prolonged period. By providing said angiogenic factors within a carrier, the advantage of releasing said angiogenic factors directly into the target area is realized. In some embodiments, the implant's carrier is provided in an injectable form. Injectability allows the carrier to be delivered in a minimally invasive and preferably percutaneous method. In some embodiments, the injectable carrier is a gel. In others, the injectable carrier comprises hyaluronic acid (HA).

In some embodiments, the carrier of the graft comprises a porous matrix having an average pore size of at least 25 micrometers. Preferably, the porous matrix has an average pore size of between 25 micrometers and 110 micrometers. When the average pore size is in this range, it is believed that the porous matrix might also act as a scaffold for in-migrating cells capable of becoming cells stimulatory of angiogenesis in the targeted area. Numerous examples of organic materials that can be used to form the porous matrix are known to one of skill in the art; these include, but are not limited to, collagen, polyamino acids, or gelatin.

Said collagen source may be artificial (i.e., recombinant), or autologous, or allogenic, or xenogeneic relative to the mammal receiving the implant. Said collagen may also be in the form of an atelopeptide or telopeptide collagen. Additionally, collagens from sources associated with high levels of angiogenesis, such as placentally derived collagen, may be used. Examples of synthetic polymers that can be used to form the matrix include, but are not limited to, polylactic acids, polyglycolic acids, or combinations of polylactic/polyglycolic acids. Resorbable polymers, as well as non-resorbable polymers, may constitute the matrix material. One of skill in the art will appreciate that the terms porous or semi-porous can refer to the varying density of the pores in the matrix.

Scaffold structures may be used in some embodiments for anchoring or substantially causing adhesion between said implant and anatomical structures—such anatomical structures may include skin and fascial tissues, bone, cartilage, fats, muscle, nerve, tendon, ligament, other anatomical structures and/or various combinations thereof. In some embodiments, the method of adhering said implant to said anatomical structures may be a gel. Said gel, which may be administered alone or together with said implant, can be injected to the graft site, in some embodiments under arthroscopic fluid conditions. The gel can be a biological or synthetic gel formed from a bioresorbable or bioabsorbable material that has the ability to resorb in a timely fashion in the body environment.

Suitable scaffold agents are also known to one of skill in the art and may include hyaluronic acid, collagen gel, alginate gel, gelatin-resorcin-formalin adhesive, mussel-based adhesive, dihydroxyphenylalanine-based adhesive, chitosan, transglutaminase, poly(amino acid)-based adhesive, cellulose-based adhesive, polysaccharide-based adhesive, synthetic acrylate-based adhesives, platelet rich plasma (PRP) gel, platelet poor plasma (PPP) gel, clot of PRP, clot of PPP, Matrigel®, Monostearoyl Glycerol co-Succinate. (MGSA), Monostearoyl Glycerol co-Succinate/polyethylene glycol (MGSA/PEG) copolymers, laminin, elastin, proteoglycans, poly(N-isopropylacrylamide), poly(oxyalkylene), a copolymer of poly(ethylene oxide)-poly(propylene oxide), polyvinyl alcohol and combinations thereof.

In some embodiments, a pliable scaffold could be preferred so as to allow the scaffold to adjust to the dimensions of the target site of implantation. For instance, the scaffold could comprise a gel-like material or an adhesive material, as well as a string-like, tube-like, foam and/or mesh structure. Preferably, said scaffold can be a biodegradable, bioresorbable and/or bioabsorbable material. Said scaffold can be formed from a polymeric foam component having pores with an open cell pore structure. The pore size can vary, but in one preferred embodiment the pores could be sized to allow tissue or angiogenic ingrowth. In some embodiments, said pore size is in the range of about 40 to 900 micrometers. Said polymeric foam component can, optionally, contain a reinforcing component, such as, for example, woven, knitted, warped knitted (i.e., lace-like), non-woven, and braided structures. In some embodiments where the polymeric foam component contains a reinforcing component, the foam component can be integrated with the reinforcing component such that the pores of the foam component penetrate the mesh of the reinforcing component and interlock with the reinforcing component. In some embodiments, said angiogenic growth factors could be predominantly released from a sustained delivery device by its diffusion through the sustained delivery device (preferably, through a polymer). In others, said angiogenic factors could be predominantly released from the sustained delivery device by the biodegradation of the sustained delivery device (preferably, biodegradation of a polymer). In some embodiments, said implant comprises a bioresorbable material whose gradual erosion causes the gradual release of said angiogenic factors. In some embodiments, said implant comprises a bioresorbable polymer. Preferably, said bioresorbable polymer has a half-life of at least one month. Accordingly, in some embodiments, said implant comprises the co-polymer poly-DL-lactide-co-glycolide (PLG) admixed with said angiogenic factors. In various embodiments, a biodegradable or bioresorbable component could provide a location, a scaffold and/or a matrix for growth of vascular endothelial cells and related vascular tissues which, when the component eventually degrades away and/or resorbs, create a new vascular channel in approximately the same location as the original placement of the component.

In some embodiments, the implant could be comprised essentially of a hydrogel. Hydrogels can also be used to deliver said angiogenic factors in a time-release manner to the area of hypoperfusion. A "hydrogel," as defined herein, is a substance formed when an organic polymer (natural or synthetic) is set or solidified to create a three-dimensional open-lattice structure that entraps molecules of water or other solution to form a gel. Said solidification can occur, e.g., by aggregation, coagulation, hydrophobic interactions, or cross-linking. The hydrogels described herein could rapidly solidify to keep said angiogenic factors in proximity to either the blood vessel causative of hypoperfusion, or the area associated with hypoperfusion and/or tissue damage. In some embodiments, said hydrogel could be a fine, powdery synthetic hydrogel. Suitable hydrogels would desirably exhibit an optimal combination of such properties as compatibility with the matrix polymer of choice, and biocompatibility. The hydrogel can include one or more of the following: polysaccharides, proteins, polyphosphazenes, poly(oxyethylene)-poly(oxypropylene) block polymers, poly(oxyethylene)-poly(oxypropylene) block polymers of ethylene diamine, poly(acrylic acids), poly(methacrylic acids), copolymers of acrylic acid and methacrylic acid, polyvinyl acetate, and sulfonated polymers.

In one alternative embodiment, a localized medical device and/or composition could be implanted using an attachment mechanism within and/or onto an anatomical structure that resides at a location adjacent to and/or remote from the area of hypoperfusion, such as within and/or proximal to a blood vessel supplying the area of hypoperfusion (i.e., for example, the vessels that feed to the corpus cavernosa of the penis). In various embodiments, attachment could be performed using an anchoring device; such as employing an anchoring device attaching a medical device to a soft and/or hard tissue structure proximal to a pelvic artery. Said medical device could include an ability to provide time-course release of an angiogenic factor. Said medical device may include a solid casing with an internal gel-like fluid containing the desired angiogenic factor. Said gel-like fluid may be a cryoprecipitate, an administration matrix, or a composition of various polymers suitable for the sustained release of said angiogenesis promoting factor.

In one alternative embodiment, a medical device that adheres or attaches to the proximity of a hypoperfused and/or damaged tissue area for the purpose of delivering the desired angiogenic factor could be placed near or in the proximity of the tissues surrounding one or both of the corpus cavernosum within the penis. This medical device could be a reservoir for the formulation of the active delivered drug that is delivered over time to the penile tissues. This device could be made of synthetic or biologic material, and be implanted within the targeted tissues and/or attached with anchors or have positional stability without anchors.

Various treatments contemplated herein could be in the manner of injection of FGF-1 alone or in a vehicle such as xenograft, allograft, collagen matrix, synthetic, or other scaffolding. If desired, extended slow release dosing can allow continuous delivery of a small molecule or protein, thereby avoiding the concentration peaks and troughs of intermittent oral or bolus injectable doses. This can be achieved using a pump or either an injected or implanted polymeric gel. Injected biodegradable matrices could include, but are not limited to, those containing one or more of the following: heparin, collagen, gelatin, fibrin, and alginates.

In addition, various alternative embodiments contemplated herein include the use of angiogenic factors, tissue graft implants and/or other biological treatments (i.e., stem cell therapy, etc.), either alone or in various combinations, for treatment of other anatomical tissues. Angiogenic treatments can also be used in conjunction with other treatments, such as introduction and/or injection of stem cells, which may be embryonic stem cells or adult stem cells. Such angiogenic treatments could be used to prepare tissues for subsequent injection of stem cells, or angiogenic compounds could be injected concurrently with and/or after introduction of such cells. With regards to penile tissues or other tissues, growth factors, synthetic or treated allograft or xenograft tissue for scaffold (or extra-cellular matrix) and stem cells (each of which could be used separately or in varying levels of in combination with each other) could be utilized to "engineer" or otherwise modify tissues with the goal of regenerating living tissue. If the damaged tissue(s) to be treated required that ischemia or hypoxia related causes needed to be diagnosed and treated first or in combination with the tissue engineering techniques (or if such treatment could be optimized if such approaches were employed), then the diagnosis and treatment could be for ischemic tissue conditions or other pathologies such as described herein.

In addition, it may be determined that a combination of stem cells, engineered tissue, scaffold and/or growth factors (or various combinations thereof) could be enhanced by combining angiogenic factors such as FGF-1 in its native state or through an FGF-1 mutant (i.e., through protein engineering technology) or any other appropriate angiogenic factor. In this embodiment, the regenerative implant would desirably be selected and/or designed to not over-utilize the nutrients available in the wound bed. A limiting factor of regenerative therapy may be nutrient availability, oxygen supply, diffusive transport limitations and/or waste disposal constraints on any therapy that seeks to increase the local anatomical cellular population and metabolic rate. In combination therapy, nutrient delivery to the affected tissues may be desirably enhanced through increasing the population and/or density of vasculature and/or microvasculature.

Combination therapy could also include tissue engineered material that is transplanted into a wound bed made available by removing some or all previous degenerative wound material and/or healthy tissues. To provide nutrients for this transplant, angiogenic therapy, with or without concurrent tissue grafting and/or tissue reconstruction, if needed, could be included. In addition, this combination therapy could be further enhanced with growth factors or other signaling molecules and embryonic or adult stem cells and various types of scaffold. The preoperative planning could desirably map the areas to be treated. Preoperative imaging, modeling and/or assessment, as described before, could be used to analyze the metabolic demands of the combination transplant and the state of the nutrient pathway that is required to support the transplant. Detailed preoperative planning, using imaging modalities already discussed (or imaging modalities not yet invented or used for this type of procedure) of the nutrient demands of the transplant and the subsequent translation of this imaging data into the proper amount, delivery, vehicle, approach, whether existing tissues should be altered and/or perforated, thinned or otherwise reconstructed to improve diffusion, what other anatomical areas might require treatment and how that information impacts the treatment plan and other yet unknown factors could all be information utilized when planning the regenerative therapy.

FGF-1s can be used in which one or more amino acid insertions, deletions or substitutions are introduced by standard genetic engineering techniques, such as site-directed, deletion, and insertion mutagenesis. The wild type FGF-1 three-dimensional conformation is known to be marginally stable with denaturation occurring either at or near physiologic temperature. FGF-1 binding to heparin increases the thermal inactivation temperature by approximately 20 C. Therefore, FGF-1 is typically formulated with therapeutically approved USP heparin. However, heparin is an anticoagulant that can promote bleeding as a function of increasing concentration. In addition, some individuals have been immunologically sensitized to heparin by previous therapeutic exposure, which can lead to heparin-induced thrombocytopenia and thrombotic events. Mutations that extend the storage stability in vitro and biologic activity in vivo would allow FGF-1 to be formulated and dosed in the absence of exogenous heparin. These include mutations that decrease the rate of oxidative inactivation, such as replacement of one or more of the three cysteine residues by either serine or other compatible residues. In particular, as has been described by others, substitution of cysteine 117 by serine is known to substantially increase the half-life of human FGF-1 by decreasing the rate of oxidative inaction. Other mutations have been described that increase conformational stability by making amino acid changes in internal buried and/or external exposed amino acid residues. In the case of repeat dosing regimens, FGF-1s exhibiting greater stability and life-time might effectively decrease the frequency and number of repeated doses needed to achieve sustained exposure and greater efficacy. These stabilized mutants would allow longer duration dosing from slow release polymeric matrices and delivery systems.

Combination therapy could also include tissue engineered material that is transplanted into the penile tissues and/or pelvic anatomy into space made available by removing some or all previous degenerative material. To provide nutrients for this transplant, angiogenic therapy with or without tissue reconstruction, if needed, could be included. In addition, this combination therapy could be further enhanced with growth factors or other signaling molecules and embryonic or adult stem cells and various types of scaffold. The preoperative planning would desirably map the areas to be treated. Preoperative imaging, as described before, could analyze the metabolic demands of the combination transplant and the state of the nutrient pathway that is required to support the transplant. Detailed preoperative planning, using imaging modalities already discussed (or imaging modalities not yet invented or used for this type of procedure) of the nutrient demands of the transplant and the subsequent translation of this imaging data into the proper amount, delivery, vehicle, approach, location, orientation, and intended surgical procedure, and how that information impacts the treatment plan and other yet unknown factors could all be information utilized when planning the regenerative tissue therapy.

Priapism Assessment and Treatment

In various embodiments, the techniques described herein could also be utilized to diagnose and treat a variety of erectile and/or penile tissue conditions, including tissue injuries and/or undesired erectile conditions such as priapism (which can include male penile priapism as well as female clitoral priapism or clitorism). Priapism is an often painful medical condition in which an erect penis does not return to its flaccid state, despite the absence of both physical and psychological stimulation, within four hours. Priapism is considered a medical emergency, which should receive proper treatment by a qualified medical practitioner. There are two types of priapism: low-flow and high-flow. Eighty to ninety percent of clinically presented priapisms are low flow disorders, which involves the blood not adequately returning to the body from the penis. High-flow priapism typically involves a "short-circuit" of the vascular system partway along the penis. As with most medical conditions, early treatment can be beneficial for a functional recovery.

Treatment of priapism is different for each type, but currently there are no quick and easily used methods to determine what cause and/or type of priapism that is being presented. The causative mechanisms are poorly understood but involve complex neurological and vascular factors. Priapism may be associated with hematological disorders, especially sickle-cell disease, sickle-cell trait, and other conditions such as leukemia, thalassemia, and Fabry's disease, and neurologic disorders such as spinal cord lesions and spinal cord trauma. In general, a patient presenting with priapism is immediately orally administered pseudoephedrine or a similar medication, pseudoephedrine being an alpha-agonist agent that exerts a constriction effect on smooth muscle of the corpus cavernosa. If this initial treatment is ineffective, then a specialist is required to aspirate blood from the corpus cavernosa under local anesthetic. If this is still insufficient, then intracavernosal injections of phenylephrine are typically administered, which should only be performed by a specialist trained in the procedure, with the patient under constant hemodynamic monitoring, as phenylephrine can cause severe hypertension, bradycardia, tachycardia, and arrhythmia. In many cases, this "stepwise" approach to treatment will add a significant delay to the eventual resolution of the priapism, which can increase the extent and degree of any injury suffered by the patient.

In various embodiments specifically relating to the treatment and resolution of priapism, imaging and analysis of the penile blood flow can be accomplished. Once a proper hemodynamic model has been created that incorporates sufficient data to approximate the patient's hemodynamic conditions, the model may be queried and/or examined to determine the cause and/or resolution of the priapism. If desired, the analysis may include modeling of changes in the patient's hemodynamic state, and the model will desirably allow a user and/or the system to alter various structural and/or flow parameters to determine how such changes will affect the overall system. Desirably, such changes can be utilized to model system responses to various intended surgical and/or pharmacological interventions, which can allow the system and/or user to determine an optimal course of treatment for the patient.

Compositions

The various treatments and compositions described herein can comprise a wide variety of materials, including scaffolding materials that incorporate collagen, PLA, and/or fibrin. Fibrin incorporation has an added benefit of bonding readily to FGF-1, consequently significantly increasing the thermal tolerance and "half-life" of FGF-1. For example, where "wild type" FGF-1 has a half-life of approximately 15 minutes at 37 degrees C., heparin bound FGF-1 has a thermal stability to approximately 60 degrees C. and a mitogenic half-life at 37 degrees C. of 24 hours. The longer half-life significantly increases the opportunity for FGF-1 to be utilized in conjunction with a therapeutic treatment. However, even a 1-day half-life could lead to a nearly complete loss of activity during long duration treatments, depending upon the dosing regimen.

In various alternative embodiments, a composition comprising human recombinant fibroblast growth factor-1 (FGF-1141) may be provided in a ready-to-use form and/or formulation, or it could be provided in sterile dropper bottles and/or incorporated into implants, with the composition cooled and/or refrigerated just prior to use, if desired. One exemplary dosage of the composition could comprise 180 µg/ml (~3.0 µg FGF-1 per $cm^2$ of damaged tissue area), which could be injected one or more times and/or administered topically three or more times per week for up to 20 weeks or longer, depending upon a physician's desires. If desired, a periodic and/or continued monitoring of the patient's condition could continue for a period of time, such as for a period of 12 weeks post-treatment.

Fibrin matrices can additionally function quite usefully as adhesives and/or "thickeners" in angiogenic compositions, desirably facilitating placement and/or maintenance of FGF-1 at a desired location of a targeted anatomy. Fibrin can "set up" in situ (in place), filling voids and irregular shapes if desired. Another advantage is that the growth factor can be incorporated at the time of polymerization, which can serve to distribute the FGF-1 throughout the fibrin in a uniform and/or a non-uniform distribution, as desired. The ability to tie the drug delivery and degradation to cellular infiltration can be utilized to tailor the composition delivery to the individual patient's healing rate. Moreover, aside from improving the biological half-life of FGF-1, the binding of the FGF-1 receptor sites to fibronectin can protect the FGF-1 within the fibrin matrix, yet allow for sustained drug delivery from the matrix via leaching, polymer degradation and/or other means.

If desired, an angiogenic composition could comprise a graft material incorporating FGF-1 and a fibrin matrix, with the fibrin matrix, due to its own biological activity, serving as a basic scaffolding material for tissue repair. In one exemplary embodiment, the fibrin could comprise a non-porous or porous matrix (i.e., 12% porosity and 100-200 mm pores). For a porous implant, the levels of porosity, the concentration of the growth factor, and/or the concentration of the fibrin matrix (which can affect the drug delivery rate and/or degradation rate) could be optimized for a particular size and/or shape of tissue, wound and/or anatomical location. Desirably, the graft material could induce complete tissue regeneration, and for a topical penile skin application might even induce dermal filling of any full thickness surface defect, and minimal contraction (i.e., less than 20%). If desired, a pre-molded and/or moldable dressing comprising fibrin and/or other constituents could be utilized for treatment of surface tissues and/or subcutaneous transfer/diffusion of FGF-1. Alternatively, a moldable and/or alterable dressing comprising fibrin could be formed in-situ, with adhesiveness, polymerization, and/or flexural properties of the fibrin matrix being particularized for the skin tissue topography.

Topical Treatments

In various embodiments, a topical treatment of the penile surface anatomy and/or other skin surface location(s) via application of an angiogenic compound may provide significant benefits to the patient, which may include improving the nutrition and/or condition of the penile skin and related subsurface tissues (i.e., vasculature and/or nerves). Moreover, where skin penetration by the angiogenic factor can be achieved, it can be possible for the angiogenic factor to reach underlying tissues of the penis, such as the corpus cavernosum and/or corpus spongiosum and related blood vessel networks.

It has been determined that FGF-1 and related angiogenic factors possess a remarkable ability to promote and heal damage to the integumentary system, which is the organ system that encloses the body and includes skin, hair, nails, and related muscle and glands, as well as surface tissues and skin of the penis. Because much of the integumentary system relies upon diffusive transport of oxygen and nutrition (and also for waste removal) from the vascular system in the body, even minor degradation of the vascular system in the localized region supporting such diffusive transport can severely reduce the integumentary system's ability to protect the body from various kinds of damage, such as acting as a barrier to the external environment, protecting against loss of water, cushioning and protecting deeper tissues, excreting wastes, and/or regulating temperature.

Moreover, loss of oxygen and/or nutrition can cause penile skin structures to degrade, which can result in loss of function and/or sensitivity of the penis. Where a significant interruption to the underlying vascular system occurs, the consequences for the overlying integumentary system (and concurrently the overall health of the organism) can be catastrophic, as a damaged or degraded integumentary system poses a significant risk to the organism of disease, infection and ultimately death.

Because the skin is typically an avascular structure, much of the anatomy of the integumentary system relies upon diffusion for nutrition, oxygen and waste removal. The nutrients and oxygen required to maintain cellular function and viability are supplied to the skin surface by capillary vessels and microvasculature in the subsurface tissue layers proximate to the surface layers. In addition, waste products can be removed via similar mechanisms.

Specifically, while the deeper dermal layers of skin contain heavily vascularized channels, the shallower and/or surface layers of the epidermis rely mainly upon diffusive flow to transport oxygen and nutrients from the blood to the cells of these layers, as well as the transport of various waste products from the cells back to the blood for removal and/or reuse by various other organs. The oxygen, glucose and other nutrients are "dropped off" from the capillaries, and then the nutrients "diffuse" (or otherwise move through the adjacent tissues without being transported in blood vessels) to the adjacent skin cells.

Once glucose and oxygen leave the capillaries, passive diffusion becomes the mechanism of nutrient transport through the intervening anatomical layers. A large concentration gradient may be required for optimal diffusion. The concentration gradient is determined by the utilization of the nutrients by the surrounding tissue population and the concentration of nutrients delivered to the localized anatomical region by the microcirculation. Thus, any decrease in the population of the microvasculature has the potential to create metabolic derangement within the skin layers, leading to degeneration.

Once the nutrients reach the cell, they are taken up and utilized for the manufacture of materials that make up the skin layers. If the cells do not receive enough oxygen, the manufacturing process typically stops and/or significantly reduces. As the nutrient supply is cut off, the cells may begin to die, and the thickness and integrity of the skin tissue can begin to be affected, which may predispose the skin to degeneration and/or damage and/or affect the health and integrity of skin and related tissue structures.

Transport from the vasculature to a cell in the skin tissues is a two-step process. First, materials flow near to their destination via blood vessels. Then they cover the remaining distance from the blood vessels to the cells primarily via diffusion. The time required for diffusion over large distances is often much longer than that needed for vascular flow, because diffusion times grow as the square of distance whereas flow times are merely proportional to distance. Under normal conditions, blood is distributed to the capillary bed through an orderly tree-like system of conduits. From there, normal diffusion distances are highly regulated, often to distances less than 50 or 100 µm, and it is generally accepted that the distance that oxygen and other nutrients can diffuse into a given tissue before being metabolized by surrounding cells establishes a maximum distance for "healthy" cells to exist (i.e., "unstressed" cells receiving a desired level of nutrients and oxygen). For example, in the shallower layers of the integumentary system, the epidermal cells with the highest metabolic demand are found closest to the basal lamina, where the diffusion distance is typically shortest, while the surface or "superficial cells," which are more remotely located from the vasculature, typically are less active and/or are generally inert or dead.

In addition, in the papillary dermis the lymphatic system is a closed system. Consequently, the lymph circulates outside of the lymphatic system and directly "bathes" the dermic elements—this is the "plasmatic circulation" which constitutes an internal means allowing nutritional exchange to take place. The plasmatic circulation which regulates the lymphatic circulation is under the influence of the blood circulation—its exudation is regulated by blood pressure and by the osmotic pressure of fluids, by nervous influences, endocrine influences, cellular metabolism, by the state of constriction and dilation of the vessels, and finally by the release of H vasodilatory substances emitted in large amounts by irritated cell tissue.

Glucose and oxygen are extremely important to the function and viability of skin cells. Regardless of the complex interactions taking place in the various skin layers, however, the fact remains that the supply of nutrients, the removal of waste and the overall health of the integumentary system require an intact vascular supply and microvascular capillary network.

Of all the potential complications affecting the health of the skin, the condition of the underlying vascular support network is arguably one of the most important. Virtually every step in the healing and maintenance processes involving the skin relies upon and/or is directly influenced by the conditions of the underlying vasculature. In many cases, an underlying vascular abnormality and/or insufficiency can significantly reduce and/or eliminate the body's ability to maintain and/or heal the skin. For example, the vasculature is the cells' primary source of oxygen and nutrition, as well as a primary channel for of waste removal. A lack of nutrition can inhibit or prevent normal repair and/or replacement of cellular structures, while insufficient oxygen can result in cell death. In a similar manner, a lack of sufficient waste removal can result in a buildup of wastes within and/or between the cells—potentially degrading and/or inhibiting the cells' ability to function and properly repair damage. Moreover, the vasculature is the primary transport pathway for numerous cells and materials necessary for protection of the organism and repair of the skin and/or any skin wounds—so an interruption in the vascular transport mechanism means an interruption in the availability of these cells/materials as well.

Various embodiments described herein relate to methods for imaging, diagnosing, quantifying, assessing, and/or treating or ameliorating painful and/or degenerative conditions that may include and/or involving the penile skin. Embodiments can include classifications of skin cell and related tissue nutrition deficit, pathological conditions and/or associated degeneration and/or chronic conditions that can be based on specific parameters associated with hypoperfusion, hypoxia, and ischemia. Further embodiments relate to treatments for alleviating the state of hypoperfusion, hypoxia, and ischemia in patients in which alleviation of said hypoperfusion may lead to therapeutic improvement.

In one or more embodiments, penile tissues can be directly treated by application of a topical compound which includes one or more angiogenic substances, such as FGF-1. The topical composition may comprise FGF-1 in a concentration between 0.1 to 100%, and this composition may comprise a powder, a gel, an ointment, a lotion, a cream, an oily solution, a suspension, or a semi-solid, and may be applied directly to the surface of the penis, scrotum and/or groin and/or impregnated or carried by a dressing, bandage and/or other medical treatment applied to the penile or other region(s). A dosage of the composition may be administered periodically over an interval of multiple days, may be administered once a day or may be administered multiple times a day, or in the case of a bandage or dressing containing a reservoir of treatment material, may comprise an essentially continuous or periodic "re-application" over a period of time. The number of administrations per day may be, for example, 2, 3, 4, 5, 6 or more. That is, the administration can be applied on a periodic basis, which could include application each day over the course of a treatment period. The treatment period may extend over a period of time necessary to achieve a therapeutic effect, which may include treatment durations of 14, 28, 42, 70, 91, or 140 or more days.

The topical application of an angiogenic substance, such as FGF-1, to the surface of the penis and/or the surrounding surface tissues will desirably induce an angiogenic reaction in one or more of the tissue layers underlying and/or adjacent to the treated portion of the epidermis, which can potentially increase localized blood flow and/or the effective surface area of the vascular network adjacent to the affected area, as well as induce mitosis (i.e., cell division) or other healing responses of dermal fibroblasts, vascular endothelial cells and/or epidermal keratinocytes. In various additional embodiments, the FGF-1 compound will desirably penetrate the skin surface and induce an angiogenic response from underlying penile tissues, including those tissues responsible for supporting the hemodynamic balance resulting in penile erection. For example, such topical application of FGF-1 may be administered to treat penile necrosis from end-stage renal disease (ESRD) or diabetes mellitus. Such penile necrosis may be caused by ischemic related events due to atherosclerosis of the supply vessels and microvasculature leading to ulcerative lesions.

In various other embodiments, the topical application of an angiogenic substance to the surface of the penis and/or surrounding tissues has the potential for "slowing down" and/or halting the process of degeneration which may lead to erectile dysfunction, which might potentially include localized and/or systemic effects that may alleviate various symptoms of the underlying diseases in a systemic manner—including the effects of chronic venous insufficiency and/or diabetes—by reducing, preventing and/or reversing further deterioration of circulation inside and/or adjacent to the penile anatomy. Even when a progression of damage of vascular vessels could only be slowed by the treatment, such treatment has the potential for slowing the irreversible degradation of the patient's penile anatomy, with attendant improvement on the patient's health, virility and/or self-image.

Where a skin dressing or bandage is utilized as a carrier for the angiogenic compound, the dressing might enhance or otherwise alter application of the angiogenic factor in a number of ways. The absorption of the angiogenic compound can be altered by changing the dressing configuration (pore size, porosity, fiber diameter), the dressing surface (composition, charge, surface energy), the biochemical activity (incorporation of biochemical factors), or the degradation or drug delivery rate of the dressing. In various embodiments, a dressing could include biodegradable elements.

In some embodiments, a combination therapy of the penile tissues could include treatments that desirably increase perfusion in identified area(s), such as by injection of a composition that includes an angiogenic factor, along with topical application of the same or a different angiogenic factor. In preferred embodiments, injection can be directly into healthy tissues proximate to the identified area or areas of hypoperfusion and/or tissue damage. The identified area or areas can be accessed in a variety of ways, including via a transdermal approach with a surgical access and delivery device such as a surgical access needle extending through the patient's skin and overlying soft tissues in a minimally-invasive manner. The composition could then be introduced into the anatomy through the delivery device. Concurrently (or consecutively), penile tissues and/or vasculature could be treated by increasing perfusion in identified area(s), such as by topical application of a composition that includes an angiogenic factor. In preferred embodiments, the composition could be applied to the penile surface and/or to the surface of healthy tissues proximate to the penis, as well as to identified area or areas of hypoperfusion and/or in areas of the anatomy where vessels approach and/or are proximate to the tissue surface. In other embodiments, access could be accomplished via an existing opening and/or orifice of the patient, such as via the meatus opening of the penis and/or the anal sphincter, with the FGF-1 compound contained within a liquid or gel, an implantable "pill" and/or degradable suppository or other delivery device. In still other embodiments, access could be accomplished by utilizing vessel and/or vascular pathways (i.e., angioplasty) via the various arteries, veins and/or other minor vessels. If desired, embodiments could encompass penile tissues treated by various combination therapies concurrently and/or on a serial basis, such as by topical application of a composition that includes an angiogenic factor, followed by injection of a composition that includes an angiogenic factor, and/or by various combinations thereof. In preferred embodiments, topical application and/or localized injection could be proximate to one or more areas of hypoperfusion and/or tissue damage. In other embodiments, introduction of angiogenic compounds could be undertaken into and/or adjacent to other anatomical structures, including major arteries and/or veins supplying/removing blood from/to the affected anatomical structures.

In various embodiments, the treatment of patients could include various combinations of active and/or passive treatment phases, wherein active treatment phases desirably induced a positive effect on healing of the patient's damaged and/or ischemic tissues, which might even include improved healing effects in one of both of the active and/or passive phases. For example, the topical application of an angiogenic compound, including FGF-1, to a skin surface of a patient suffering from vasculogenic erectile dysfunction could significantly increase the rate of resolution of the vascular issues during the active treatment phase (as compare to a placebo or non-treatment group), but can potentially also induce significantly improved healing effects and/or retention of healing effects during a follow-on "non-treatment" phase (i.e., passive treatment phase) after cessation of the active treatment. One exemplary treatment regime for a series of patients could comprise topical application of an angiogenic compound, including FGF-1, to the base of the patients' penis and/or scrotum at a frequency of three times a week, for a period of three weeks. The angiogenic compound can include dosing of 3 µg/cm$^2$ of FGF-1 for each patient. Skin tissues treated with FGF-1 in this manner might be expected to heal ischemic tissues at least 3 to 4 times faster than those treated with a corresponding placebo vehicle. In addition, while the active phase of treatment may only span a period of 3 weeks, the accelerated tissue healing could be expected to continue at the accelerated rate for at least another 3 weeks (without additional topical application of the angiogenic compound), and at 6 weeks the rate of healing of the FGF-1 treated group may revert back to that of placebo patients, but desirably without loss of the vessels already created and/or extended. In another exemplary embodiment, skin surfaces can be treated with a topical application of an FGF-1 composition (i.e., the previously described 3 µg/cm$^2$ of FGF-1), which is applied to the skin and/or surrounding healthy tissue three times a week over a period of 20 weeks, and this treatment should demonstrate superior tissue healing to that of a placebo control. Under this protocol, the healing rates in the FGF-1-treated group are significantly greater (an average of 3 to 4 times faster) than in the vehicle placebo-treated group. In another exemplary embodiment, an angiogenic composition comprising FGF-1 in a concentration of 10 mg/cm$^2$, which can be incorporated into a fibrin matrix, can be applied topically to a skin surface and/or surrounding external tissues, which desirably significantly accelerates the healing process of the skin tissues and/or underlying subdermal tissue structures, and leads to significant improvement in healing.

As previously noted, in various embodiments, an angiogenic compound including FGF-1 might be injected and/or otherwise introduced within the patient's tissue, such as by injection via a hypodermic needle into a subsurface skin structure, the vasculature and/or into underlying and/or adjacent healthy tissues. If desired, concurrent and/or alternating surface and subsurface treatments could be undertaken. In another alternative embodiment, it may be desirous to combine a surface treatment of the penile skin with one or more injections of a compound comprising FGF-1 into the pelvic vasculature, into the tissue region proximate to ischemic tissues, and/or into surrounding healthier tissues.

In various embodiments, it may be desirous to treat an identified deficiency before significant tissue degeneration and/or damage has occurred, even where other adjacent tissues and/or vasculature appear to be providing normal oxygen, nutrition and/or waste removal. For example, where a patient is initially diagnosed with diabetes, PAD or some other disease affecting the vasculature, it could be useful to identify vasculature and/or related tissue locations or regions likely to suffer from the various vascular insufficiencies described herein, such as those conditions resulting in erectile difficulties. In many situations, the specific characteristics of the imaging data may demonstrate which vessels and/or tissue architecture may be susceptible to treatment versus other imaging data that shows capillaries, veins and/or other structures that may be at a stage where treatment may not be as successful. In addition, coupling imaging data with tissue integrity data may provide insight as to how well the vessels would be predicted to grow into the target tissue are (i.e., the tissue region of interest) and mature into functional blood vessels capable of providing blood supply, oxygen, nutrient exchange, blood drainage and/or waste removal.

Prosthesis to Protect and/or Offloading Damaged/Ischemic Tissues

In various embodiment, the diagnosis and treatments described herein can have particularly utility in combination with devices and/or instrumentation and/or procedures that "offload," isolate, protect, limit the mobility of and/or otherwise provide temporary and/or permanent reduction in the localized loading of one or more regions of the pelvis and/or penis. A wide variety of such systems and/or procedures could be utilized in conjunction with the various treatments disclosed herein, which in various embodiments could include offloading devices that concurrently include a dual capability of accepting an insert or replaceable "reservoir" of material for treating an external surface of the penis and/or groin in a desired manner.

In some cases, erectile dysfunction issues can be attributed to a variety of compressive and/or repetitive loading conditions. For example, numerous case reports have been published of bicyclists experiencing erectile difficulties and/or perineal nerve dysfunction that can sometimes resolve with changes in cycling techniques, rest, or use of a softer saddle. Small observational studies have also shown a relatively high prevalence of ED among elite cyclists, who often report penile numbness and changes in sensation after cycling. These effects have been confirmed in pathophysiologic studies that describe compression-related changes in perineal structures, as well as in studies of stationary bicycling, which show a significant decrease in penile blood flow during seated biking and a return to above normal when the rider stands.

When humans sit, they bear their weight on the ischial tuberosities, or what we have come to commonly refer to as the "sit bones." The ischial tuberosities have no organs attached to them and no nerves or arteries; they are surrounded by the fat and muscle of the buttocks. This area is very well vascularized and allows humans to sit comfortably and safely for hours. In contrast, most bicyclists bear their body weight on a bicycle seat that is not wide enough to support the ischial tuberosities. As a result, they wind up straddling the bike and, in effect, sitting on the internal part of their genitals. The penis (and the female clitoris) is attached deep within the pelvis. It does not end, as it appears to, at the scrotum but rather near the anus. Like the roots of a tree, this internal part of the penis provides stability so that an erection doesn't buckle as the penis penetrates the vagina. In the straddle position, body weight is supported not by the ischial tuberosities but by the ischiopubic rami, the connector bones that join the ischial tuberosities to the pubic bones. Unlike the ischial tuberosity, which has evolved into an optimal location to bear body weight, the ischiopubic ramus is a working area that contains erectile tissue, nerves, arteries, and the urethra. As a result, the bicycle rider bears his weight directly on an area where the nerves and arteries enter the penis. This area is a tube-like structure called the Alcock canal, which lies along the ischiopubic ramus. Straddling compresses the nerves and arteries running through the Alcock canal against the ischiopubic ramus, which frequently results in complaints of numbness in the penile/scrotal area after cycling. Importantly, straddling may also lead to localized atherosclerosis and compromised blood supply to the penis, resulting in erectile dysfunction. Analysis has shown that individuals who cycle at least three hours per week have an odds ratio for developing moderate or complete erectile dysfunction of 1.72—which is considered a "health risk" as it is more likely to cause artery blockage and long-term damage. It is also believed that similar activities and postures, such as horseback riding, can contribute similarly to erectile difficulties.

Since pressure loading can cause and/or continue damage and also further degrade the tissue structures, it is believed that the subsequent angiogenic treatment of the penile tissues and/or underlying vascular insufficiency after such diagnosis could be facilitated by the use of one or more "offloading" systems that alleviate the direct pressure on the ischiopubic ramus and allow normal vascular perfusion. This offloading, which can be utilized in conjunction with the increase in blood flow resulting from various angiogenic treatments, has a significant opportunity to reduce, halt and/or reverse the effects of the earlier degradation.

The combination of angiogenic therapy with tissue offloading devices desirably improves the flow of blood to the penile region while unloading the tissues and supporting vasculature and/or microvasculature mechanically. This desirably optimizes the clinical approach, because the vasculature supplying the penile tissues can still be further damaged and/or compressed by pressure loading, while the nerves, skin and/or tissues can be further damaged by direct loading. Lessening the spot strain on vulnerable tissues can optimize the environment for healing, and the combined efforts to reduce loading and improve local blood flow by administration of FGF-1 or similar angiogenic compounds can stabilize and/or increase the effectiveness of the treatment.

In various embodiments, the imaging and analysis of a pelvic region and related anatomy can desirably be utilized to design and manufacture a customized prosthesis that can be worn by the patient to protect the damaged tissues (or potentially damageable tissues) while allowing a desired level of ambulation and activity. In various embodiments, the imaging and analysis of a patient's vasculature, nerves, bones and related anatomy can be utilized to design and manufacture a prosthesis that desirably "offloads" the susceptible anatomy for the specific patient, and optionally concurrently topically treating the region with an angiogenic composition.

Various embodiments of offloading devices described herein can include the use of computer aided design and/or computer aided modeling (CAD-CAM) systems to model, design and build a prosthesis for use in treating a specific patient's pelvic region. Desirably, prostheses can be constructed using a rapid prototyping ("RPT") process, Direct Digital Manufacturing ("DDM") or other process suitable for manufacturing unique individual units or other devices that would be manufactured either as a one-off or low volume item. Rapid prototyping is the automatic construction of physical objects using solid freeform fabrication. The first techniques for rapid prototyping became available in the late 1980s and were used to produce models and prototype parts. Today, they are used for a much wider range of applications and are even used to manufacture production quality parts in relatively small numbers. Some sculptors use the technology to produce complex shapes for fine arts exhibitions.

In various embodiments, a model of the patient's anatomy can be obtained from image data, which can include anatomical information of the patient's soft and bony structures of the affected region(s). The anatomical model can then be utilized to derive and/or create a prosthesis appropriate for the patient's anatomy and desired activity, which could include the design of a unique prosthesis for the patient as well as the use of a pre-designed prosthesis, which may require manipulating and/or "fitting" of the pre-designed prosthesis to the specific patient's anatomy. Desirably, the model will accommodate the underlying patient anatomy and the desired patient activities (i.e., bicycling, horseback riding, etc.), and may also accommodate subsurface bony features to desirably avoid further damage to the vasculature and/or penile tissues while the prosthesis is being worn by the patient.

To accommodate a desired vascular conduit and/or nerve within the pelvic tissues, one or more openings or depressions can be modeled in the prosthesis which desirably "offloads" the vasculature/nerve(s). Desirably, openings or other features will accommodate the entirety of the vasculature/nerve, as well as an offset or "margin region" surrounding the tissue of interest, which desirably ensures minimization of any "edge effects" and/or prosthesis movement which may negatively affect the performance of the prosthesis. Depending upon the load bearing nature of the tissues and activities desired, the shape and/or depth of the offset may vary, with virtually any shape opening being contemplated, including openings of circular, oval, symmetrical and/or non-symmetrical or any other geometric shape. If desired, the prosthesis body could be formed from a relatively rigid material such as plastic or metal, with a support and/or cushioning material such as closed-cell foam, silicone or rubber included on a skin-facing surface of the prosthesis. In such embodiments, the opening could be formed in the support and/or cushioning material, rather than in the prosthesis body, if desired. In various embodiments, the prosthesis could comprise a bicycle seat or removable seat pad, a pelvic protection device such as a "sports cup" or similar device and/or clothing such as pants or cycle shorts incorporating various removable and/or non-removable inserts.

Once the virtual 3D model (i.e., from the computer aided design (CAD) or animation modeling software) of the prosthesis has been created, it will desirably be transformed by a rapid prototyping machine into thin, virtual, horizontal cross-sections, with the machine creating each cross-section in physical space, one after the next until the model is finished. The virtual model and the physical model will desirably correspond almost identically, but may vary depending on the resolution used in the RPT process. With additive fabrication, the machine reads in data from a CAD drawing and lays down successive layers of liquid, powder, or sheet material, and in this way builds up the model from a series of cross sections. These layers, which correspond to the virtual cross section from the CAD model, are joined together or fused automatically to create the final shape. The primary advantage to additive fabrication is its ability to create almost any shape or geometric feature. A large number of competing technologies are available in the marketplace. As all are additive technologies, their main differences are found in the way layers are built to create parts. Some melt or soften material to produce layers, while others use layers of liquid materials that are cured. In the case of lamination systems, thin layers are cut to shape and joined together. Among the various RPT technologies are selective laser sintering (SLS), direct metal laser sintering (DMLS), fused deposition modeling (FDM), selective laser melting (SLM), stereolithography (SLA), laminated object manufacturing (LOM), electron beam melting (EBM), Laser Engineered Net Shaping (LENS), laser cladding, and 3D printing (3DP).

In various embodiments, the layering of the prosthesis may be particularized to optimize the strength and/or durability of the prosthesis. If desired, individual layers can be cross-weaved to maximize construct strength and/or reduce the potential for weakness or fracture along one or more intra-layers boundaries. In other embodiments, the layering may be particularized such that anticipated stresses loading intra-layer weaknesses can be minimized. For example, a prosthesis for a groin region could be manufactured by layering the material from the medial side to the lateral side of the prosthesis, creating layer lines extending along an anterior to posterior axis that should be highly resistant to forces induced on the prosthesis by the patient's leg compression and movement during pedaling motion and/or "push off" of their foot (i.e., during bicycling activities).

Once the prosthesis has been created by the manufacturing machinery, it could be utilized immediately and/or might require additional post-processing steps such as the addition of one or more layers of support and/or cushioning material (as previously described). Desirably, the finished prosthesis can then be sent to the physician and/or patient for fitting and use.

A prosthesis can desirably incorporate various features to facilitate use of the prosthesis during activities. The prosthesis is desirably customizable to the shape and support requirements of the patient's groin, pelvis and related support structures (i.e., bicycle seat), and in various embodiments the patient's anatomy can be imaged and/or measured, with the image data in various embodiments depicting both the contours and shape of the groin and pelvic region, as well as image data reflecting the underlying soft tissues and/or hard tissues (i.e., bones) of the targeted anatomy. Desirably, the image data can be used to model the anatomy, and potentially identify any hard or soft tissues that may be contributing directly to the vascular and/or nerve compression as well as tissues that may be indirectly contributing to vascular deficiencies by constricting and/or blocking vascular and/or microvascular flow within the penile tissues. Various embodiments can include obtaining perfusion data of the blood flow within the groin and/or pelvic region, and in some embodiments such data could be obtained from the patient's groin while in a weight-bearing condition (i.e., seating on a non-metallic bicycle analog during MRI, etc.), if possible. If desired, additional patient anatomy may be imaged, such as the patient's opposing extremities and/or connecting anatomy, to identify other anatomical abnormalities that might be addressed by proper modeling and design of the prosthesis (i.e., increasing the thickness of the prosthesis to address a gait abnormality).

In various additional embodiments, an insert or other device could be provided that is sized and/or configured to fit within one or more of the openings or depressions in the prosthesis, the insert desirably containing an angiogenic compound as described herein (optionally with other constituents, as described herein). In various embodiments, an insert could include a delivery or "deployment" feature which facilitates dispensing and/or application of the angiogenic compound and/or other constituents to the skin surface in a desired manner, such as through a permeable skin-facing wall of the insert. In various embodiments, the various body movements of the patient could desirably impel such delivery by simple compressive pressure on the insert, or a deployment device, pump or other arrangement could be provided to deliver the angiogenic compound as desired. In various alternative embodiments, the compressive pressure could be applied to peripheral portions of the insert by the healthy tissues at the margin of the opening.

EXEMPLARY TREATMENTS

Ex. 1—Pelvic Imaging and Tissue Treatment

In one exemplary embodiment, a patient experiencing erectile dysfunction or other related anatomical issues can undergo perfusion imaging as described herein that, when analyzed, demonstrates one or more areas of ischemia and/or hypoperfusion proximate to and/or "upstream" from the penile tissues. Further imaging studies could be obtained to analyze the vascular supply to and/or from the penis in detail and potentially identify specifics as to the anterior, posterior, cephalad, caudad, medial/lateral and/or left/right location of the perfusion deficits. One or more tissue perfusion 2D or 3D maps (which could include structural and/or colorized flow maps) could be generated for further detail. Maps prepared using different imaging modalities (i.e., MRA and MRI, for example) or identifying different anatomical characteristics (i.e., images reflecting perfusive flow overlain by images reflecting soft tissue and/or bone structures and/or oxygen levels and/or metabolic waste imaging) could be compared and/or overlain, and the resulting data tabulated and/or analyzed. The physician and/or surgeon could begin planning the proper placement of the angiogenic factor by topical application and/or injection, as well as any associated prosthesis, delivery vehicles and/or therapeutic/vaso-occlusive compounds. The angiogenic factor could be FGF-1 or FGF-1 mutant or other angiogenic factors. The angiogenic factor may be formulated in a variety of vehicles and/or carriers defined for specific surgical needs.

As an example, a vascular deficiency resulting in erectile dysfunction for a patient may require an angiogenic factor in an externally placed vehicle or prosthesis or, alternatively, in a vehicle that requires an anchor or some other attachment device that would allow a broad and stable surface area for delivery of the drug. Various other modifications may be required depending upon the location and/or extent of damage to the relevant tissues of interest. In addition, the location of the damaged and/or compromised tissues may require specific angiogenic formulations, vehicles, matrixes, synthetics, carriers, mutants, attachments, anchors, dosages, repeat doses, delivery devices, image guided delivery and/or targeted delivery selections. In addition, if a portion of a tissue requires repair, replacement and/or was sacrificed as part of the normal treatment or approach to gain access to the drug delivery zone and a reconstruction was required or desired, a tissue graft might be performed at the same time as the angiogenic treatment or in a staged procedure. In addition, if a preoperative defect would require reconstruction prior to the angiogenic treatment, then the reconstruction and/or grafting procedure could be done first and the angiogenesis performed at the same time or in a second stage.

If other regenerative therapy is planned, either tissue based, cell based, gene based or protein based, or some other biologic or synthetic regenerative or tissue engineering treatment, and it was ascertained that the above diagnostic and angiogenic treatment and/or tissue surface reconstruction was desired prior to or during the regenerative treatment, then the above diagnostic and treatment protocol could be performed in concert with the regenerative treatment or in a staged fashion.

Ex. 2—Arterial/Venous Blood Supply Analysis Combined with Microvascular Dynamic Perfusion In various embodiments, the arterial tree and body blood flow (and optionally blood drainage) can be simultaneously and/or sequentially evaluated in the penile tissues or other anatomical region for the purpose of vascular mapping of the penile tissues or other region of interest. The goal of such a study can be (1) to develop a safe and reproducible technique of MRA and perfusion utilizing one injection of contrast, (2) to measure penile perfusion and compare intra-subject and inter-subject results with the degree of vessel stenosis and/or microvascular compromise, (3) to begin evaluating normal controls, and/or (4) to diagnose and/or treat the patient.

In one exemplary embodiment, both MRA and dynamic perfusion imaging can be performed with contrast enhancement. Subject images can be acquired with a Philips Achieva 3T system. For all imaging protocols, a 330 mm*300 mm FOV and a 6-element SENSE torso RF coil can be used. The imaging session can start with the perfusion scan following the standard calibration scans. A 3D FFE sequence with TR/TE=3.5 ms/1.5 ms, SENSE factor: 2.5(AP), 2(RL), flip angle=30°, with dynamic scan time of 2.9 seconds can be used and 7 or more slices in sagittal orientation with 6 mm thickness and 1.9 mm*1.9 mm pixel size can be acquired. In one example a total of 114 volumes could be collected, with 2 or more of them before contrast injection. After the dynamic scans, T1 weighted anatomical images in sagittal plane can be collected using a TSE sequence with 0.5*0.5*3 mm$^3$ voxel size. Fourteen slices might cover the same volume as dynamic scans. TR/TE=900 ms/10 ms, flip angle=90°. This can be followed by a T2 weighted scan that has identical geometry to the T1 scans and TR/TE=2940 ms/120 ms, flip angle=90°. Finally, contrast enhanced angiography scans can be collected. Contrast bolus arrival can be observed real-time using a single, 50 mm thick coronal slice using FFE sequence in dynamic mode, collecting images every 0.5 s. Once the contrast arrives in a target vessel, actual 3D angiography scan can be started by the operator immediately. In one example, TR/TE=5.1 ms/1.78 ms, voxel size=0.8*0.8*1.5 mm$^3$, with SENSE factor=4 can be used to acquire 50 coronal slices.

Vessels on MRA can be graded as occluded, stenotic or open. Region of interest (ROI)-averaged time course (from whole extremity and/or localized tissue regions) can be converted into a fractional enhancement time course and analyzed using a compartmental or other model (Larsson, et. al. *MRM* 35:716-726, 1996; Workie, et. al. *MRI*, 1201-1210, 2004). In one tissue modeling embodiment, the model fitting can result in 6 parameters: $K^{trans}$ (apparent volume transfer constant), $k_{ep}$ (rate constant), $V_p'$ (apparent fractional plasma volume), E (extraction fraction), tlag (arrival time of tracer in the ROI) and baseline.

Subjects may demonstrate one or more vessels as normal, occluded or stenotic. Subjects may further demonstrate one or more areas of microvascular compromise, which can similarly be rated as normal, occluded or stenotic. Subjects in need of angiogenic treatment may demonstrating an order of magnitude lower value of perfusion and/or microperfusion, indicating a perfusion abnormality beyond any MRA identified lesions. A variety of other perfusion parameters ($k_{ep}$, Vp and E) can be extracted from the acquired data and are helpful in the interpretation. Pixel by pixel images can be generated of any parameter (and through any slice) for visual comparison.

Color coded scans and/or color maps can conveniently and accurately demonstrate the disease visually and may be more adaptable for clinical use (although non-color and other data sets and maps can be used, if desired). Using this technique, data can be entered into a pooled multicenter database. Subsets of patients that may have a significant vascular and resultant ischemic/hypoxic component to their disease can then be identified.

Various methods for studying the vascular anatomy and dynamics of various penile tissue regions in one scanning session using a contrast agent is demonstrated. Penile, pelvic and/or related tissue anatomy, vascular anatomy and sophisticated perfusion data can be obtained. For example, $K_{trans}$ can represent the rate of transfer of contrast delivered to the interstitial tissue, while the $k_{ep}$ is the rate the delivered contrast is cleared from the interstitial tissue, or "wash out". In addition, E (the extraction fraction of contrast during its initial passage within a given volume [ROI]) is another helpful parameter. If decreased blood supply is an etiologic factor in a subset of patients, this technique provides a mechanism by which investigators can study this disease in vivo.

Newer MR techniques such as MR Spectroscopy can be added to identify metabolic abnormalities within various tissues. For example, lactate, an end product of anaerobic metabolism, may be increased in tissues that obtain their nutrients from microvasculature with poor perfusion.

Ex. 3—DCE-MRI and Vessel Perfusion

In another exemplary embodiment, DCE-MRI could be performed as the last scan in a given imaging session. One exemplary protocol based on a 3D gradient-echo sequence could employ the following parameters: TR=3.4 ms, TE=1.2 ms, Flip-angle=30°, NEX=1, and 36.4 sec. temporal resolution.

Any number of dynamic frames could be taken. For example, 22 dynamic frames may be prescribed, with a contrast agent administered manually as a bolus w/a saline flush via a vein at the onset of the $3^{rd}$ dynamic frame. The overall injection time of both the contrast and saline can be less than 10 seconds. Various contrast agents may be used, including 0.1 mmol/kg of Gadopentetic acid or Magnevist (commercially available from Bayer Schering Pharma of Berlin-Wedding, Germany). If desired, an identical single-frame image could be acquired 20 or more minutes later to observe any delayed gadolinium enhancement in various tissues.

The generation of a contrast-induced signal enhancement map (SE-map) of the relevant data and a subsequent analyses can be performed. If desired, the contrast-induced signal enhancement in DCE-MRI can be normalized into percentage enhancement by first subtracting the baseline (which can be the mean of 2 pre-contrast dynamic frames) from all subsequent post-contrast time frames (i.e., from the $3^{rd}$ to the last dynamic frames) and then dividing the differences by the baseline. This operation can be carried out either in a pixel-by-pixel basis for creation of an enhancement map or in a region-of-interest (ROI)-averaged sense for enhancement time-course. The T2 scan can be used to indicate the area analyzed by the pixel-by-pixel created color enhancement map of the tissue perfusion. A graph could show time course data from ROI's. Rectangles placed on various tissue structures could represent ROI's drawn and/or derived (i.e., by a user and/or a computer modeling program).

Various aspects of the data can be examined, either alone or in various combinations, including spatial maps of signal enhancement at one or more fixed time points and an ROI-averaged temporal characteristic in the time course data. Spatial mapping can yield results and/or quantities reflecting an effective capillary perfusion.

Other parameters derived from the temporal characteristic can provide complementary information regarding changes in the microvascular structure, such as the capillary structures and/or venous structures of the corpus cavernosum. For the temporal analysis, the volume-averaged signal enhancement time course can be generated. The enhancement time course can be initially analyzed in a semi-quantitative manner, assessing the parameters such as the maximum enhancement value (%), the time-to-peak (sec), and the clearance rate (%/sec), which in this example could be defined as the slope of the straight line between the $4^{th}$ and the last ($22^{nd}$) frame. Other quantitative analyses based on a compartmental model, shape-based fitting and/or non-linear pharmacokinetic models could be utilized.

Female Erectile Dysfunction

In many instances, vasculogenic erectile difficulties can affect female patients, with various similar and/or additional effects as compared to male patients. The first phase of the female sexual response, associated with neurotransmitter-mediated vascular smooth muscle relaxation, desirably results in increased vaginal lubrication, wall engorgement and luminal diameter as well as increased clitoral length and diameter. However, physiologic impairment of the female vascular system in the pelvic anatomy can result in vasculogenic female sexual dysfunction including vaginal engorgement insufficiency syndrome and clitoral erectile insufficiency syndrome. Such syndromes can exist when, during sexual stimulation, abnormal arterial circulation into the vagina or clitoris, usually from atherosclerotic vascular disease, interferes with normal vascular physiologic processes. Clinical symptoms can include delayed vaginal engorgement, diminished vaginal lubrication, pain or discomfort with intercourse, diminished vaginal sensation, diminished vaginal orgasm, diminished clitoral sensation and/or diminished clitoral orgasm. In addition to vascular disease and/or other degenerative disease conditions, diminished vaginal and/or clitoral arterial blood can result from injuries and/or surgeries, such as non-atherosclerotic, traumatic vascular disease of the ilio-hypogastric-pudendal arterial bed from pelvic fractures or blunt perineal trauma.

In various embodiments, a treatment plan can include imaging, analysis and identification of the hemodynamic integrity of the ilio-hypogastric-pudendal arterial bed to the vagina and clitoris, desirably identifying abnormal vascular or other tissues within a specific region of the pelvic and/or vaginal/clitoral anatomy, which may be utilized by a physician to plan and execute a course of treatment which improves and/or enhances vaginal/clitoral blood flow in patients with vasculogenic female sexual dysfunction. If desired, the treatment may seek to isolate and/or minimize the effects of the abnormal tissue, while optionally increasing and/or maximizing the effects of the remaining healthy and/or less-damaged tissues (i.e., of similar type), which may ultimately restore a desired level of function to the remaining more-normal tissues.

In an initial step, anatomical image data is obtained of an individual female patient's anatomy. This image data can be derived from a wide variety of sources, including MRA (magnetic resonance angiography), MRI (magnetic resonance imaging), x-ray imaging, cone beam CT, digital tomosynthesis, duplex ultrasound, angiography, fluoroscopy, CT scans or PET or SPECT scans. Desirably, image data is obtained that includes the patient's biological structure(s) of interest, which in one exemplary embodiment includes anatomical structures and/or blood flow data of the vasculature supplying to and draining from the vaginal and/or clitoral anatomy—which in various embodiments may specifically be one or more of the following: vaginal wall and clitoral blood flow, vaginal wall and clitoral intra-cavernosal pressure, vaginal and anterior vaginal wall lengths, vaginal luminal pressure, position of the uterus and/or aorto-iliac angiography. Additional data such as blood levels of cholesterol and triglycerides and/or vaginal wall and clitoral erectile tissue histology may be obtained, if desired. For example, pixel or voxel data from one or more radiographic or tomographic images of the patient's anatomy can be obtained using magnetic resonance angiography. Other imaging modalities known in the art such as MRI, ultrasound, laser imaging, PET, SPECT, radiography including digital radiography, digital tomosynthesis or cone beam CT can be used. Contrast enhanced imaging can be employed, if desired.

For example, imaging and analysis might identify significantly less increase in blood flow, wall pressure and/or length changes in the vaginal and/or clitoral anatomy of an imaged patient as compared to similar patients and/or a control value, which might indicate that the patient may be suffering from atherosclerosis or other conditions, including cavernosal artery atherosclerotic changes, diffuse vaginal and/or clitoral fibrosis and/or moderate to severe atherosclerotic occlusions. In some embodiments, this image data can be modeled (as previously described), and the data and/or model utilized by a physician to plan and execute a course of treatment, such as the various treatments described herein (desirably accounting for anatomical and/or physiological differences between females and males).

HEADINGS

The headings provided herein are merely for the reader's convenience, and should not be construed as limiting the scope of the various disclosures or sections thereunder, nor should they preclude the application of such disclosures to various other embodiments or sections described herein.

INCORPORATION BY REFERENCE

The entire disclosure of each of the publications, patent documents, and other references referred to herein is incorporated herein by reference in its entirety for all purposes to the same extent as if each individual source were individually denoted as being incorporated by reference.

EQUIVALENTS

Although the invention has been described and illustrated with a certain degree of particularity, it is understood that the disclosure has been made only by way of example, and that numerous changes in the conditions and order of steps can be resorted to by those skilled in the art without departing from the spirit and scope of the invention. The invention may be embodied in other specific forms without departing from the spirit or essential characteristics thereof. The foregoing embodiments are therefore to be considered in all respects illustrative rather than limiting on the invention described herein. The scope of the invention is thus intended to include all changes that come within the meaning and range of equivalency of the claims provided herein.

The invention claimed is:

1. A method of treating an erectile condition of a subject, comprising:
    obtaining non-invasive image data of at least a portion of a pelvic region of the subject, the non-invasive image data including a region of pelvic vasculature,
    analyzing the image data to preoperatively identify at least one ischemic region of the pelvic vasculature,
    preoperatively identifying a first treatment site proximate to the ischemic region of the pelvic vasculature,
    administering a therapeutically effective amount of a first composition comprising at least one angiogenic factor to the first treatment site, wherein the administration of the angiogenic factor induces growth of blood vessels and angiogenesis at a location proximate to the ischemic region of pelvic vasculature.

2. The method of claim 1, wherein the growth of blood vessels and angiogenesis increases a flow of blood through the ischemic region of pelvic vasculature.

3. The method of claim 1, wherein the step of administering the therapeutically effective amount of the first composition comprises topically applying the first composition to a region of skin tissue at the first treatment site.

4. The method of claim 1, wherein the step of administering the therapeutically effective amount of the first composition comprises injecting the first composition into the first treatment site.

5. The method of claim 1, wherein the step of administering the therapeutically effective amount of the first composition comprises introducing the first composition intravenously into the vascular system of the patient.

6. The method of claim 1, wherein the step of analyzing the image data to preoperatively identify at least one ischemic region of the penile vasculature comprises creating a hemodynamic model of at least a portion of the pelvic blood flow.

7. The method of claim 1, wherein the first treatment site is located upstream from the ischemic region.

8. The method of claim 1, wherein the at least one angiogenic factor comprises FGF-1.

9. The method of claim 1, wherein the region of pelvic vasculature includes a region of penile vasculature.

10. The method of claim 1, wherein the region of pelvic vasculature includes a region of clitoral vasculature.

11. The method of claim 1, wherein the hemodynamic model of at least a portion of the pelvic blood flow region of the pelvic vasculature includes a hemodynamic model of the penile vasculature of the patient.

12. The method of claim 1, wherein the hemodynamic model of at least a portion of the pelvic blood flow region of the pelvic vasculature includes a hemodynamic model of the clitoral vasculature of the patient.

13. A method of treating an erectile condition of a subject, comprising:
    obtaining non-invasive image data of at least a portion of a pelvic region of the subject, the non-invasive image data including a region of pelvic vasculature;
    analyzing the image data to preoperatively identify at least one hyperperfused region of the pelvic vasculature;
    preoperatively identifying a first treatment site proximate to the hyperperfused region of the pelvic vasculature; and
    administering a therapeutically effective amount of a first composition comprising a constrictive agent into the first treatment site, wherein the administration of the constrictive agent reduces blood flow through the hyperperfused region of the pelvic vasculature.

14. The method of claim 13, wherein the constrictive agent comprises a cyanoacrylate adhesive.

15. The method of claim 13, wherein the constrictive agent comprises a vasoconstrictive agent.

16. The method of claim 13, wherein the constrictive agent comprises pseudoephedrine.

17. The method of claim 13, wherein the hyperperfused region of the pelvic vasculature comprises a venous blood drainage network of a penis.

18. A method for improving blood flow in a region of ischemic subsurface tissue of the pelvis:
    obtaining non-invasive image data of at least a portion of a pelvic region of the subject;
    analyzing the image data to preoperatively identify at least one ischemic region of pelvic vasculature within the pelvic region; and
    applying to a tissue site adjacent to the ischemic region an effective amount of a compound comprising FGF-1, wherein the effective amount of the compound promotes angiogenesis within at least a portion of the ischemic region, thereby improving blood flow in the region of ischemic subsurface tissue.

19. The method of claim 18, wherein the step of applying to the tissue site adjacent to the ischemic region an effective amount of a compound comprising FGF-1 comprises applying to a surface tissue site adjacent to the ischemic region an effective amount of a compound comprising FGF-1.

20. The method of claim 18, wherein the step of applying to the tissue site adjacent to the ischemic region an effective amount of a compound comprising FGF-1 comprises applying to a subsurface tissue site adjacent to the ischemic region an effective amount of a compound comprising FGF-1.

* * * * *